United States Patent
Sarabandi et al.

(10) Patent No.: US 11,771,569 B2
(45) Date of Patent: Oct. 3, 2023

(54) SYSTEM AND METHOD FOR ALIGNING HIP REPLACEMENT PROSTHESES

(71) Applicant: THE REGENTS OF THE UNIVERSITY OF MICHIGAN, Ann Arbor, MI (US)

(72) Inventors: Kamal Sarabandi, Ann Arbor, MI (US); Mani Kashanianfard, Ann Arbor, MI (US); Aidin Eslam Pour, Ann Arbor, MI (US)

(73) Assignee: REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 17/043,642

(22) PCT Filed: Mar. 29, 2019

(86) PCT No.: PCT/US2019/025051
§ 371 (c)(1),
(2) Date: Sep. 29, 2020

(87) PCT Pub. No.: WO2019/191722
PCT Pub. Date: Oct. 3, 2019

(65) Prior Publication Data
US 2021/0015634 A1    Jan. 21, 2021

Related U.S. Application Data

(60) Provisional application No. 62/650,429, filed on Mar. 30, 2018.

(51) Int. Cl.
*A61F 2/32* (2006.01)
*A61F 2/34* (2006.01)
(Continued)

(52) U.S. Cl.
CPC .............. *A61F 2/4684* (2013.01); *A61F 2/32* (2013.01); *A61F 2/34* (2013.01); *A61F 2/3609* (2013.01);
(Continued)

(58) Field of Classification Search
CPC ...... A61F 2/32; A61F 2/34; A61F 2/36; A61F 2/3609; A61F 2/4684; A61F 2002/30079;
(Continued)

(56) References Cited

U.S. PATENT DOCUMENTS

| 6,245,109 B1 * | 6/2001 | Mendes | .................. A61F 2/468 |
|---|---|---|---|
| | | | 623/18.11 |
| 9,314,188 B2 | 4/2016 | Hladio et al. | |

(Continued)

FOREIGN PATENT DOCUMENTS

| CN | 102885626 B | 1/2015 |
|---|---|---|
| WO | WO-03/073951 A1 | 9/2003 |

(Continued)

OTHER PUBLICATIONS

ArthroSight-PS™, Arthromeda, retrieved from the Internet at: <http://www.arthromeda.com/arthrosight-ps>.

(Continued)

*Primary Examiner* — Dinah Baria
(74) *Attorney, Agent, or Firm* — MARSHALL, GERSTEIN & BORUN LLP

(57) ABSTRACT

In one aspect, a system and method for aligning hip replacement prostheses comprises an acetabular liner having an inner concave surface and an outer convex surface. The acetabular liner includes at least two magnetic sensors arranged in a spatially distributed manner. The system and method also include a prosthetic femoral component comprising a femoral head component. The femoral head component and the acetabular liner component are shaped such (Continued)

that a ball and socket joint is formed when the femoral head component comes into contact with the inner concave surface of the acetabular liner. While the ball-and-socket joint is formed, and in at least some orientations of the femoral head component relative to the acetabular liner component, a contact point on an external surface of the femoral head component contacts the inner concave surface. The femoral head component includes at least one permanent magnet.

25 Claims, 25 Drawing Sheets

(51) Int. Cl.
　　*A61F 2/36* 　　(2006.01)
　　*A61F 2/46* 　　(2006.01)
　　*A61F 2/30* 　　(2006.01)
(52) U.S. Cl.
　　CPC ............ *A61F 2002/3067* (2013.01); *A61F 2002/30079* (2013.01); *A61F 2002/30698* (2013.01); *A61F 2002/4666* (2013.01)
(58) Field of Classification Search
　　CPC ...... A61F 2002/4666; A61F 2002/3067; A61F 2002/30698
　　See application file for complete search history.

(56) References Cited

U.S. PATENT DOCUMENTS

| | | | |
|---|---|---|---|
| 2013/0053859 A1* | 2/2013 | Penenberg | A61F 2/4609 606/91 |
| 2015/0289890 A1 | 10/2015 | Chen et al. | |
| 2017/0119475 A1 | 5/2017 | McCabe et al. | |
| 2017/0354505 A1* | 12/2017 | Behzadi | A61F 2/3662 |
| 2018/0116823 A1* | 5/2018 | Johannaber | A61F 2/4657 |

FOREIGN PATENT DOCUMENTS

| | | |
|---|---|---|
| WO | WO-2009/067235 A1 | 5/2009 |
| WO | WO-2013/049534 A1 | 4/2013 |
| WO | WO-2015/054745 A1 | 4/2015 |

OTHER PUBLICATIONS

Hip Navigation, BrainLab, retrieved from the Internet at: <https://www.brainlab.com/surgery-products/overview-spinal-trauma-products/trauma-navigation/>.

HipAlign®, OrthAlign, retrieved from the Internet at: <http://www.orthalign.com/hipaligin-technoloqy/>.

Intellijoint Hip®, Intellijoint Surgical, retrieved from the Internet at: <https://www.intellijointsurgical.com/intellijoint-hip-overview/>.

Mako Total Hip, Stryker, retrieved from the Internet at: <https://patients.stryker.com/hip-replacement/options/mako-robotic-arm-assisted>.

Su et al., Design of a computer-aided visual system for total hip replacement surgery, 2015 IEEE International Symposium on Circuits and Systems (ISCAS) pp. 786-789 (2015).

Su et al., Monocular Vision- and IMU-Based System for Prothesis Pose Estimation During Total Hip Replacement Surgery. IEEE Transactions on Biomedical Circuits and Systems, pp. 661-670 (2017).

* cited by examiner

SYSTEM AND METHOD FOR ALIGNING HIP REPLACEMENT PROSTHESES

CROSS-REFERENCE TO RELATED APPLICATIONS

This claims the benefit of U.S. Provisional Patent Application No. 62/650,429, filed on Mar. 30, 2018 and entitled "Systems and Methods for Aligning Hip Replacement Prostheses," the disclosure of which is hereby incorporated herein by reference in its entirety.

TECHNICAL FIELD

The present application relates generally to medical devices for hip arthroplasty procedures and, more specifically, to high-precision systems and methods for aligning hip replacement prostheses.

BACKGROUND

By 2030 more than 500,000 primary total hip arthroplasties will be performed annually in the USA. Hip dislocation is one of the more common complications, resulting in patient dissatisfaction, medical litigation, and costly revision surgeries. Hip dislocation is also the most common cause (22.5%) of revision hip arthroplasty, which is a significant financial burden on both patients and the health system.

This complication occurs mostly in the sitting position or while trying to stand up from the sitting position, but it can occur in the standing position as well. Hip dislocation can affect routine daily activities such as use of the bathroom and traveling. Even if treated non-operatively, hip instability/ dislocation may impair daily activities of living and the ability to work.

The reduction of the hip joint in either emergency rooms under sedation or in the operation room, and the use of hip dislocation braces, are very costly and often ineffective. For example, each dislocation that undergoes revision arthroplasty can cost about $100,000. With the estimation of 500,000 total hip arthroplasties performed annually, and estimated rates of dislocation, 5,000-25,000 dislocations can be expected each year.

Accordingly, if an improved understanding of the hip-spine relation could lower the rate of dislocation by 1% (e.g., from 1.5% to 0.5%), health care costs could be reduced by $500,000,000 or more. Moreover, some revision arthroplasties to treat hip instability will still fail due to a lack of understanding of the mechanism of failure, and will require another revision surgery. This additional revision surgery adds to the cost of patient care, adds to patient dissatisfaction, and is often ineffective.

FIGS. 1A and 1B provide an example of a traditional hip arthroplasty trial components and associated dislocation points, respectively. As shown in FIG. 1A, traditional trial components may include a trial acetabular liner 102 (also referenced herein as a "trial acetabular liner component," "acetabular liner component," or simply "acetabular liner"), a trial femoral head 104 (also referenced herein as a "femoral head component"), a trial femoral neck 106, and a trial broach 108.

To perform a hip arthroplasty, a surgeon generally prepares the acetabulum of the hip with reamers and places an acetabular implant in the acetabulum (not shown). Next, the surgeon places the trial acetabular liner 102 inside the acetabular implant. The next step is preparing the femur with the trial broach 108. The surgeon may then connect the trial femoral neck 106 to the trial femoral head, and place the trial femoral head 104. The hip is then reduced, and the trial femoral head 104 placed into the acetabular liner 102 (e.g., similar to the configuration shown in FIG. 1A) by moving the leg. Thereafter, the surgeon will need to check the hip for stability.

For example, the surgeon may conduct a stability test in the operation room regardless of the method used for the implantation. This test may include reduction of the hip with trial implants and then taking the hip through various ranges of motion (i.e., flexion, extension, internal and external rotations). The hip may dislocate with less than the expected range of motion if the implant is not in optimal position or orientation. Hence, the surgeon must know the femoral head component 104 is in full contact with the acetabular liner component 102 during the hip stability test. However, full contact may not be guaranteed because the hip joint itself is often obstructed by muscles and is not visible during the surgery.

Generally speaking, there are three main reasons for postoperative hip dislocation. The less common causes are severe abductor muscle weakness and severe polyethylene wear. These causes of dislocation are slow developing and usually occur more than 15-20 years from surgery. The third and most common type, illustrated in FIG. 1B, is due to non-optimal implant orientation, which, for example, may be a surgical technique error.

As illustrated in the dislocation illustration 120 of FIG. 1B, a non-optimal orientation may result in dislocation of the femoral head component when the femoral bone 122 and pelvic bone 124 contact to create bony impingement 126 or when the femoral neck component 140 and the acetabular implant 142 contact to create implant impingement 144. These types of dislocation may, for example, occur within the first year after a total hip arthroplasty procedure. Thus, it is critical to understand the acceptable ranges of motion for both the patient and the implant device before conducting a hip arthroplasty procedure.

Conventionally, to prevent dislocations, a manual stability test may be performed without any digital guidance. Surgeons generally have to place their finger around the trial femoral head to see if it dislocates during the test. This manual examination increases the possibility of contamination and infection, and is very inaccurate. If instability is detected during the test, then the exact cause of a dislocation may be uncertain. In other words, the dislocation may be due to impingement between the acetabular and femoral implants or bony impingement between the pelvis and acetabulum.

Moreover, surgeons may not know exactly where the impingement leading to dislocation occurs. As a result, reorientation of the implants to achieve stability may be performed by guessing. Hence, even after successful hip arthroplasty, dislocations can occur regularly and solutions are desired to reduce the rates of postoperative hip dislocation.

FIGS. 2A and 2B provide frontal, side, and top-down views of patient and hip implant ranges of motion. In FIG. 2A, in each of a standing FIG. 200, a sitting figure 220, and a transition FIG. 240, patient ranges of motion are superimposed over the prosthetic range of motion. For example, the standing FIG. 200 includes a frontal patient range of motion 202 and a frontal prosthetic range of motion 204, a side patient range of motion 206 and a side prosthetic range of motion 208, and a top-down patient range of motion 210 and a top-down prosthetic range of motion 212.

As a natural consequence of a patient engaging in a stance or orientation similar to that represented in the standing FIG. 200, the patient's pelvis may be slightly tilted forward. Additionally, the patient may have 30-40 degrees of hip flexion, and their hip may be within 10 degrees of neutral rotation. However, it should be understood that a patient may have a more extensive range of motion depending on the activity.

The sitting figure 220 includes a frontal patient range of motion 222 and a frontal prosthetic range of motion 224, a side patient range of motion 226 and a side prosthetic range of motion 228, and a top-down patient range of motion 230 and a top-down prosthetic range of motion 232. As a natural consequence of a patient engaging in a stance or orientation similar to that represented in the sitting figure 220, the pelvis may tilt back. In this position, the patient's hip may have between 50-100 degrees of flexion depending on the type of the chair and may be in 10-30 degrees of abduction.

The transition FIG. 240 includes a frontal patient range of motion 242 and a frontal prosthetic range of motion 244, a side patient range of motion 246 and a side prosthetic range of motion 248, and a top-down patient range of motion 250 and a top-down prosthetic range of motion 252. As a natural consequence of a patient engaging in a stance or orientation similar to that represented in the transition FIG. 240, the patient's pelvis may tilt forward and their hip may be in 90 degrees or more of flexion, 10-20 degrees of abduction, and slightly rotated internally.

Each of the prosthetic ranges of motion may represent, for example, the maximum range of motion of the prosthetic hip before dislocation occurs due to either bone-on-bone or prosthesis-on-prosthesis impingement. Each of the patient ranges of motion may represent, for example, the range of motion that a patient has during different daily activities (e.g., standing, sitting, transitioning from sitting to standing, etc.). The patient ranges of motion may be different among patients and may depend on factors including, for example, body habitus and joint anatomy.

Nevertheless, to prevent dislocation, the patient's range of motion should fall within the prosthetic range of motion. However, conventional systems for computer assisted surgery for total hip arthroplasty do not assess the range of motion of the joint.

FIG. 2B provides illustrations to showcase the proper alignment of the hip implant device by taking various ranges of motion into consideration. For example, the first alignment FIG. 260 includes a first prosthetic alignment 261, a first walking range of motion 262, a first sitting range of motion 263, a first transition range of motion 264, and a first prosthetic range of motion 265. The first prosthetic range of motion 265 may be indicative of the range of motion of the hip implant prosthesis in the first alignment FIG. 260 having the first prosthetic alignment 261. As such, the first prosthetic alignment 261 may be an optimal alignment for the hip prosthesis because each of the first walking range of motion 262, first sitting range of motion 263, and first transition range of motion 264 fall within the first prosthetic range of motion 265.

The second alignment figure 270 includes a second prosthetic alignment 271, a second walking range of motion 272, a second sitting range of motion 273, a second transition range of motion 274, and a second prosthetic range of motion 275. The second prosthetic range of motion 275 may be indicative of the range of motion of the hip implant prosthesis in the second alignment figure 270 having the second prosthetic alignment 271. As such, the second prosthetic alignment 271 may be a non-optimal alignment for the hip implant prosthesis because the second transition range of motion 274 falls outside the second prosthetic range of motion 275. This may indicate, for example, that the hip implant prosthesis has been placed in less anteversion. In this example, the patient's hip may dislocate when the patient attempts to stand from a sitting position, such as attempting to stand up from sitting on a chair.

The third alignment figure 280 includes a third prosthetic alignment 281, a third walking range of motion 282, a third sitting range of motion 283, a third transition range of motion 284, and a third prosthetic range of motion 285. The third prosthetic range of motion 285 may be indicative of the range of motion of the hip implant prosthesis in the third alignment figure 280 having the third prosthetic alignment 281. As such, the third prosthetic alignment 281 may be a non-optimal alignment for the hip implant prosthesis because the third walking range of motion 282 falls outside the third prosthetic range of motion 285. This may indicate, for example, that the hip implant prosthesis has been anteverted too much, and may result in a patient's hip dislocating while walking.

Thus, to prevent postoperative hip dislocation, the acetabular and femoral implants should be placed in optimal position to provide a full range of motion for regular daily activities without impingement. As previously mentioned, conventional techniques involve the use of manual tests and analog insertion guides, but none of the conventional methods consider factors such as, for example, pelvic tilt. Moreover, conventional systems and methods are not universally used, require extensive training, cannot be used in revision surgeries (because they rely on intact acetabular bone for navigation), and are expensive.

Proposed systems and devices for overcoming the drawbacks of these conventional systems have drawbacks as well. For example, U.S. Patent Publication No. 2015/0289890 (now U.S. Pat. No. 10,034,779) to Chen et al. mentions using a magnet to determine the orientation of the femoral head with respect to the acetabular liner. However, Chen et al. does not disclose: (1) the measurement procedure, number or type of sensors, and the sensor placements required to determine the orientation; (2) the ability to determine whether the femoral head is in full contact with the liner; (3) how to handle errors due to sensitivity to variations in the intensity and positioning of the magnet (e.g., due to fabrication tolerances, such as those affecting offset of the magnet relative to the center of the joint); and (4) how to mitigate the adverse effects of noise and interference from outside magnetic sources (including the magnetic field of the earth). Moreover, Chen et al. does not disclose how to detect dislocation due to bony impingement in addition to impingement between a femoral neck component and the acetabular liner component.

Chen et al. also proposes the use of a macroscopic wide-angle camera to recognize large patterns printed on the inside of the acetabular liner, and uses a complex pattern matching system to capture the movement of the femoral head. However, this approach also has shortcomings, including: (1) due to significant limitations in pattern matching, correctly identifying position yields relatively large errors (e.g., on the order of 5-10 degrees); (2) to overcome a high error rate, additional measurement devices are needed, such as a gyroscope and pressure sensors, which in turn requires more physical space and a larger battery to power the additional components, and sacrifices the modularity of the device. Because the method proposed by Chen et al. is a wide field of view imaging approach, there must be an unobstructed minimum distance between the lens and acetabular liner. Hence, the trial femoral head must be transparent, leaving a small remaining volume for the power source and other electronics. Lack of modularity is also a serious problem, because there are 2 or 3 different combinations of femoral neck offsets, 5 or 6 different combinations of femoral head diameter, and 6 or 7 different combinations of femoral neck length. Thus, non-modular designs would require surgical sets with approximately 120 different combinations of these components. Further still, the system of Chen et al. integrates pressure sensors on the femoral head, which limits the ability of the system to determine the cause of a dislocation. For example, the system may fail to determine whether a dislocation occurred due to the femoral neck impinging on the acetabular liner, as opposed to a bony impingement.

DETAILED DESCRIPTION

Figure 1A:
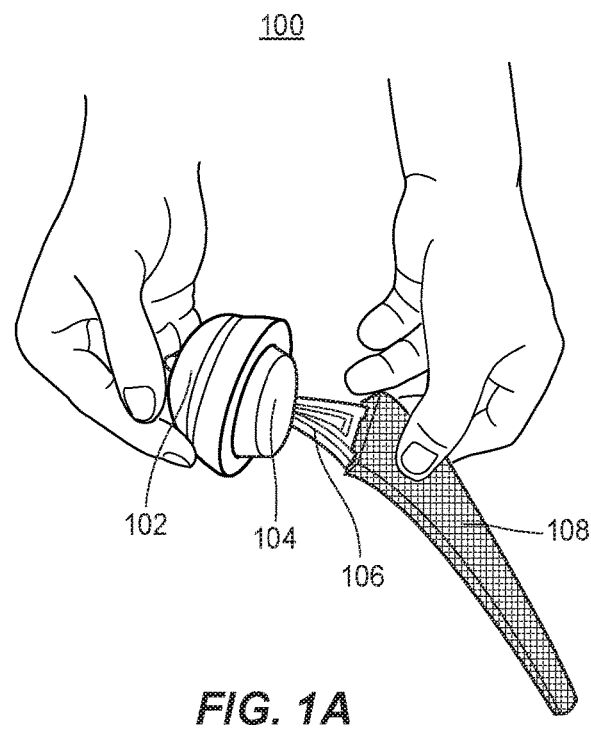
FIGS. 1A and 1B provide an example of traditional hip arthroplasty trial components and associated dislocation points, respectively.
Figure 1B:
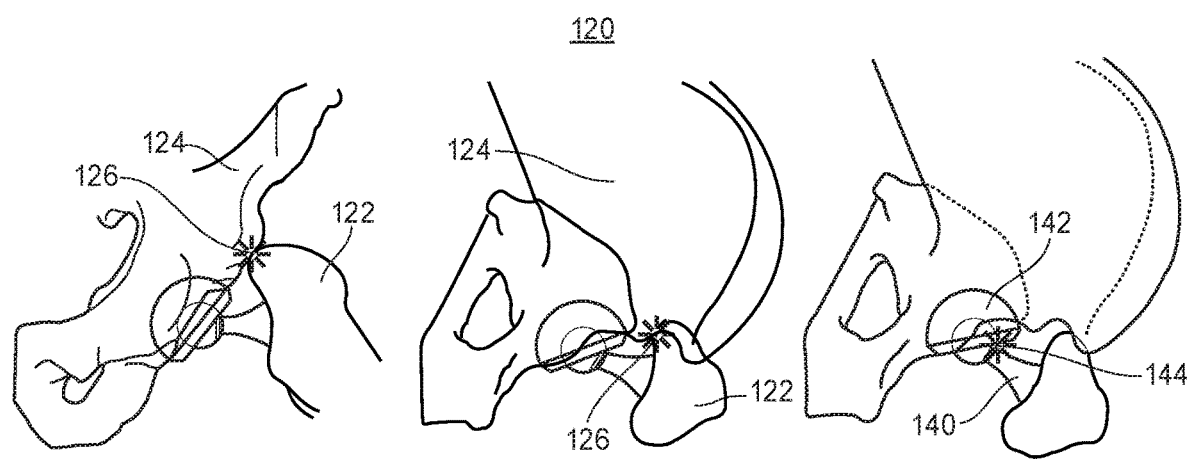
Figure 2A:
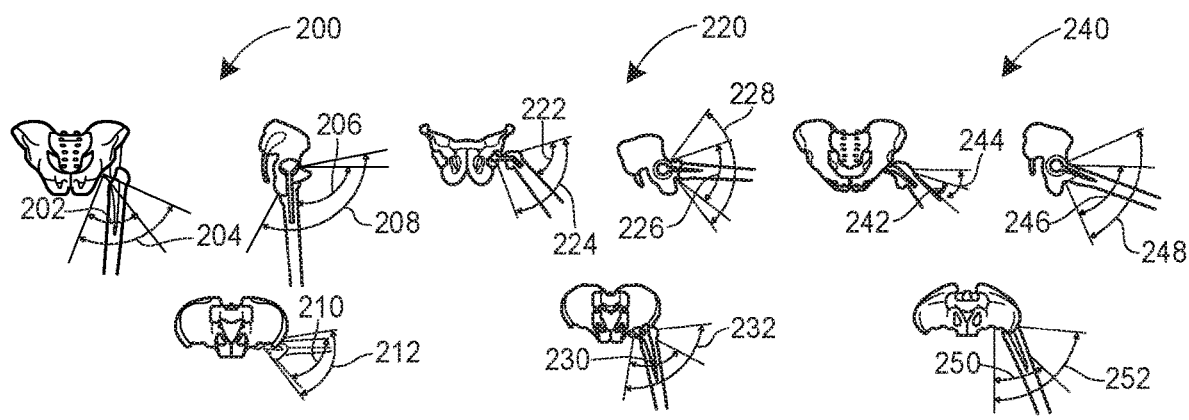
FIGS. 2A and 2B provide frontal, side, and top-down views of patient and hip implant ranges of motion.
Figure 2B:
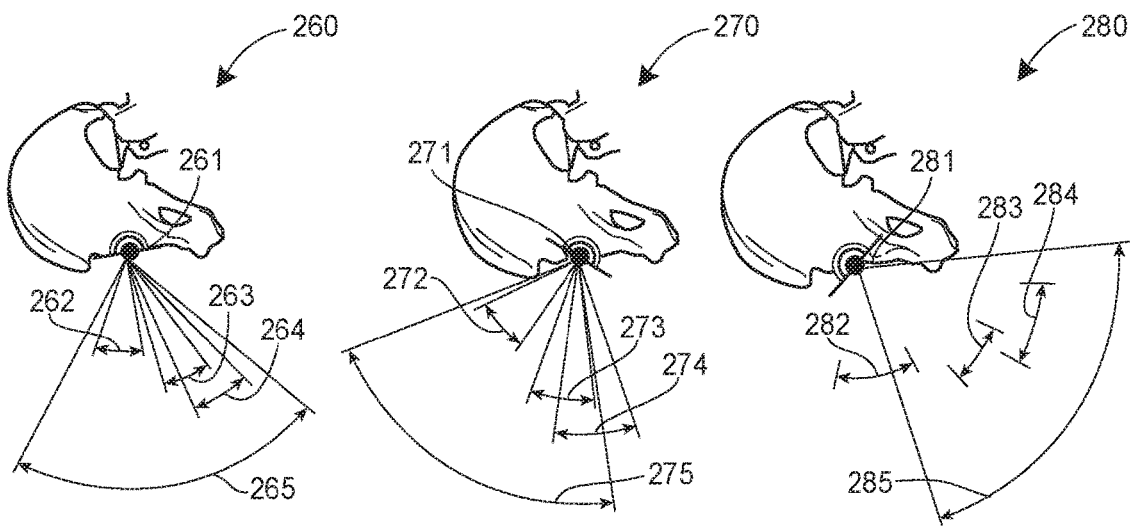

In general, and as further discussed herein, the systems and methods of the present disclosure may provide several advantages over prior systems and methods for aligning hip replacement prostheses.

Namely, in a first aspect of the present disclosure, an array of two or more multiple-axis magnetometers may be strategically positioned and embedded in an acetabular liner component to measure the orientation of the femoral head component with respect to the center of the acetabular liner component, and identify whether the femoral head component is in full contact with the acetabular liner component. This strategic positioning allows the magnetometers to detect dislocation due to bony impingement in addition to impingement between a femoral neck component and the acetabular liner component, which was not possible with prior systems and methods.

Moreover, the array of magnetometers are positioned to reduce the sensitivity of the system to the intensity and positioning of the permanent magnet in the femoral head component. Further, the magnetometer array configuration increases the position accuracy with respect to a single magnetometer configuration, and decreases the impact of noise and external interference (e.g., by measuring and compensating for external magnetic fields such as, for example, the Earth). These benefits are further enhanced by integrating the system into a customized computer environment.

For example, the system may implement a method which can be carried out, at least in part, by an artificial neural network to allow for real-time position calculation from the readings of the at least two magnetic sensors. An efficient mathematical model may then be applied to invert magnetic field vector measurements of the magnetometer array and calculate an accurate position of the femoral head component.

The model may be implemented on a small specialized portable computer that can wirelessly communicate with the micro-processor embedded in the acetabular liner component, for example. After (and/or while) calculating positions, the computer may send graphics indicative of those positions to any display in the operation room. Afterwards, the software that displays and records the data can produce a permanent record of dislocation tests performed by the surgeon during the surgery. Thus, the surgeon (and possibly authorized individuals) will have access to real-time, high-precision data corresponding to the alignment of the hip prosthesis in a manner that was unavailable in prior systems and methods.

A second aspect of the present disclosure includes a high-resolution, miniaturized microscopic optical color detector system with an associated lighting system and wireless transmitter embedded in a femoral head component. An internal surface of an acetabular liner component may be patterned with a fine-resolution color-coded surface to uniquely specify the location of the femoral head component center on the surface of the acetabular liner component.

The second aspect maps the movement of a contact point between the femoral head component and the acetabular liner component. Additionally, the microscopic optical color detector system of the second aspect reads the local unique color which one can use to determine the position of the center of the femoral head component relative to the acetabular liner component with an error significantly lower than conventional systems.

Moreover, the relative simplicity of the design of the second aspect, along with the addition of one or more high-efficiency light emitting diode (LED) or other suitable light sources, allows the system to maintain the desired modularity, and thus lower cost, of the trial components.

It should be understood that the first and second aspects disclosed herein may, in some embodiments, be combined into a single device and/or system.

To solve these and other problems as described herein, systems and methods for properly aligning hip prostheses are disclosed. As noted above, in a first aspect of the present disclosure, a system for properly aligning hip prostheses may include a spatially distributed array of multi-axis magnetometers whose outputs are co-analyzed to achieve very high angular resolution measurements.

Figure 3:
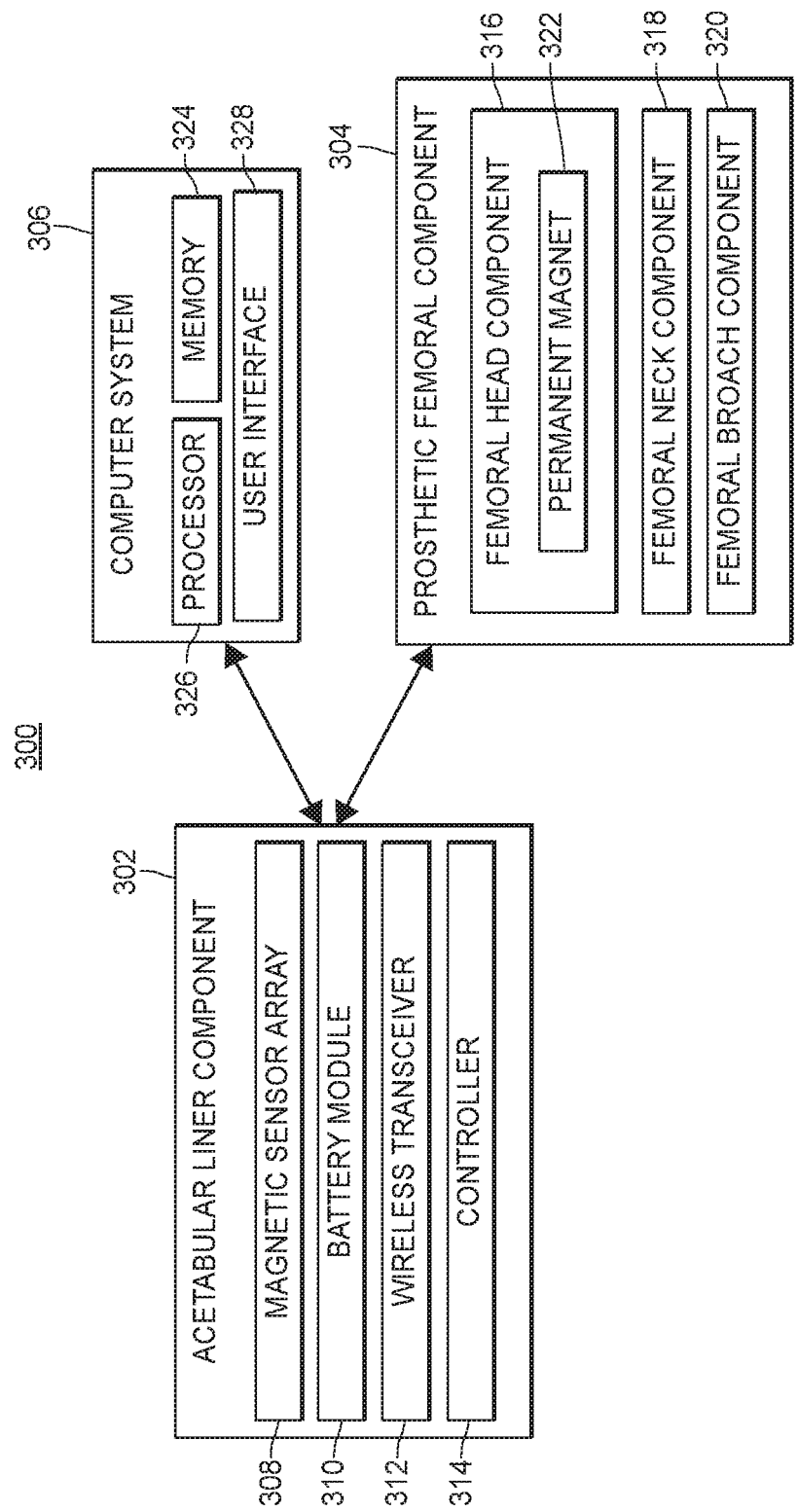
FIG. 3 depicts an example system for aligning hip replacement prostheses, in accordance with a first aspect of the present disclosure that utilizes a permanent magnet and magnet sensor array.

More specifically, and in reference to FIG. 3, a position measurement system 300 may be used in a hip arthroplasty procedure. The system 300 may include an acetabular liner component 302, a prosthetic femoral component 304, and a computer system 306 (also referenced herein as a "computing system"). The acetabular liner component 302 includes a magnetic sensor array 308, a battery module 310, a wireless transceiver 312, and a controller 314.

As further discussed in more detail below with reference to FIGS. 5A and 5B, the acetabular liner component 302 may have an inner concave surface and an outer convex surface. The magnetic sensor array 308 may include at least two magnetic sensors arranged in a spatially distributed manner. In some embodiments, the acetabular liner component 302 also includes a plurality of pressure sensors arranged along an outer perimeter of the inner concave surface.

The prosthetic femoral component 304 of system 300 includes a femoral head component 316, a femoral neck component 318, and a femoral broach component 320. The femoral head component 316 includes at least one permanent magnet 322 embedded therein. In some embodiments, the at least one permanent magnet 322 is entirely embedded in the femoral head component 316. The femoral head component 316 and the acetabular liner component 302 may be shaped such that a ball-and-socket joint is formed when the femoral head component 316 comes into contact with the inner concave surface of the acetabular liner component 302. Moreover, while the ball-and-socket joint is formed, and in at least some orientations of the femoral head component 316 relative to the acetabular liner component 302, the center of an external, convex surface of the femoral head component 316 forms a contact point with the inner concave surface of the acetabular liner component 302.

The femoral head component 316 may be configured to physically couple to the femoral neck component 318 in a removable manner (e.g., snap-fit, or screw and threaded hole arrangement, etc.), and the femoral neck component 318 may be configured to physically couple to the femoral broach component 320 in a removable manner (e.g., snap-fit, or screw and threaded hole arrangement, etc.).

In various embodiments, the acetabular liner component 302 and the prosthetic femoral component 304 are trial components to be removed prior to completion of the hip arthroplasty procedure. For example, a surgeon engaged in a hip arthroplasty procedure may use the system 300 of the present disclosure to accurately determine the ranges of motion with respect to the patient and hip implant device. Once these ranges have been determined, the acetabular liner component 302 and the prosthetic femoral component 304 may be removed, and a hip replacement device which does not contain the various components of the present system 300 may be introduced into the patient to complete the hip arthroplasty procedure.

The wireless transceiver 312 may include one or more antennas and a radio frequency (RF) module (not shown), and be configured to transmit magnetic field data gathered by the magnetic sensor array 308 (and/or data derived therefrom by controller 314) to the computer system 306, external to the acetabular liner component 302. The wireless transceiver 312 may transmit the magnetic field data to the destination external to the acetabular liner component 302 using, for example, a Bluetooth communication protocol. However, the wireless transceiver may use any suitable protocol to transmit the magnetic field data.

The controller 314 of the acetabular liner component 302 may be a microcontroller, for example. The controller 314 may include at least a portion of the wireless transceiver 312, or may be entirely separate from the wireless transceiver 312. The controller 314 may cause the wireless transceiver 312 to transmit the sensor data on a periodic schedule, or on any other suitable time basis. In some embodiments, the controller 314 does not initiate transmissions until some manual step is taken by the surgeon or other user (e.g., activating a control provided by an application executing on computer system 306, which may then send the controller 314, via wireless transceiver 312, an indication that sensor data should be sent).

The battery module 310 may be electrically coupled to the magnetic sensor array 308 and the microcontroller 314. In some embodiments, the magnetic sensor array 308, the microcontroller 314, the wireless transceiver 312, and the battery module 310 are all entirely embedded (e.g., hermetically sealed) in a body of the acetabular liner component 302.

To illustrate, the magnetic sensor array 308 may be embedded in the acetabular liner component 302 to measure the created magnetic field of the permanent magnet 322. While magnet 322 may include multiple magnets, in some embodiments, reference is made herein to only a single "magnet" for ease of explanation. The magnetic sensor array 308 may be chosen and positioned so as to measure all three (independent) components of the local vector magnetic flux density with a very high accuracy in real time. For example, three magnetic sensors may be sufficient to uniquely determine the orientation of the femoral head component 316. The magnetic sensors may be sensors having a high energy efficiency (e.g., minimal current requirements) with continuous operation.

In various embodiments, the computer system 306 comprises a memory 324, a processor 326, and a user interface 328. While referred to herein as a single "processor," in some embodiments processor 326 includes two or more processors. The user interface 328 may include a monitor and any associated hardware, firmware, or software necessary to render images on the monitor.

The memory 324 (e.g., a solid state memory, hard drive, or other suitable memory) may store instructions that, when executed by the processor 326 (e.g., one or more microprocessors), cause the computer system 306 to receive the magnetic field data transmitted by the wireless transceiver 312, and process the received magnetic field data to determine orientations of the femoral head component 316 relative to the acetabular liner component 302. The processing may be performed substantially in real time as the magnetic sensors of the sensor array 308 capture the sensor readings.

As noted above, the data from the magnetic sensors may be collected using the controller 314 and transmitted wirelessly to the processor 326 through a Bluetooth (or other suitable) interface. While not shown in FIG. 3, the computer system 306 also includes, or is coupled to, a wireless transceiver to allow communication with the acetabular liner component 302 using the Bluetooth or other protocol. The processor 326 may then determine the orientation of the femoral head component 316 (e.g., the position of a center of the external convex surface of component 316) based on the magnetic sensor data, and cause the results to be displayed to the surgeon and/or other user(s) in real time.

The wireless transceiver 312 and controller 314 may be included in a single chip that requires, for example, 0.4 mA input current when transmitting data, with the current dropping to 1.5 µA in stand-by mode. Because of the high energy efficiency of the system, a small battery (for battery module 310) may be sufficient to power the acetabular liner component 302 for over 60 surgeries, for example. Therefore, in some embodiments, there is no need to charge the battery module 310. This may allow the entire acetabular liner component 302 to be fabricated in one monolithic piece, with the circuitry being sealed and secluded. This complete integration of the circuitry may facilitate, for example, cleaning and sanitation of the acetabular liner component 302 between procedures.

In any of the preceding embodiments, the body of the acetabular liner component 302 may be hermetically sealed. Moreover, the body of the acetabular liner component 302 may consist solely of a polyurethane material (i.e., a unitary piece of polyurethane material), or may consist of another suitable material, or a combination of materials.

In certain embodiments, the wireless transceiver 312 transmits the magnetic field data to the computer system 306 at a rate of at least 30 frames per second, substantially in real time as the sensor readings are captured by the magnetic sensor array 308. This allows the system 300 to actively track the orientation of the femoral head component 316, which in turn allows the surgeon to make accurate determinations regarding the ranges of motion for both the patient and the hip implant device, as further discussed herein.

Based on the processing step(s) performed by the computer system 306, the instructions stored in memory 324 may further cause the computer system 306 to generate, based on the determined orientations, data representing a path of the contact point (e.g., center point) relative to the acetabular liner component 302. This path of the contact point may then be displayed to a user via the user interface 328 (also referenced herein as "display") in a visual representation, in accordance with instructions stored on the memory 324 of the computer system 306. The display of the path of the contact point may be performed substantially in real time as the magnetic sensor array 308 captures the sensor readings. In some embodiments and/or scenarios, however, the display of the path of the contact point via the user interface 328 is provided after the magnetic sensor array 308 captures the sensor readings.

In addition to visualizing the path of the contact point, the instructions may cause the computer system 306 to generate a visual representation of a "safe zone" relative to the acetabular liner component 302. The safe zone may represent an area of the inner convex surface of the acetabular liner component 302 that, if not exited by the contact point, should not cause hip dislocation to occur. The safe zone is discussed further below in reference to FIGS. 22A and 22B. The instructions may cause the safe zone to be presented on the display 328 in conjunction with the visual representation of the path.

Once the safe zone is determined and presented to the user, the instructions may further cause the computer system 306 to generate one or both of (i) an audible alarm, or (ii) a visual alarm, in certain situations. In particular, the alarm(s) may be generated when the visual representation of the path comes within a threshold distance of a perimeter of the visual representation of the safe zone, and/or when the visual representation of the path goes outside of the perimeter of the visual representation of the safe zone.

In these embodiments, the safe zone may be specific to a patient for which the hip arthroplasty procedure is being performed. Namely, the safe zone may be specific to at least (i) a height of the patient, and (ii) one or more distances between one or more portions of a pelvis of the patient and one or more portions of a femur of the patient, as measured while the patient is in one or more different poses.

In any of the embodiments discussed above, the instructions may cause the computer system 306 to determine the orientations of the femoral head component 316 relative to the acetabular liner component 302 by using the magnetic field data to determine projections of the contact point onto the inner concave surface. These determinations may be performed at least by inputting the magnetic field data (from magnetic sensor array 308), or data derived from the magnetic field data, to a trained neural network implemented by the computer system 306. The trained neural network may process the magnetic field data to output data indicative of the orientations of the femoral head component 316 relative to the acetabular liner component 302. The neural network may be trained in a supervised manner, for example, using magnetic field values (collected by acetabular liner component 300 and/or other similar components) with corresponding labels. The labels may be confirmed orientations/positions (e.g., as determined using conventional methods known in the art) that correspond to each set of magnetic field values.

To further refine the precision of the orientation determinations, the magnetic sensor array 308 may consist of at least two multi-axis magnetic sensors, each having an accuracy of at least 10 micro-Tesla. With these components, the orientations of the femoral head component 316 relative to the acetabular liner component 302 may be accurate to within 0.2 degrees in any direction along the inner concave surface.

Additionally, the instructions may cause the computer system 306 to calibrate the orientation measurements, at least by determining one or more ambient magnetic fields that are measured by the magnetic sensor array 308 while the ball-and-socket joint is not formed. In particular, the instructions may cause the computer system 306 to determine at least one magnetic field calibration factor based on the one or more ambient magnetic fields, and determine the orientations of the femoral head component 316 relative to the acetabular liner component 302 based on the magnetic field data and the at least one magnetic field calibration factor.

Further, in embodiments where the acetabular liner component 302 includes a plurality of pressure sensors arranged along an outer perimeter of the inner concave surface, the instructions may cause the computer system 306 to monitor pressure measurements of the one or more pressure sensors. Based on the monitored pressure measurements, the instructions may cause the computer system 306 to generate an audio or visual indication of when a surface of the acetabular liner component 302 is impinging upon the acetabular liner component 302 (e.g., when at least one of the pressure sensors senses a pressure above some threshold value).

Figure 4:
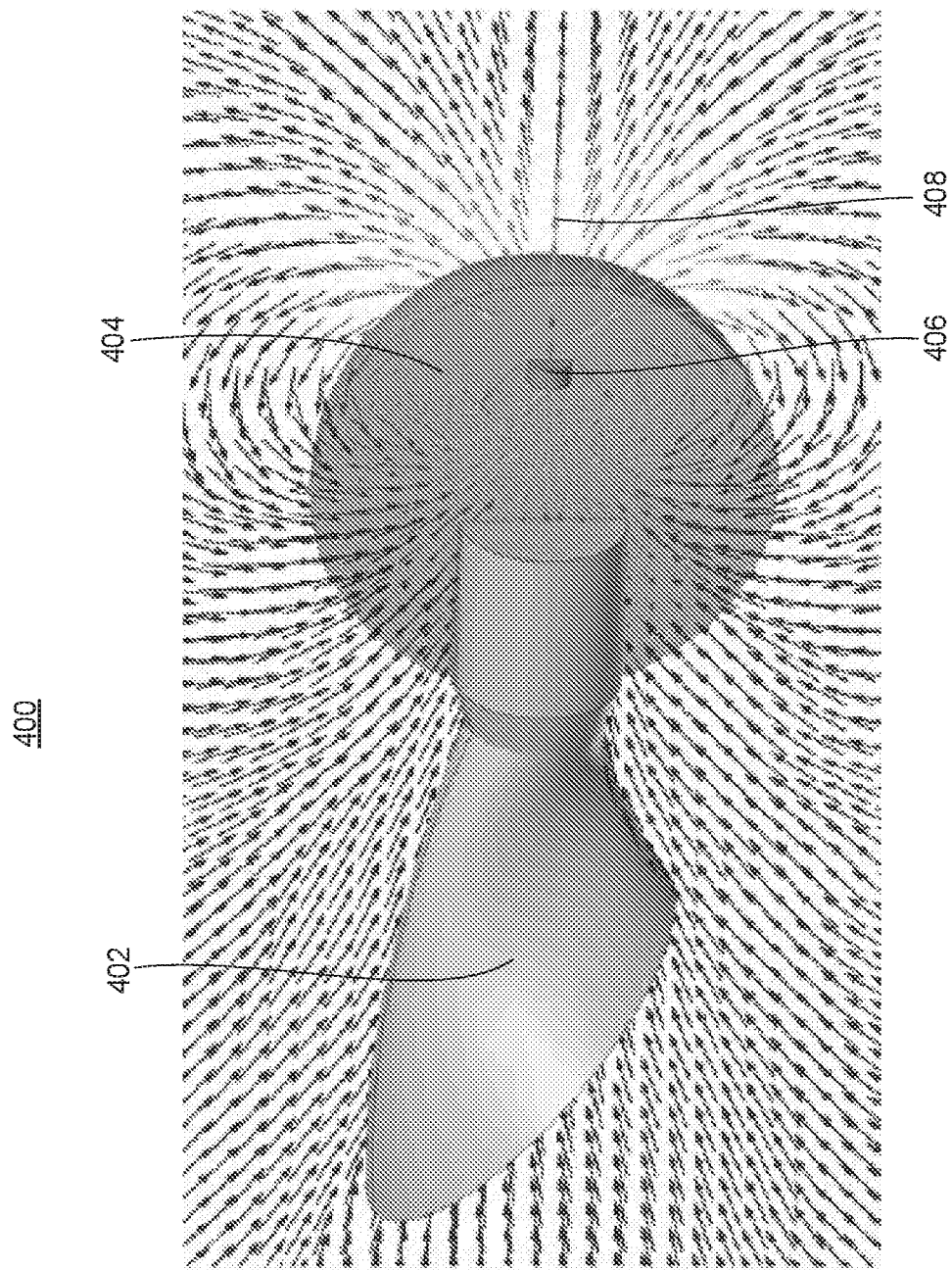
FIG. 4 provides a cutaway illustration of a femoral head component with at least one permanent magnet embedded therein, in accordance with the first aspect of the present disclosure.

FIG. 4 provides a cutaway illustration of a femoral head component with at least one permanent magnet embedded therein, in accordance with the first aspect of the present disclosure. The cutaway illustration 400 features a femoral neck component 402, a femoral head component 404, a permanent magnet 406, and magnetic field lines 408 generated by the permanent magnet 406 and encircling the femoral head component 404. It is to be understood that the strength associated with the magnetic field lines 408 decreases in magnitude as they extend radially outward from the permanent magnet 406.

In one embodiment, the permanent magnet 406 is cylindrical. In this embodiment, the center axis of the cylindrical magnet may pass through the contact (e.g., center) point of the femoral head component 404, and the cylindrical magnet 406 may be positioned between ⅛ inch and ½ inch away from the contact point. Further, the cylindrical magnet 406 may have a radius between 1/32 inch and ⅛ inch, and/or a length between 1/32 inch and ⅛ inch. However, the magnet 406 may have other shapes and/or dimensions in other embodiments.

Moreover, in various embodiments, the permanent magnet 406 may be a neodymium magnet with a grade between N45 and N50. The permanent magnet 406 may include any material sufficient to create a strong static magnetic field with variable intensity and direction around the femoral head component 404.

As the femoral head component 404 rotates on an acetabular liner component (e.g., acetabular liner component 302), the direction and intensity of the magnetic field 408 at different positions on the acetabular liner component surface changes. If the magnetic field 408 generated by the at least one permanent magnet 406 is strong enough, the rotation angle may be determined by measuring the direction and intensity of the magnetic field 408 at one or more locations on the surface of the acetabular liner component.

Figure 5A:
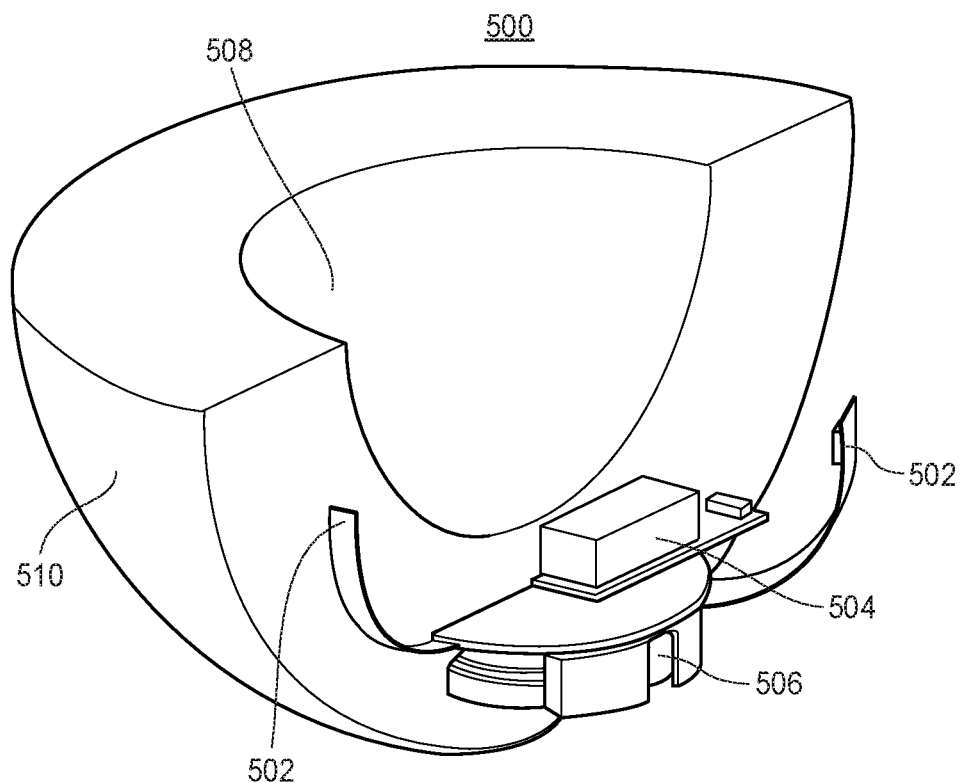
FIGS. 5A and 5B provide a cutaway view and a top-down view of an acetabular liner component with at least two magnetic sensors embedded therein, in accordance with the first aspect of the present disclosure.
Figure 5B:
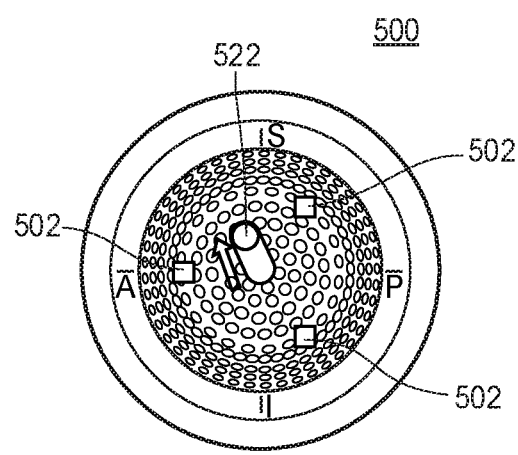

FIGS. 5A and 5B provide a cutaway view and a top-down view, respectively, of an acetabular liner component 500 (e.g., acetabular liner component 302) in accordance with one embodiment of the first aspect of the present disclosure. As illustrated in the cutaway view of FIG. 5A, the acetabular liner component 500 includes magnetic sensors 502, a transceiver module 504, and a battery module 506 all embedded in the acetabular liner component 500. The acetabular liner component 500 has an inner concave surface 508 and an outer convex surface 510. In one embodiment, each of the magnetic sensors 502 is a multi-axis sensor capable of detecting magnetic field intensity and direction in three dimensions.

The magnetic sensors 502 may be evenly spaced relative to each other, and evenly distributed about a center axis of the acetabular liner component 500, and each of the magnetic sensors 502 may be on or immediately adjacent to the inner concave surface 508, or embedded within the liner component 500 at some suitable depth relative to the inner concave surface 508 (e.g., to maintain a hermetical seal). While not shown in FIG. 5A, the magnetic sensors 502 may, in one embodiment, include three magnetic sensors which may be evenly spaced relative to each other, and evenly distributed about a center axis of the acetabular liner component 500. Each of the three magnetic sensors may be on or immediately adjacent to the inner concave surface 508, or embedded within the liner component 500 at some suitable depth relative to the inner concave surface 508 (e.g., to maintain a hermetical seal).

As illustrated in the top-down view of FIG. 5B, a point of contact 522 may represent the center of the femoral head component (e.g., femoral head component 316) while in a particular orientation relative to the acetabular liner component 500. The magnetic sensors 502 may provide magnetic field values that enable the computer system 306 to determine the location of the point of contact 522, via triangulation of the detected magnetic field intensities and directions at each of the at magnetic sensors 502. In this way, the magnetic sensors 502 may enable tracking of the movement of the point of contact 522 as the femoral head component (e.g., femoral head component 316 with magnet 322) moves in relation to the acetabular liner component 500.

Figure 6:
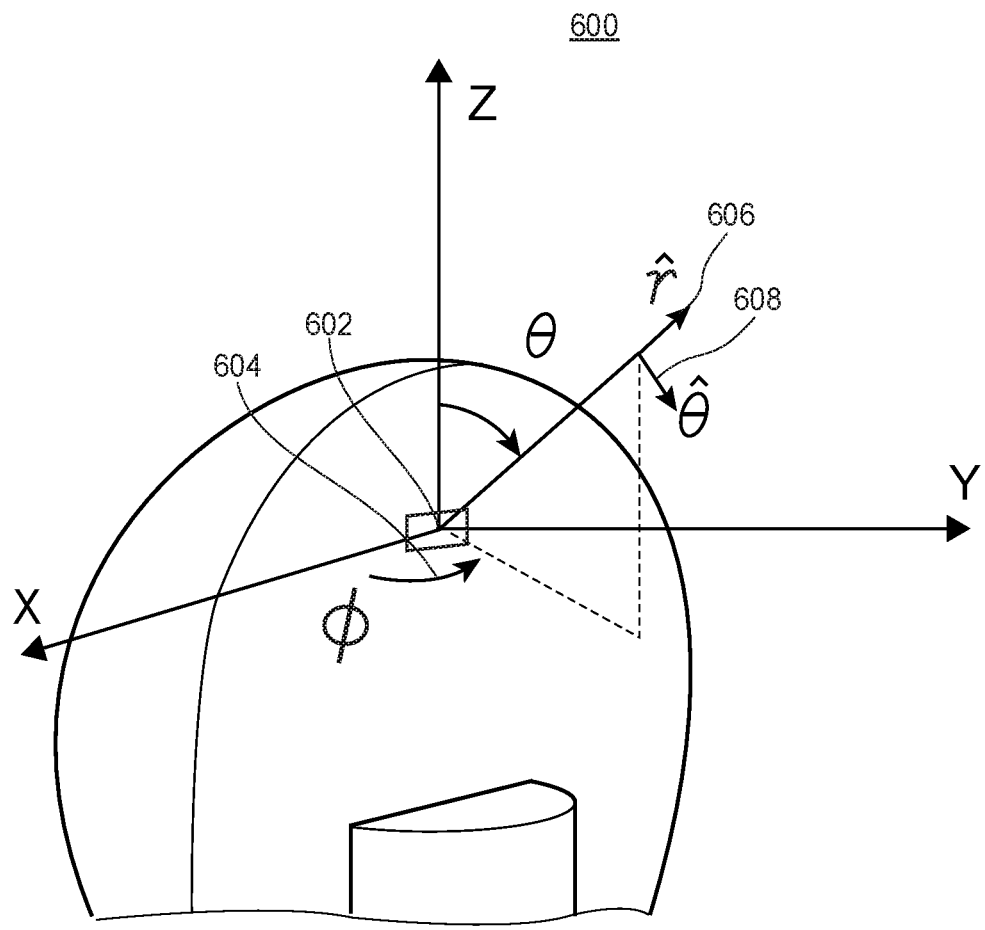
FIG. 6 provides another cutaway illustration of a femoral head component with at least one permanent magnet embedded therein, and the associated vector components of the at least one permanent magnet, in accordance with the first aspect of the present disclosure.

FIG. 6 provides another cutaway illustration of a femoral head component 600 (e.g., femoral head component 316) with a permanent magnet 602 embedded therein (e.g., magnet 322), and the associated vector components 604, 606, 608 of the permanent magnet 602, in accordance with the first aspect of the present disclosure. The vector components include a horizontal rotation vector component 604, a radial vector component 606, and a vertical rotation vector component 608.

Using the various vector components 604, 606, 608 and physical characteristics of the at least one permanent magnet 602, the computer system 306 can calculate/approximate the magnetic flux density. Namely, the magnetic flux density of the permanent magnet 602 with a thickness L and radius R can be approximated as follows:

$$\vec{B} = \frac{1}{4} \frac{LR^2 B_r}{r^3} (2\cos\theta \hat{r} + \sin\theta \hat{\theta}), \quad (1)$$

where Br is the remanence field of the permanent magnet 602 and depends on the material and process used to fabricate the permanent magnet 602. For example, the remanence field of a grade 48 Neodymium magnet is around 1.4 Tesla (T). Assuming a relatively small grade 48 magnet with L=R=1/16 inch placed 3/8 inch away from the center point of the femoral head component 600, and a diameter of D=5/4 inch, the strongest magnetic flux density on the surface of the femoral head component 600 may be approximately 11 mT. This field is 200 times as strong as the magnetic field of the Earth and can be measured with an accuracy of better than 1 part in 10,000.

Using this approximation, the location of the femoral head component 600 with respect to the acetabular liner component (e.g., acetabular liner component 500) may be determined using the measured magnetic field at a few locations on the surface of the acetabular liner component, e.g., as was illustrated in FIG. 5B. Finding the magnetic field at the location of the magnetic sensors 502 using the above approximation may be trivial. However, finding the location of the femoral head component 600 using the magnetic sensor data may not be solved theoretically. Numerical solutions may be developed to find the location of the projection of the center point of the femoral head component 600 onto the acetabular liner component using the sensor data.

For example, assuming three magnetic sensors are used, the problem may reduce to fitting a multidimensional function that relates the nine components of the measured magnetic field (three components for each sensor) to the location of the center point of the femoral head component 600, which can be uniquely represented by two variables (e.g., x and y, r and θ, or θ and φ). Because the intensity of the permanent magnet 602 can vary up to 10% because of manufacturing tolerances and deterioration over time, the system must perform well independent of the strength of the permanent magnet 602. Therefore, the sensor readings at any given time may be first normalized to offset any gradual or statistical variance in the intensity of the at least one permanent magnet 602 used. This normalization may reduce the number of independent components of the measured magnetic field to eight. An artificial neural network with one hidden layer may then be used to fit this function, in some embodiments, due to the simplicity of the calculations once the network is trained using the theoretical forward model. Assuming an accuracy of 1 µT for the sensors, the orientation of the femoral head component 600 may be found with an accuracy of 0.2 degrees.

In addition to the orientation of the permanent magnet 602, the neural network may be trained to output the exact offset of the permanent magnet 602 with respect to the origin. This value may be used to make sure the femoral head component 600 is not dislocated out of the socket. A system consisting, for example, of only one magnetic sensor may measure only three components of the magnetic field, which reduces to only two independent values once the measurements are normalized. Therefore, such a system may not identify whether the femoral head component is in full contact with the acetabular liner component.

Figure 7A:
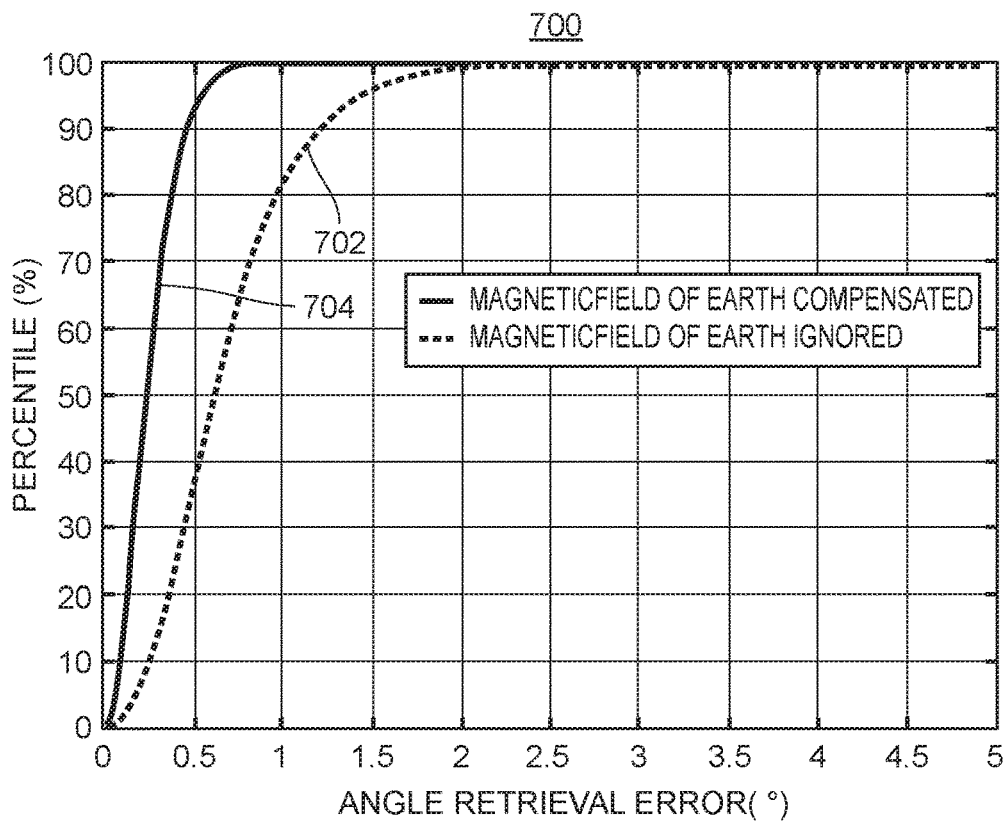
FIGS. 7A and 7B are plots showing the error of the present system when compensating for the magnetic field of the earth, and when using three magnetic sensors, respectively.
Figure 7B:
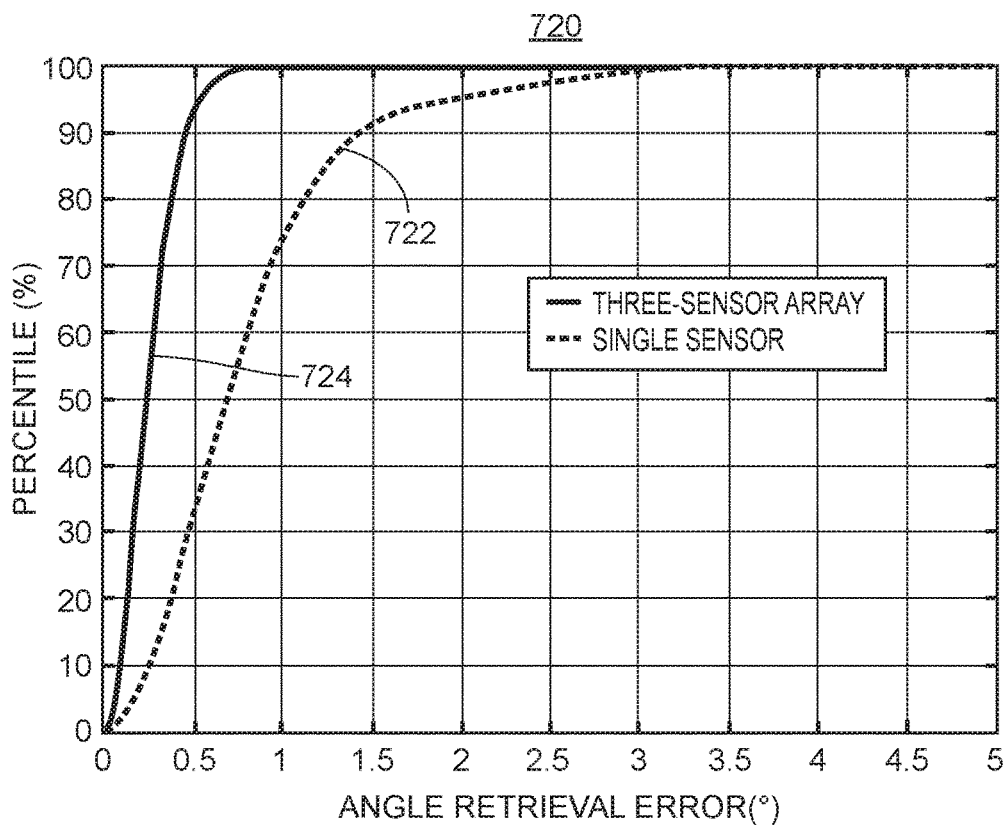

Fabrication tolerances regarding an offset of the permanent magnet 602 with respect to the center of the femoral head component 600 may adversely affect the accuracy of the angle retrieval algorithm, as is discussed in reference to FIGS. 7A and 7B. FIGS. 7A and 7B are plots 700, 702 showing the error of the present system when compensating or not compensating for the magnetic field of the Earth, and when using one or three magnetic sensors, respectively. The first plot 700 of FIG. 7A includes a trace 702 corresponding to an embodiment in which the magnetic field of the Earth is ignored, and a trace 704 corresponding to an embodiment that compensates for the magnetic field of the Earth. The trace 704 may, for example, represent the angle retrieval error of the present system when compensating for the magnetic field of the Earth. Conversely, the trace 702 may, for example, represent the angle retrieval error of the present system when not compensating for the magnetic field of the Earth.

The second plot 720 of FIG. 7B includes a trace 722 corresponding to a design that includes only a single sensor, and a trace 724 corresponding to an embodiment of the present disclosure that uses three sensors. The race 724 may, for example, represent the angle retrieval error of the present system when using a three magnetic sensor array to detect a position of a permanent magnet. Conversely, the trace 722 may, for example, represent the angle retrieval error when using a single magnetic sensor to detect a position of a permanent magnet.

To illustrate, a main source of interference that needs to be mitigated may be the magnetic field of the Earth. The magnetic flux density of the Earth may range between 35 µT to 65 µT, and is therefore much less than that of a permanent magnet (e.g., magnet 602) embedded in a femoral head component (e.g., femoral head component 316), which may be on the order of 10 mT, for example. However, the flux density of the Earth may be much greater than the resolution of the sensors (1 µT), and may thus reduce the sensor accuracy.

The magnetic field of the Earth may be compensated for by using the sensor data just before the femoral head component (e.g., femoral head component 316 or 600) is placed in an acetabular liner component (e.g., acetabular liner component 302 or 500). In the absence of the permanent magnet embedded in the femoral head component, the magnetic sensor readings may be primarily due to the magnetic field of the Earth. Consequently, these readings may be used to measure the orientation and intensity of the magnetic field of the Earth, and completely offset its effects on subsequent measurements. These measurements may be automatically repeated every time the femoral head component is removed to adjust the position of the acetabular liner component.

Noise analysis may be performed by assuming a Gaussian noise with an amplitude of 10 µT. The amplitude may be chosen to be 10 times the resolution of the sensors, for example, as a worst case scenario. A Monte Carlo simulation may then be performed to analyze the behavior of the system in the presence of this noise. The percentile error is shown in FIG. 7A with (i.e., trace 704) and without (i.e., trace 702) compensating for the magnetic field of the Earth. As shown, if the magnetic field of the Earth is properly compensated for, an accuracy of better than 1 degree may be achieved with more than 90% of the cases showing less than 0.5 degree error. These values may increase to 2.5 degrees and 1.5 degrees, respectively, if the magnetic field of the Earth is ignored.

In addition to estimating the angle of the permanent magnet, the neural network may, for example, estimate the permanent magnet location with respect to the axis of rotation of the joint. This information can be used to determine whether the femoral head component and the acetabular liner component are in full contact. Moreover, the angle retrieval may still be accurate even if the location of the permanent magnet (with respect to the axis of rotation of the joint) changes due to fabrication inaccuracies.

FIG. 7B compares the performance of a single-sensor system (i.e., trace 722) to a three-sensor system (i.e., trace 724). The magnetic field of the Earth is compensated for in both trace 722 and trace 724, and the magnetic noise and inaccuracy in positioning the permanent magnet is also the same for both trace 722 and trace 724. As shown in FIG. 7B, the three-sensor system can be roughly three times more accurate than the single-sensor system.

Figure 8:
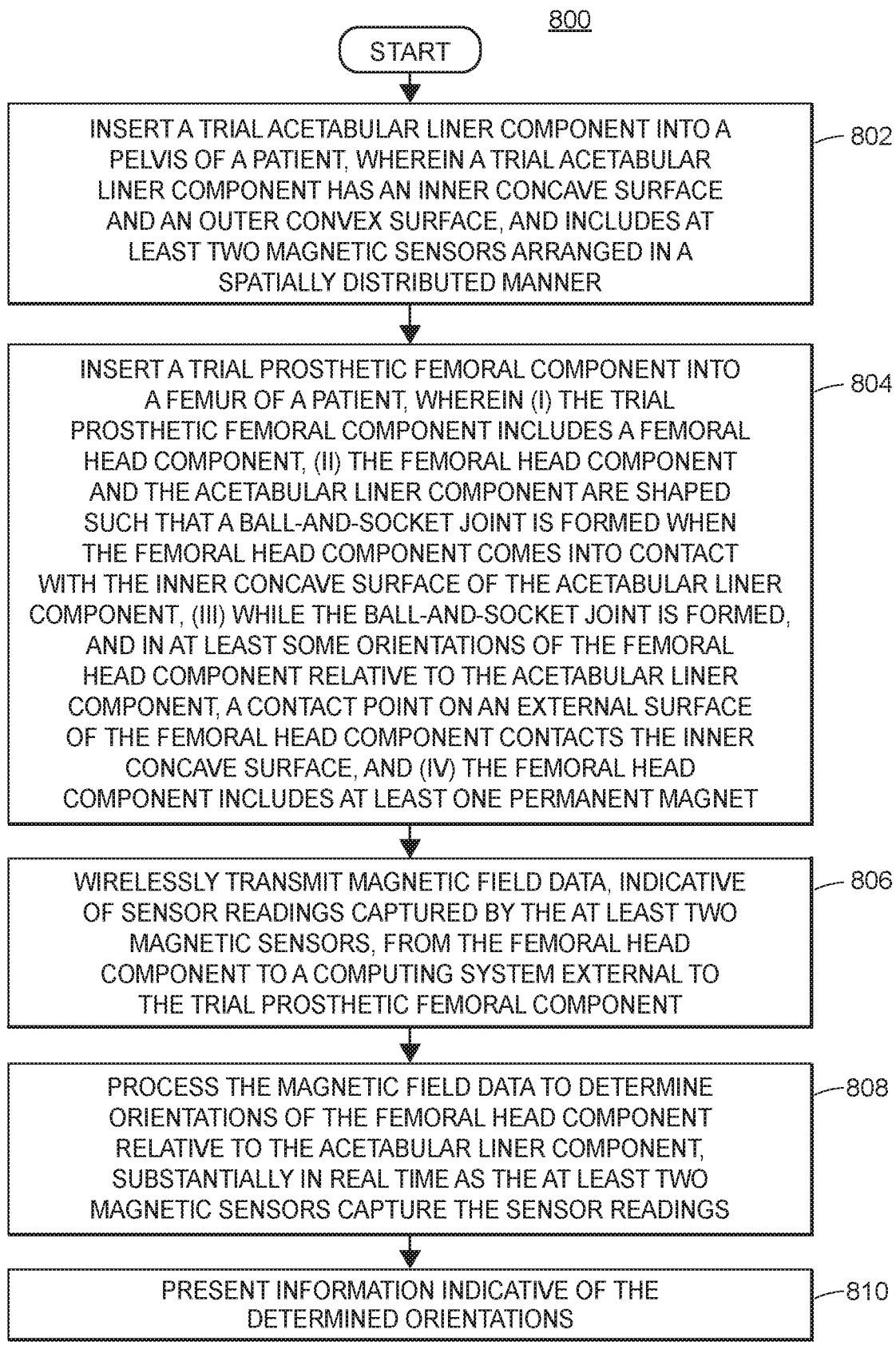
FIG. 8 is a flowchart depicting an example method corresponding to the first aspect of the present disclosure.

FIG. 8 is a flowchart depicting an example method 800 corresponding to the first aspect of the present disclosure. The method 800 may be performed in part by a person (e.g., surgeon), and in part by components of a system (e.g., system 300).

The method 800 begins at block 802, wherein a trial acetabular liner component (e.g., acetabular liner component 302 or 500) is inserted into a pelvis of a patient. The trial acetabular liner component may have an inner concave surface (e.g., inner concave surface 508) and an outer convex surface (e.g., outer convex surface 510), and may include at least two magnetic sensors (e.g., magnetic sensors 308 or 502) arranged in a spatially distributed manner. Block 802 may be performed by a surgeon, for example.

At block 804, the method 800 may include inserting a trial prosthetic femoral component (e.g., prosthetic femoral component 304) into a femur of the patient. Moreover, the trial prosthetic femoral component may include a femoral head component (e.g., femoral head component 316 or 600), and the femoral head component and the acetabular liner component may be shaped such that a ball-and-socket joint is formed when the femoral head component comes into contact with the inner concave surface of the acetabular liner component. While the ball-and-socket joint is formed, and in at least some orientations of the femoral head component relative to the acetabular liner component, a contact point on an external surface of the femoral head component may contact the inner concave surface, and the femoral head component may include at least one permanent magnet (e.g., permanent magnet 322, 406, or 602). Block 804 may be performed by a surgeon, for example.

At block 806, the method 800 may further include wirelessly transmitting magnetic field data, indicative of sensor readings captured by the at least two magnetic sensors, from the femoral head component to a computing system (e.g., computer system 306) external to the trial prosthetic femoral component. Block 806 may be performed by the wireless transceiver 312, for example.

At block 808, the method 800 may further include processing the magnetic field data to determine orientations of the femoral head component relative to the acetabular liner component, substantially in real time as the at least two magnetic sensors capture the sensor readings. This processing may be performed by, for example, the computing system 306 (e.g., processor 326). However, it should be understood that the processing may be accomplished by any suitable device, including internal devices of the trial prosthetic femoral component.

At block 810, the method 800 may further include presenting information indicative of the determined orientations. This information may be determined by, for example, the computing system 306 or any other suitable device contained either internally or externally to the trial prosthetic femoral component. The presentation may be performed by, for example, computer system 306 presenting the determined orientations on a display (e.g., display 328).

In various embodiments, presenting the information indicative of the determined orientations may further include generating, based on the determined orientations, data representing a path of the contact point relative to the acetabular liner component. Additionally, the presenting step may further include presenting on the display a visual representation of the path of the contact point, substantially in real time as the at least two magnetic sensors capture the sensor readings.

In these embodiments, the method 800 may further include generating a visual representation of a safe zone, the safe zone indicating a positioning of the point on the external surface of the femoral head component, relative to the acetabular liner component, that is not expected to result in hip dislocation. This safe zone (possibly including multiple "sub-zones" relating to different risk levels) may then be presented on the display in conjunction with the displayed visual representation of the path. These steps may be performed by, for example, the computing system 306 or any other suitable device contained either internally or externally to the trial prosthetic femoral component.

Further in these embodiments, the method 800 may include generating one or both of (i) an audible alarm, or (ii) a visual alarm, either when the visual representation of the path comes within a threshold distance of a perimeter of the visual representation of the safe zone, or when the visual representation of the path goes outside of the perimeter of the visual representation of the safe zone. This step may be performed by, for example, the computing system 306 or any other suitable device contained either internally or externally to the trial prosthetic femoral component.

Still further in these embodiments, the safe zone may be specific to a patient for which the hip arthroplasty procedure is being performed. Moreover, the safe zone may be specific to at least (i) a height of the patient, and (ii) one or more distances between one or more portions of a pelvis of the patient and one or more portions of a femur of the patient, as measured while the patient is in one or more different poses.

In any of the preceding embodiments related to FIG. 8, determining the orientations of the femoral head component relative to the acetabular liner component may include using the magnetic field data to determine projections of the contact point onto the inner concave surface. Further, determining the orientations of the femoral head component relative to the acetabular liner component may include inputting the magnetic field data, or data derived from the magnetic field data, to a trained neural network. The trained neural network may then output data indicative of the orientations of the femoral head component relative to the acetabular liner component.

In various other embodiments, the method 800 may further include determining one or more ambient magnetic fields that are measured by the at least two magnetic sensors while the ball-and-socket joint is not formed. Next, the method 800 may determine at least one magnetic field calibration factor based on the one or more ambient magnetic fields. Finally, the method 800 may additionally determine the orientations of the femoral head component relative to the acetabular liner component based on the magnetic field data and the at least one magnetic field calibration factor.

Turning now to the second aspect of the present disclosure, another high-accuracy positioning measurement system is proposed. Generally speaking, the system uses a high-resolution microscopic imaging system with an associated lighting system and wireless transmitter, which may all be embedded in the femoral head component. An acetabular liner component may have patterned surfaces that include fine resolution geometric codes that may be color-coded, and uniquely specify the location of the center of the femoral head component on the surface of the acetabular liner component.

The system may be used, for example, to execute a positioning algorithm also described herein. The positioning algorithm may be computer aided and may include using optical images wirelessly sent by the imaging system to identify the location of the center of the femoral head component. The images may then be interpreted and streamed to a display that may be viewed by a surgeon during a procedure, as discussed further below.

Figure 9A:
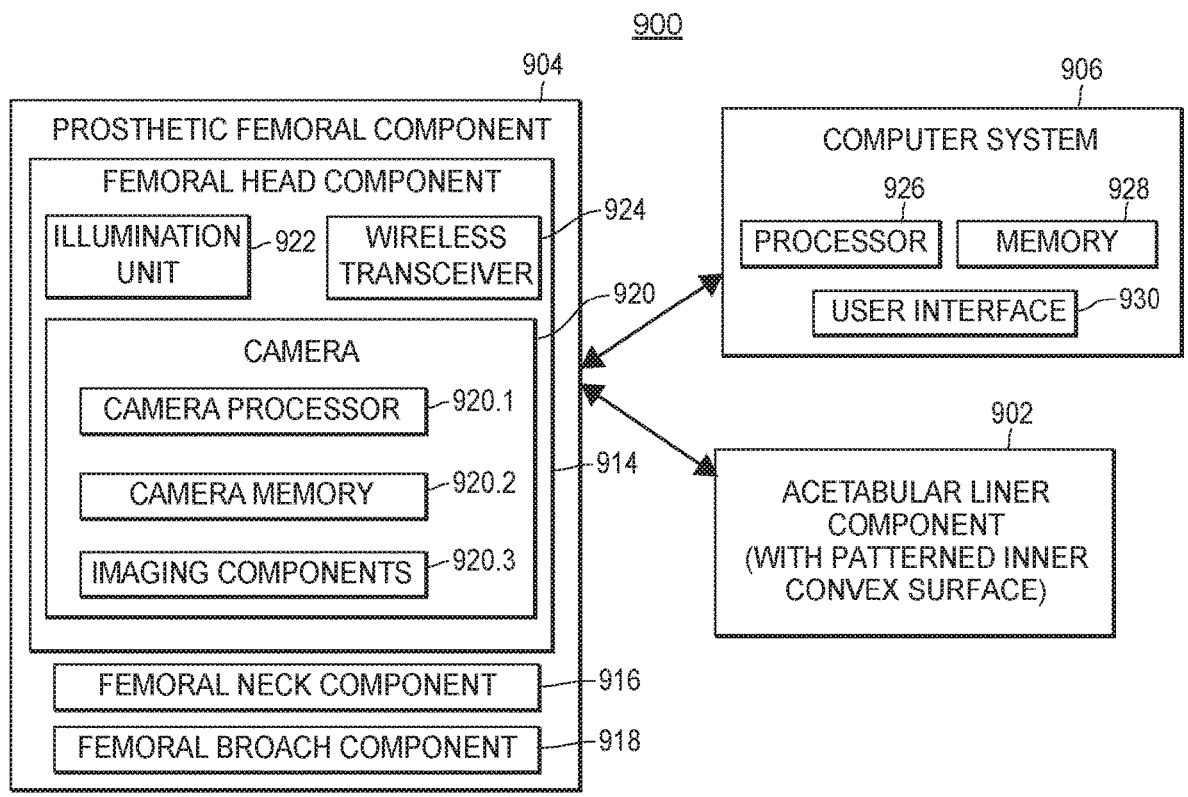
FIGS. 9A and 9B depict another example system for aligning hip replacement prostheses, in accordance with a second aspect of the present disclosure that utilizes a camera.
Figure 9B:
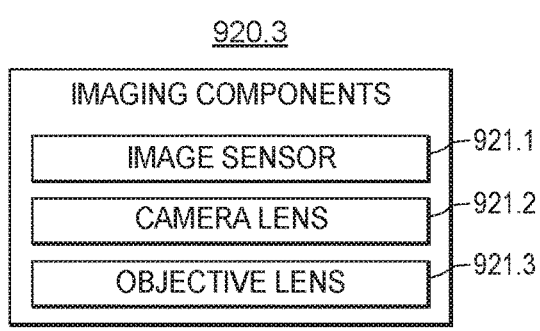

FIGS. 9A and 9B depict another example system for aligning hip replacement prostheses, in accordance with the second aspect of the present disclosure that utilizes a camera. As shown in FIG. 9A, the system 900 may include an acetabular liner component 902, a prosthetic femoral component 904, and a computer system 906. The acetabular liner component 902 may further include an inner concave surface, and an outer convex surface. The inner concave surface may include a patterned imaging surface. The patterned imaging surface may include various patterns, symbols, etchings, or other suitable indications. In various embodiments, the acetabular liner component 902 comprises a polyurethane cup, or any other material or a combination of materials. Additionally, in certain embodiments, the acetabular liner component 902 includes a plurality of pressure sensors arranged along an outer perimeter of the inner concave surface.

In some embodiments, the inner concave surface is visually coded with a plurality of liner "pixels." In some embodiments, each pixel may uniquely specify a position on the inner concave surface by way of including either (i) a different color, or (ii) a different combination and/or arrangement of two or more colors. To illustrate, and as further discussed herein, each pixel may include a different shade of a particular color (e.g., shades of blue, green, etc.), and/or each pixel may include combinations of white, blue, green, red, or any other color.

The prosthetic femoral component 904 may include a femoral head component 914, a femoral neck component 916, and a femoral broach component 918. The femoral head component 914 and the acetabular liner component 902 may be shaped such that a ball-and-socket joint is formed when the femoral head component 914 comes into contact with the inner concave surface of the acetabular liner component 902. The femoral head component 914 may be configured to physically couple to the femoral neck component 916 in a removable manner (e.g., snap-fit, or screw and threaded hole arrangement, etc.), and the femoral neck component 916 may be configured to physically couple to the femoral broach component 918 in a removable manner (e.g., snap-fit, or screw and threaded hole arrangement, etc.).

Further, the femoral head component 914 may comprise a microscopic color detecting system 920 (also referenced herein as a "camera"), an illumination unit 922, and a wireless transceiver 924. The camera 920 is embedded in the femoral head component 914 and is configured to capture images that, while the ball-and-socket joint is formed, are sized so as to each contain at least one pixel of the plurality of liner pixels. The camera 920 may further include a camera processor 920.1, a camera memory 920.2, and imaging components 920.3. The camera 920 may be any suitable imaging system.

In some implementations, the camera 920 is configured to capture color-coded images that are each sized so as to each contain an entirety of no more than a single pixel of the plurality of liner pixels at any given time (e.g., one full pixel and no more than 10% of any surrounding pixel, etc.).

In various embodiments, and as shown in FIG. 9B, the imaging components 920.3 of the camera 920 include an image sensor 921.1 (e.g., a charge-coupled device (CCD) sensor), a camera lens 921.2, and an objective lens 921.3. The camera lens 921.2 and the objective lens 921.3 may be cumulatively referenced herein as a "lens system". As further discussed below in reference to FIGS. 10 and 11, the camera lens 921.2 may be situated between the image sensor 921.1 and the objective lens 921.3. In various embodiments, the camera lens has a focal length between 1.8 and 7.2 millimeters, and the objective lens has a focal length between 0.6 and 2.4 millimeters.

In some embodiments, the image sensor 921.1 includes a plurality of image sensor pixels arranged in a two-dimensional array. Here, the image sensor 921.1 may include fewer than 300,000 image sensor pixels. Further, in some embodiments, the size of each of the plurality of image sensor pixels, the size of each of the plurality of liner pixels, and a magnification ratio of the lens system are collectively configured to provide a resolution of 3 degrees or finer in positioning of the femoral head component 914 relative to the acetabular liner component 902. Alternatively, the size of each of the plurality of image sensor pixels, the size of each of the plurality of liner pixels, and the magnification ratio of the lens system may be collectively configured to provide a resolution of 1 degree or finer in positioning of the femoral head component 914 relative to the acetabular liner component 902.

To achieve the resolution provided in the previous embodiments, the dimensions of the image sensor pixels as well as the magnification ratio of the lens system may have certain constraints. For example, in certain embodiments, each image sensor pixel has a largest dimension of less than 5 micrometers, and the lens system may provide a magnification ratio between 2:1 and 5:1. Additionally, the lens system may be configured to focus, while the ball-and-socket joint is formed, on a single pixel of the plurality of liner pixels at any given time.

Additionally, each pixel of the liner pixels may uniquely specify a position on the inner concave surface by way of including either (i) a different color that does not contain any element of red in a red-green-blue (RGB) color model, or (ii) a different combination and/or arrangement of two or more colors that each do not contain any element of red in the RGB color model.

In some implementations, each pixel of the plurality of liner pixels uniquely specifies a position on the inner concave surface by way of including a different color, and the inner concave surface is further visually coded with a plurality of white pixels. The white pixels may be interspersed among the other pixels (e.g., as discussed below with reference to FIGS. 12 and 13). Moreover, the white pixels may be used, for example, to calibrate the camera 920.

As noted above, each of the liner pixels may uniquely specify a position on the inner concave surface by way of including a different combination and/or arrangement of two or more colors. The two or more colors may include a respective plurality of sub-pixels (e.g., four sub-pixels), with at least one of the respective plurality of sub-pixels being white (e.g., as discussed below with reference to FIG. 13). Each set of sub-pixels within a given pixel may include at least two geometric shapes, with at least one of the geometric shapes being colored and at least one of the geometric shapes being white. The geometric shapes may be squares, with each set of sub-pixels within a given pixel including four squares (e.g., with three sub-pixels being colored and one sub-pixel being white). If the geometric shapes are squares, with four squares per pixel, each square of each sub-pixel may be between 50 and 150 micrometers in width, for example. However, the geometric shapes may be any suitable shape of any suitable dimensions.

As was also noted above, each of the liner pixels may uniquely specify a position on the inner concave surface by way of including a different combination and arrangement of two or more colors. The combination and arrangement of two or more colors in the liner pixels may be arranged according to a reflected binary code (RBC) representation, for example.

When each of the liner pixels uniquely specifies a position on the inner concave surface by including a different combination and arrangement of two or more colors, in certain embodiments, the combination and arrangement may be unique relative to the combination and arrangement in every other pixel of the liner pixels. This may be true irrespective of whether any of the liner pixels is rotated about its center point.

To achieve the various color combinations described herein, a variety of colors are included in each of the plurality of liner pixels. For example, in various embodiments, the plurality of liner pixels includes less than 300 different colors. Alternatively, the plurality of liner pixels may include less than 70 different colors.

In certain embodiments, each of the liner pixels is immediately adjacent to at least one other pixel of the liner pixels. Moreover, in some embodiments, the liner pixels may cover at least 80% of the inner concave surface, or another suitable percentage of the inner concave surface. Generally, the liner pixels may cover any percentage or amount of the inner concave surface that is necessary or desired to achieve the results and advantages described herein. Accordingly, the liner pixels may cover substantially an entirety of the inner concave surface.

To provide substantial coverage of the inner concave surface, a significant number of liner pixels are required. Thus, in certain embodiments, the inner concave surface is covered with at least 1,000 pixels, with each pixel having a longest dimension, along the inner concave surface, of less than 500 micrometers. The longest dimension may be between 150 and 250 micrometers, for example.

In various embodiments, the acetabular liner component 902, and/or the femoral head component 914, comprise the illumination unit 922. The illumination unit 922 may be configured to illuminate at least a portion of the inner concave surface while the ball-and-socket joint is formed. The illumination unit 922 may include an LED array, for example. The LED array may be embedded in the acetabular liner component 902 and/or the femoral head component 914.

The wireless transceiver 924 may include one or more antennas and a radio frequency (RF) module (not shown). The antenna and RF module may be designed to have a low power consumption of 25 mW to allow for extended use without the need to change or charge a battery.

The wireless transceiver 924 may be configured to transmit images captured by the image sensor 921.1 to the computer system 906, external to the prosthetic femoral component 904. In certain embodiments, the wireless transceiver 924 may transmit images captured by the image sensor 921.1 to the destination external to the prosthetic femoral component 904 using a Bluetooth communication protocol. However, the wireless transceiver 924 may use any suitable communication protocol (e.g. Wifi, LPWAN, etc.).

Further, in these embodiments, the prosthetic femoral component 904 may include a battery (not shown) that is entirely embedded within the femoral head component 914 and electrically coupled to the wireless transceiver 924. In these and other embodiments, the wireless transceiver 924 may be configured to transmit the images captured by the image sensor 921.1 to the destination external to the prosthetic femoral component 904 at a rate of at least 30 frames per second. The wireless transceiver 924 may be further configured to transmit the images substantially in real time as the images are captured by the image sensor 921.1.

The computer system 906 may include a processor 926, a memory 928, and a user interface 930 (also referenced herein as a "display"). While referred to herein as a single "processor," in some embodiments processor 926 includes two or more processors. In various embodiments, the memory 928 (e.g., a solid state memory, hard drive, or other suitable memory) may store instructions that, when executed by the processor 926 (e.g., one or more microprocessors), cause the computer system 906 to (i) receive the images transmitted by the wireless transceiver 924, (ii) for each received image, process the received image to identify a corresponding pixel of the plurality of liner pixels, and a position corresponding to that pixel, and (iii) based on a plurality of the identified pixels/positions, generate data representing a path of at least a portion of the femoral head component 914 relative to the acetabular liner component 902. While not shown in FIG. 9A, the computer system 906 also includes, or is coupled to, a wireless transceiver to allow communication with the prosthetic femoral component 904 using the Bluetooth or other protocol. Moreover, the instructions may further cause the computer system 906 to generate data representing a path of a contact (e.g., center) point on an external surface of the femoral head component 914 relative to the acetabular liner component 902.

Additionally, the instructions may cause the computer system 906 to present to a user, on the display 930, a visual representation of the path of the contact point relative to the acetabular liner component 902. This presentation may be performed substantially in real time as the images are captured by the image sensor 921.1, after the images have all been captured, or at any point in between.

In these embodiments, the instructions cause the computer system 906 to generate a visual representation of a "safe zone." The safe zone may represent an area of the inner convex surface of the acetabular liner component 902 that, if not exited by the contact point, should not cause hip dislocation to occur. Once the safe zone is generated, the instructions may further cause the computer system 906 to present the safe zone on the display 930 in conjunction with the displayed visual representation of the path.

The instructions may cause the computer system 906 to generate one or both of (i) an audible alarm, or (ii) a visual alarm, in certain situations. In particular, these alarm(s) may be generated when the visual representation of the path comes within a threshold distance of a perimeter of the visual representation of the safe zone, and/or when the visual representation of the path goes outside of the perimeter of the visual representation of the safe zone.

In these embodiments, the safe zone may be specific to a patient for which the hip arthroplasty procedure is being performed. Namely, the safe zone may be specific to at least (i) a height of the patient, and (ii) one or more distances between one or more portions of a pelvis of the patient and one or more portions of a femur of the patient, as measured while the patient is in one or more different poses.

In embodiments where the acetabular liner component 902 includes a plurality of pressure sensors arranged along an outer perimeter of the inner concave surface, the instructions may cause the computer system 906 to monitor pressure measurements of the one or more pressure sensors. Based on the monitored pressure measurements, the instructions may cause the computer system 906 to generate an audio or visual indication of when a surface of the acetabular liner component 902 is impinging upon the acetabular liner component 902 (e.g., when at least one of the pressure sensors senses a pressure above some threshold value).

In any of the preceding embodiments related to FIG. 9A or 9B, and as further discussed below in reference to FIG. 13, the instructions may further cause the computer system 906 to identify the corresponding pixel of the plurality of liner pixels by detecting a combination and arrangement of colors within the corresponding pixel. Namely, in various embodiments, the instructions may cause the computer system 906 to identify the corresponding pixel by measuring a blue value and a green value for each of one or more sub-pixels within the corresponding pixel.

Additionally, in certain embodiments, the instructions may cause the computer system 906 to, for at least some of the received images, (i) determine at least one color calibration factor based on a white area within the corresponding pixel, and (ii) identify the corresponding pixel in part by applying the determined one color calibration factor(s) to one or more colors detected within the corresponding pixel.

In various embodiments, the acetabular liner component 902 and the prosthetic femoral component 904 may be trial components to be removed prior to completion of the hip arthroplasty procedure.

Figure 10:
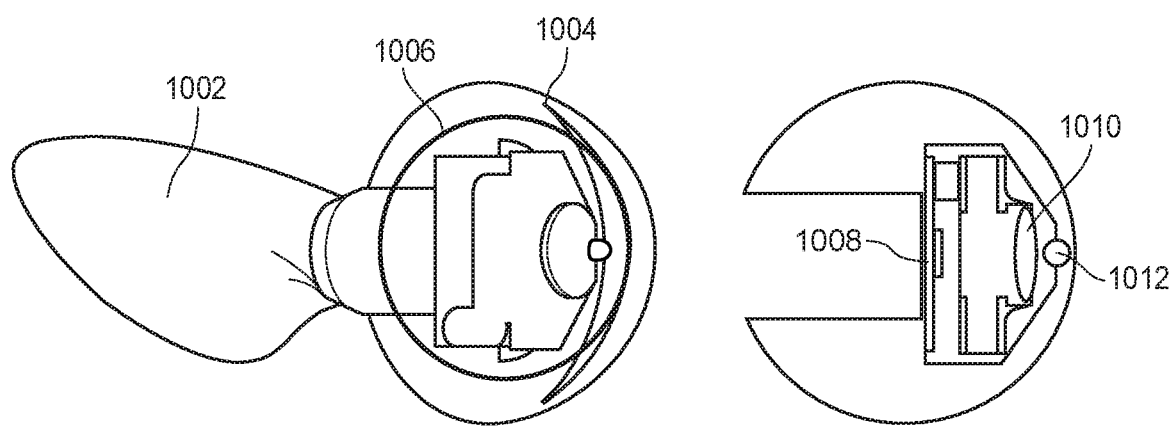
FIG. 10 provides a side view and cutaway view of a femoral head component containing an embedded imaging system in accordance with the second aspect of the present disclosure.

FIG. 10 provides a side view of a prosthetic femoral component (e.g., prosthetic femoral component 904) containing an embedded imaging system 1006 (e.g., camera 920) in accordance with the second aspect of the present disclosure. As shown in the side view of FIG. 10, the embedded imaging system 1006 may be within a femoral head component 1004 (e.g., femoral head component 914) coupled to a femoral neck component 1002 (e.g., femoral neck component 916).

As shown in the cutaway view of the embedded imaging system 1006, the imaging system 1006 may include an image sensor 1008, a camera lens 1010, and an objective lens 1012 (e.g., components 921.1, 921.2, and 921.3, respectively, of FIG. 9B). These components allow the embedded imaging system 1006 to focus on a very small area on the color-coded acetabular liner component (e.g., acetabular liner component 902).

The image sensor 1008 may be a low-power CCD sensor with about 600 by 460 pixels or less, for example. The physical size of each pixel on the sensor may be 2.5 µm per side (for a square shape), but may also be any suitable size. Because of the small space available within the femoral head component 1004, the objective lens 1012 may have an extremely small focal length. The focal length may be particularly small because the object to be imaged (i.e., the acetabular liner component 902) is placed very close to the embedded imaging system 1006. Hence, the camera lens 1010 may have a focal length of approximately f1=3.6 mm and the objective lens 1012 may have a focal length of approximately f2=1.2 mm, resulting in a 3 to 1 magnification ratio.

Therefore, a 200 µm by 200 µm pixel on the femoral head component 1004 may occupy a 240 pixel by 240 pixel area on the CCD sensor, which may simplify the reading and decoding process. This pixel size may allow for better than 1 degree resolution in positioning the femoral head component 1004.

Figure 11:
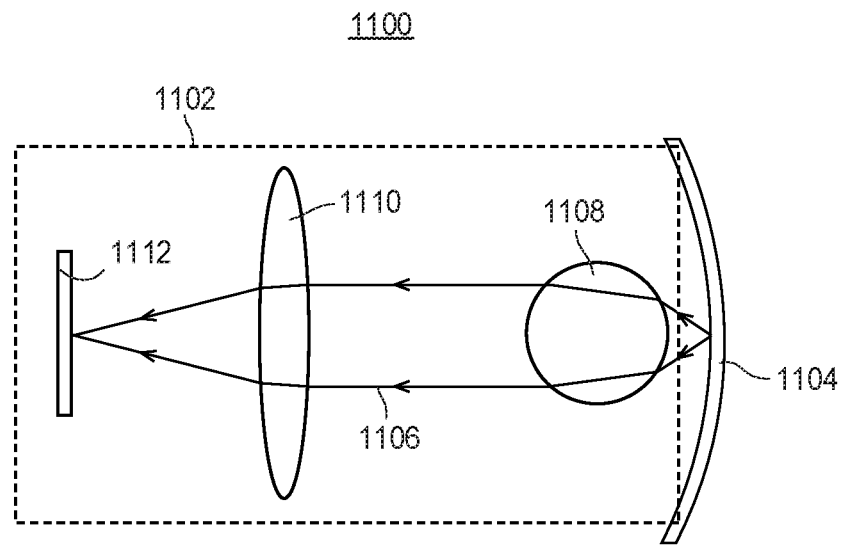
FIG. 11 illustrates the operation of various imaging components within the system of FIGS. 9A and 9B.

FIG. 11 illustrates the operation of various imaging components 1100 within the system 900 of FIGS. 9A and 9B. The imaging components 1100 include an imaging system 1102, an inner concave surface 1104 of an acetabular liner component (e.g., acetabular liner component 902), and an image path 1106. The imaging system 1102 consists of an objective lens 1108 (e.g., objective lens 921.3), a camera lens 1110 (e.g., camera lens 921.2), and an image sensor 1112 (e.g., image sensor 921.1). The inner concave surface 1104 of the acetabular liner component may include various color coded patterns, as discussed above. FIG. 11 depicts an optical path 1106 showing how light may travel between a particular color coded pixel on the inner concave surface 1104 and the image sensor 1112.

The inner concave surface 1104 may be patterned in such a way as to present a unique color to the imaging system 1102 (i.e., a unique mixture of RGB components) at a resolution better than 200 µm in each direction, for example. The objective lens 1108 helps focus the viewing angle of the imaging system 1102 to an extremely small (e.g., 200 µm by 200 µm) pixel on the inner concave surface 1104. The intensity of red, green, and blue light coming from each pixel may then be detected by the image sensor 1112 that is placed on the focal plane of the camera lens 1110. This color-specific intensity information may then be used to determine the position of the femoral head component 1004 (e.g., the center point thereof) with respect to the inner concave surface 1104.

Thus, the output of the image sensor 1112 may be used to map the unique position identified by the RGB components. This approach can avoid the complicated and time-consuming image processing that may otherwise be needed to recognize complex geometries and conduct comparisons with known templates. The imaging system 1102 may focus on only one pixel, making high-resolution CCD cameras unnecessary. This may significantly reduce the data rate and the required processing time/power.

Figure 12:
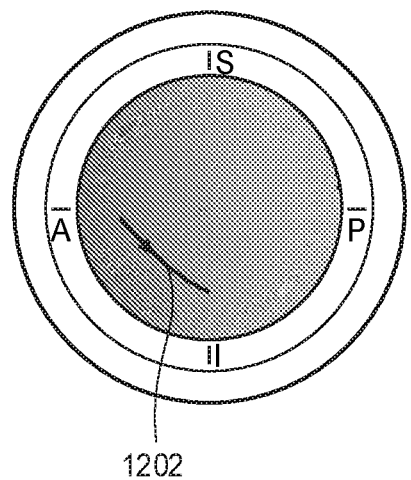
FIG. 12 depicts an example camera path for the camera of FIG. 9A.

FIG. 12 depicts an example camera path 1202 for the camera 920 of FIG. 9A. The example path 1202 may equivalently represent a path of the center of a femoral head component (e.g., femoral head component 914 or 1004) across an inner concave surface (e.g., inner concave surface 1104) of an acetabular liner component (e.g., acetabular liner component 902). That is, the camera 920 may capture images of the surface of the inner concave surface as the center of the femoral head component travels along the example path 1202, e.g., to generate video or stream real-time images of the inner concave surface.

Figure 13:
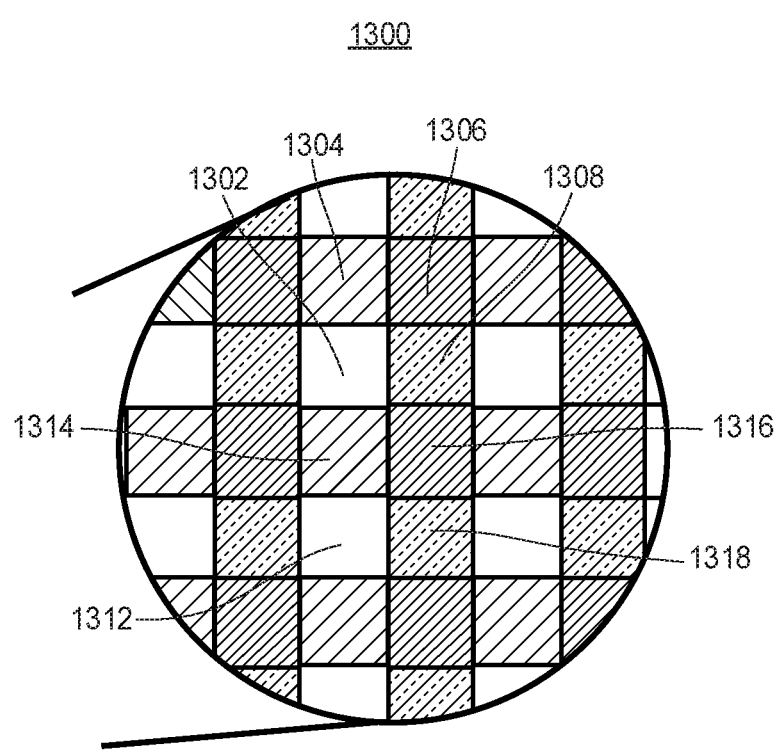
FIG. 13 depicts an example image of a pattern on the surface of an acetabular liner component captured by the camera of FIG. 9A.

FIG. 13 depicts an example image 1300 of a pattern on a portion of the inner concave surface of an acetabular liner component, as captured by the camera 920, for example. The example image 1300 includes a first sub-pixel 1302, a second sub-pixel 1304, a third sub-pixel 1306, a fourth sub-pixel 1308, a fifth sub-pixel 1312, a sixth sub-pixel 1314, a seventh sub-pixel 1316, and an eighth sub-pixel 1318. A single pixel may be a square shape that includes any four adjacent sub-pixels of the sub-pixels 1302-1318, for example, or any other suitable number of sub-pixels.

As illustrated, the example image 1300 contains a plurality of sub-pixels in addition to the sub-pixels 1302-1308. Hence, the patterning scheme chosen to cover the inner concave surface must be precise enough to allow the system 900 to distinguish between the various sub-pixels represented in any image captured by the image sensor (e.g., image sensor 1112).

For example, one possible patterning scheme may involve color coding various sub-pixels on the inner concave surface. However, it is possible for the inner concave surface to be stained with blood during surgery, which may change the appearance of the colors patterned thereon. Therefore, only (or primarily) blue and green colors may be used to code the position, while a white area may be added to every pixel for calibration purposes. The computer system 906 may use the detected RGB values corresponding to the white area to determine a correction ratio, and apply that correction ratio to identify the true color of each pixel or sub-pixel. The correction ratio may account for any attenuation in green and blue channels as a result of stains, as well as any change in the intensity or color temperature of the light source, for example.

For example, each of the sub-pixels may be printed with any of the unique color values generated by the numerical triplet combinations in the RGB system. Namely, each geometric position on the inner concave surface may correspond to a unique triplet of color values, as illustrated below:

| Green (G) | Blue (B) |
|-----------|----------|
| (0, 1, 0) | (0, 0, 1) |
| (0, 2, 0) | (0, 0, 2) |
| (0, 3, 0) | (0, 0, 3) |
| (0, 4, 0) | (0, 0, 4) |
| . . . | . . . |
| (0, 255, 0) | (0, 0, 255) | and including all of the various permutations and combinations of the color values, as would be understood by one of skill in the art.

In one embodiment, each colored sub-pixel on the polyurethane is approximately 100 μm by 100 μm, and the camera may view four sub-pixels (two in each direction) simultaneously, which would guarantee two colored sub-pixels and two white sub-pixels per pixel when, for example, every other sub-pixel in each direction is white. The camera may have a resolution of 8 bits per color channel, which would allow for more than 65,000 unique colors if the red channel is not used for color coding. This may provide a positioning resolution of better than 1 degree. However, it is possible to achieve the same resolution with fewer colors, which may result in a significant difference between the colors and reduce the positioning error due to printing inaccuracies, imaging noise, insufficient lighting, etc.

To illustrate, the focal point of the camera 920 of FIG. 9A may traverse the example path 1202 of FIG. 12 and capture the example image 1300 at some point along path 1202. In a specific example, the first sub-pixel 1302 may be a white area used for calibration in a pixel that also contains the sub-pixels 1304-1308, which may be colored sub-pixels. The sub-pixels 1304-1308 may each be differently colored and thus yield a 3 bit accuracy in determining whether each color channel (i.e., green or blue) is sufficient to uniquely determine the position of the femoral head component. The system may then use the values detected in the white sub-pixel 1302 to determine a correction ratio to apply to the color(s) detected in the other sub-pixels 1304-1308. Once the correction ratio is applied, the exact color values of the sub-pixels 1304-1308 may be identified. The system may then determine the position of the femoral head component by relating the identified color(s) of the sub-pixels 1304-1308 to a coded geometric position on the inner concave surface.

Therefore, a printer may only be required to produce 65 different colors, including white. The colors may be selected such that the determined position does not change if the camera is rotated around its axis, which means the orientation of the camera may be arbitrary. In addition, a reflected binary code (RBC) representation may be used to code the position. This may ensure the position determination is accurate even if two halves of two adjacent pixels are mistaken for a separate pixel.

In one example, the sub-pixels 1302-1308 comprise a first pixel, and the sub-pixels 1312-1318 comprise a second pixel. In this example, the color values or other suitable values of the first sub-pixel 1302, second sub-pixel 1304, and third sub-pixel 1306 may match the color or other suitable values of the fifth sub-pixel 1312, sixth sub-pixel 1314, and seventh sub-pixel 1316, respectively. However, the color or other suitable value of the fourth sub-pixel 1308 may differ from the value of the eighth sub-pixel 1318. Thus, the system may determine the center of the femoral head component is in the unique position corresponding to a particular pixel (e.g., pixel 1308 or 1318) by identifying the unique composition of color or other suitable values comprising that pixel.

Figure 14:
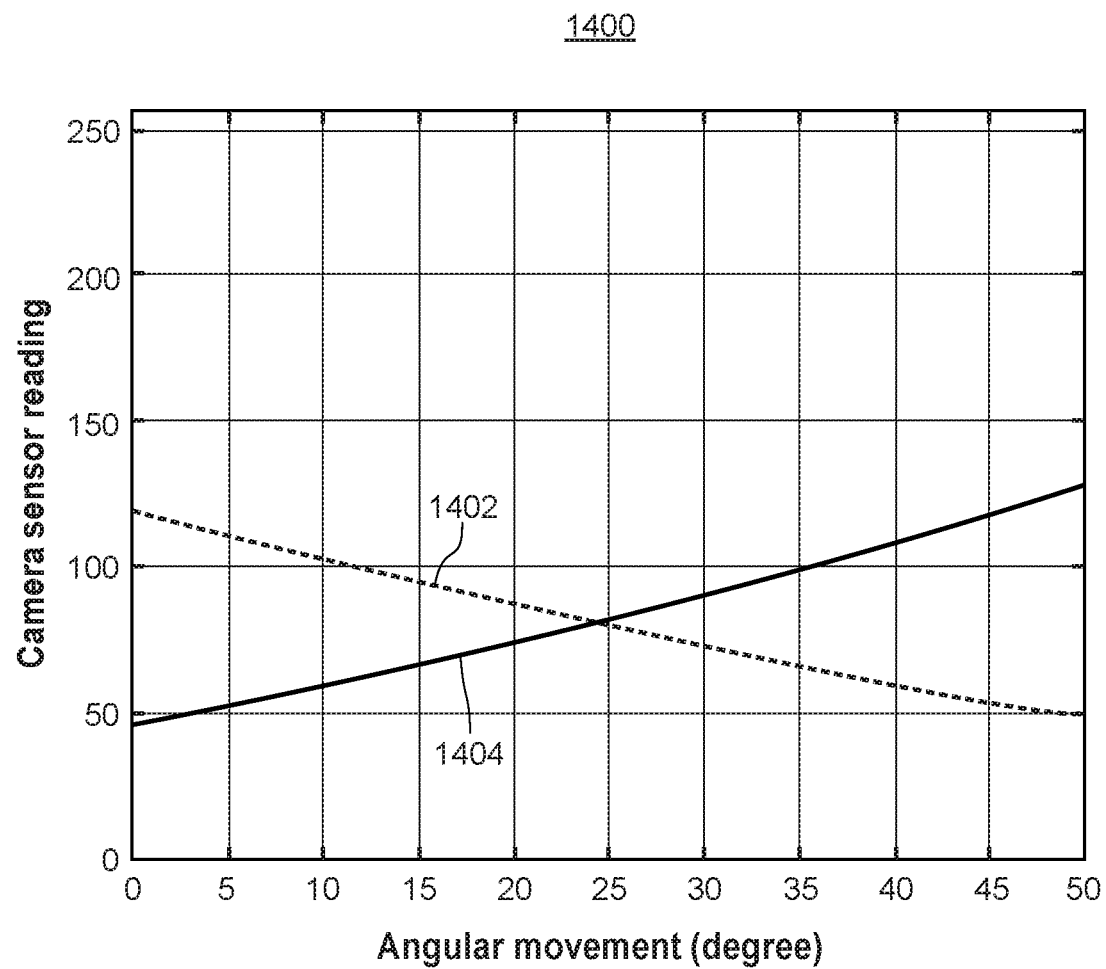
FIG. 14 is a plot showing an image profile, corresponding to a particular image pattern, as observed by the camera of FIG. 9A as the camera moves on an imaging path across an inner concave surface of an acetabular liner component.

FIG. 14 is a plot 1400 showing an image profile, corresponding to a particular image pattern, as observed by the camera 920 of FIG. 9A as the camera 920 moves on an imaging path (e.g., example path 1202) across an inner concave surface (e.g., inner concave surface 1104) of an acetabular liner component (e.g., acetabular liner component 902). As the camera 920 traverses the imaging path, the values represented by the particular patterning scheme covering the inner concave surface may be represented as shown on the plot 1400. The plot 1400 may include a first expressive value 1402, and a second expressive value 1404 (e.g., RGB values between 0 and 255).

For example, where the patterning scheme includes applying varying degrees of blue and green coloration to the individual sub-pixels comprising the pixels covering the inner concave surface, the first expressive value 1402 may represent the detected saturation of the color blue on each sub-pixel as the camera 920 traverses the imaging path. Accordingly, the second expressive value 1404 may represent the detected saturation of the color green on each sub-pixel as the camera 920 traverses the imaging path. Combining these two detected saturation values provides a unique identifier for each individual pixel on the inner concave surface.

Figure 15:
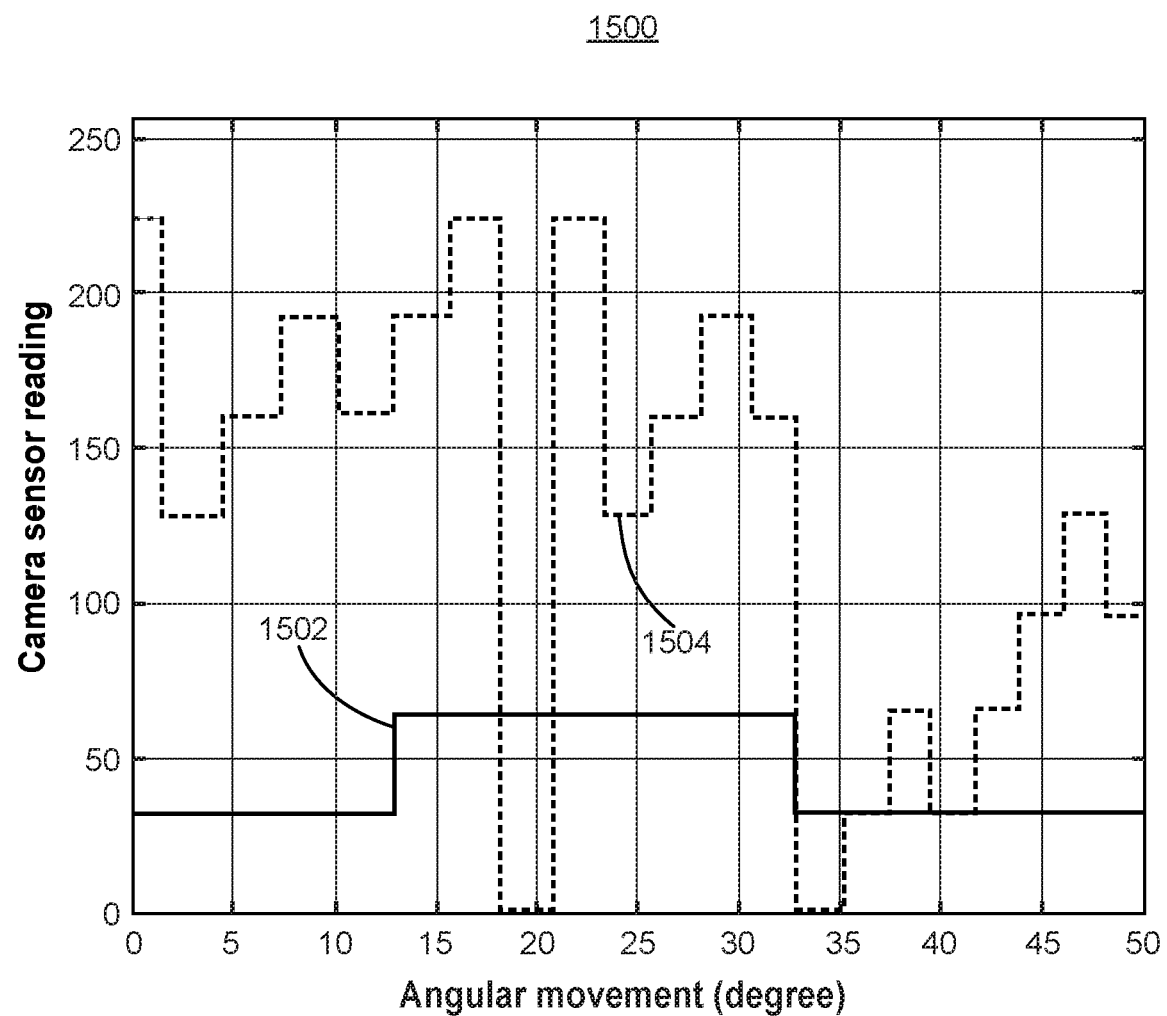
FIG. 15 is a plot showing an image profile, corresponding to another particular image pattern, as observed by the camera of FIG. 9A as the camera moves on an another imaging path across an inner concave surface of an acetabular liner component.

FIG. 15 is a plot 1500 showing an image profile, corresponding to another particular image pattern, as observed by the camera 920 of FIG. 9A as the camera 920 moves on another imaging path (e.g., example path 1202) across an inner concave surface (e.g., inner concave surface 1104) of an acetabular liner component (e.g., acetabular liner component 902). The plot 1500 may include a first expressive value 1502, and a second expressive value 1504 (e.g., RGB values between 0 and 255).

In various embodiments, the first expressive value 1502 represents a saturation value of a unique color patterned on a sub-pixel imaged at a particular location on the inner concave surface. For example, the first expressive value 1502 may represent a saturation value of the color green on the imaged sub-pixel.

Correspondingly, the second expressive value 1504 may represent a saturation value of a another unique color patterned on the sub-pixel imaged at the particular location on the inner concave surface. For example, the second expressive value 1504 may represent a saturation value of the color blue on the imaged sub-pixel. From the information identified via the first expressive value 1502 and the second expressive value 1504, the system may identify the unique position of the femoral head component on the inner concave surface.

Figure 16:
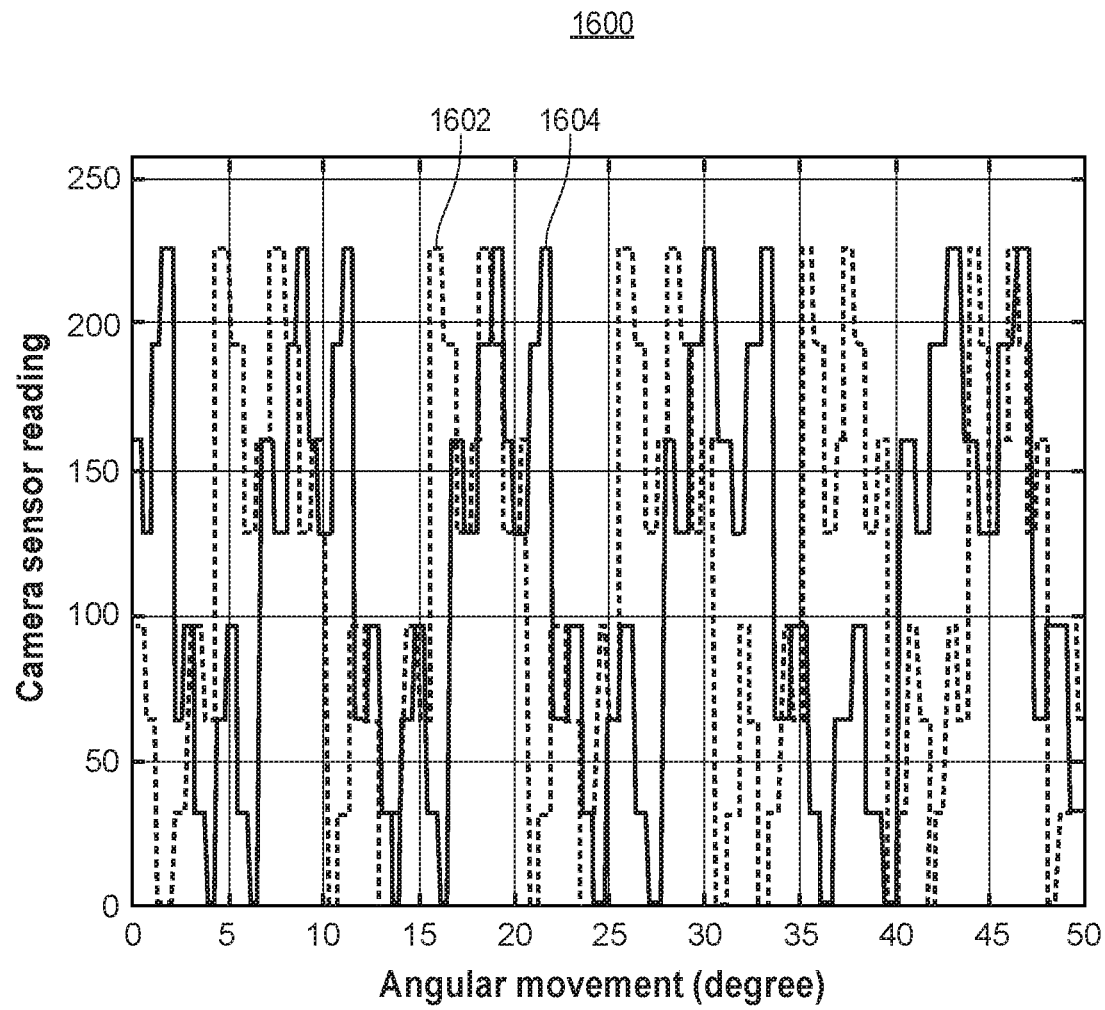
FIG. 16 is a plot showing an image profile, corresponding to yet another particular image pattern, as observed by the camera of FIG. 9A as the camera moves on yet another imaging path across an inner concave surface of an acetabular liner component.

FIG. 16 is a plot 1600 showing an image profile, corresponding to yet another particular image pattern, as observed by the camera 920 of FIG. 9A as the camera 920 moves on yet another imaging path (e.g., example path 1202) across an inner concave surface (e.g., inner concave surface 1104) of an acetabular liner component (e.g., acetabular liner component 902). The plot 1600 may include a first expressive value 1602, and a second expressive value 1604 (e.g., RGB values between 0 and 255).

In various embodiments, the first expressive value 1602 represents a saturation value of a unique color patterned on a sub-pixel imaged at a particular location on the inner concave surface. For example, the first expressive value 1602 may represent a saturation value of the color green on the imaged sub-pixel.

Correspondingly, the second expressive value 1604 may represent a saturation value of a another unique color patterned on the sub-pixel imaged at the particular location on the inner concave surface. For example, the second expressive value 1604 may represent a saturation value of the color blue on the imaged sub-pixel. From the information identified via the first expressive value 1602 and the second expressive value 1604, the system may identify the unique position of the femoral head component on the inner concave surface.

Figure 17:
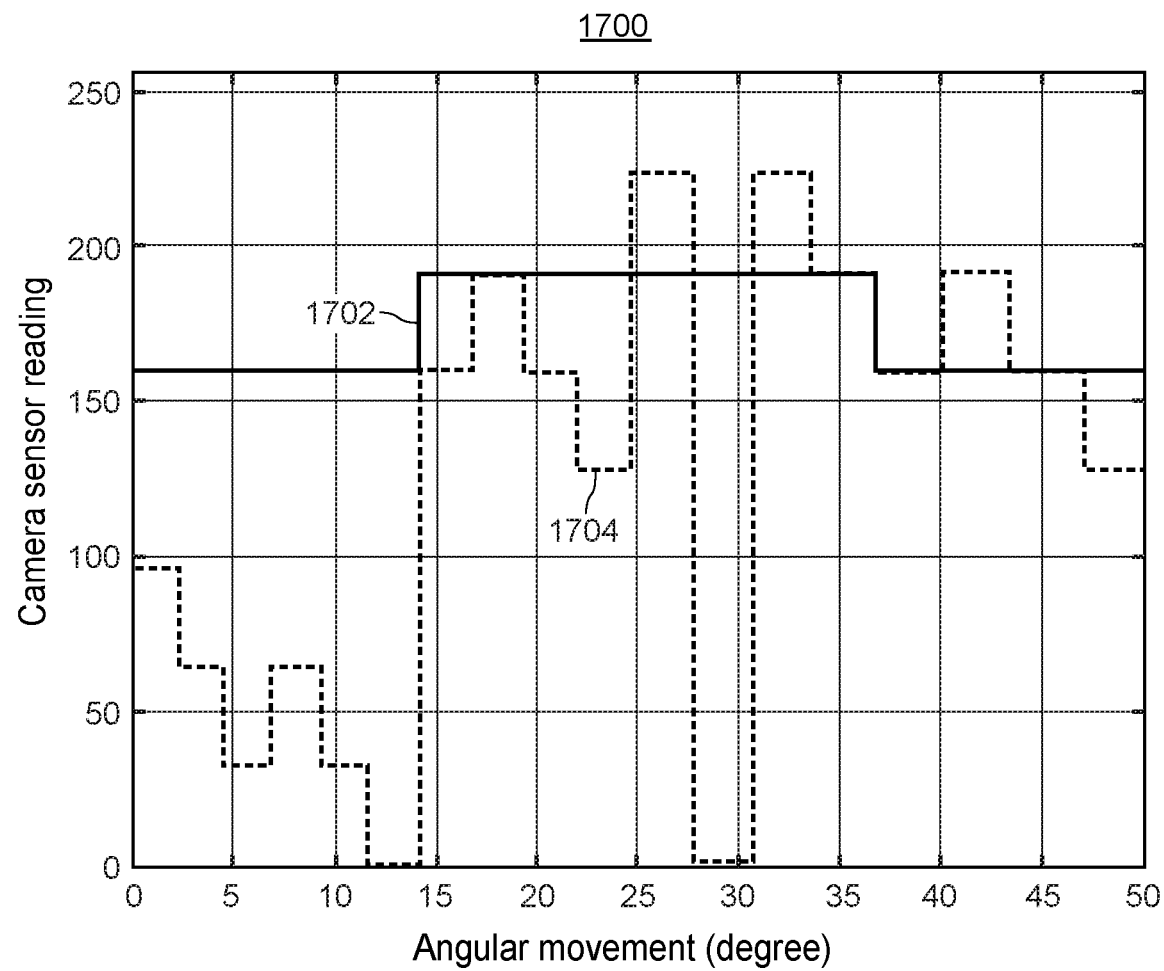
FIG. 17 is a plot showing an image profile, corresponding to still another particular image pattern, as observed by the camera of FIG. 9A as the camera moves on still another imaging path across an inner concave surface of an acetabular liner component.

FIG. 17 is a plot 1700 showing an image profile, corresponding to still another particular image pattern, as observed by the camera 920 of FIG. 9A as the camera 920 moves on still another imaging path (e.g., example path 1202) across an inner concave surface (e.g., inner concave surface 1104) of an acetabular liner component (e.g., acetabular liner component 902). The plot 1700 may include a first expressive value 1702, and a second expressive value 1704.

In various embodiments, the first expressive value 1702 represents a saturation value of a unique color patterned on a sub-pixel imaged at a particular location on the inner concave surface. For example, the first expressive value 1702 may represent a saturation value of the color green on the imaged sub-pixel.

Correspondingly, the second expressive value 1604 may represent a saturation value of a another unique color patterned on the sub-pixel imaged at the particular location on the inner concave surface. For example, the second expressive value 1704 may represent a saturation value of the color blue on the imaged sub-pixel. From the information identified via the first expressive value 1702 and the second expressive value 1704, the system may identify the unique position of the femoral head component on the inner concave surface.

Figure 18A:
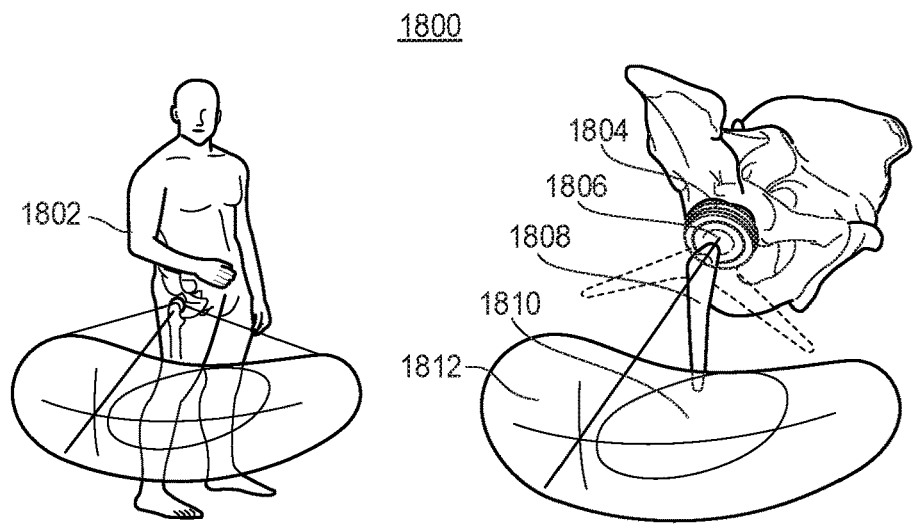
FIGS. 18A, 18B, and 18C depict the range of motion for a hip alignment implant, and zones associated with the risk of dislocation, when the patient is standing, sitting, and transitioning from sitting to standing positions, respectively.
Figure 18B:
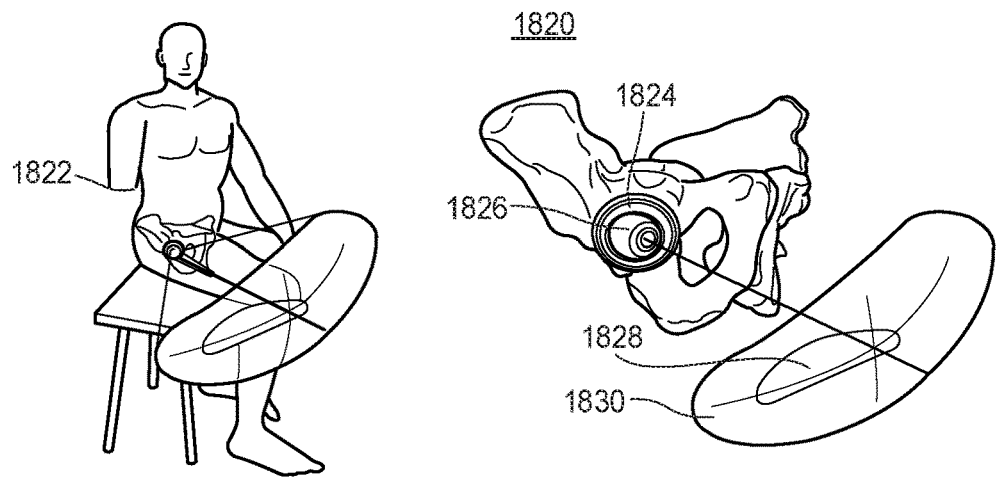
Figure 18C:
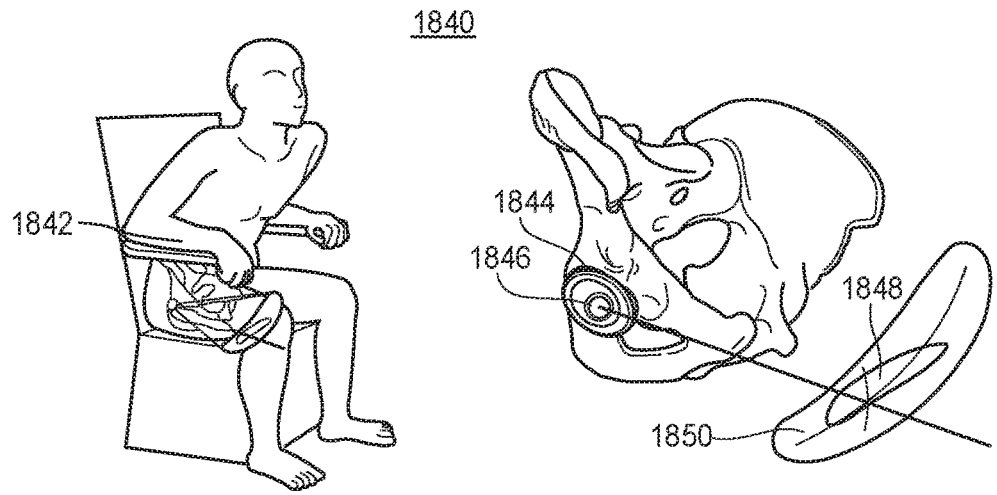

FIGS. 18A, 18B, and 18C depict the range of motion for a hip alignment implant, and zones associated with the risk of dislocation, when the patient is standing 1800, sitting 1820, and transitioning 1840 from sitting to standing positions, respectively. The standing image 1800, as shown in FIG. 18A, depicts a standing patient 1802 who has undergone a hip arthroplasty procedure. As illustrated, the standing patient's 1802 hip includes an acetabular liner component 1804, a femoral head component 1806, and a femoral broach component 1808. Further, the standing image 1800 depicts a patient standing range of motion 1810 and a prosthesis standing range of motion 1812.

The patient standing range of motion 1810 may be defined by the range of motion the patient 1802 is capable of achieving when the implant is in the patient's 1802 hip and the patient 1802 is standing. Generally speaking, and as discussed herein, hip range of motion is limited for numerous reasons, and may be unique to the specific patient in question. Thus, for example, once the hip prosthesis is placed in the patient 1802, the patient's 1802 hip may be taken through a series of movements to, for example, simulate typical movements performed while standing to determine the patient's standing range of motion 1810. The patient standing range of motion 1810 may then be defined by the compilation of points on the inner concave surface identified by the imaging system that did not involve a dislocation event of the femoral head component 1806 from the acetabular liner component 1804.

The prosthesis standing range of motion 1812 may be defined by the range of motion the prosthesis (e.g., the acetabular liner component 1804, femoral head component 1806, and femoral broach component 1808) is capable of achieving when the implant is in the patient's 1802 hip and the patient 1802 is standing. The prosthesis standing range of motion 1812 may be determined prior to insertion of the prosthetic into the patient 1802. For example, the prosthesis may be assembled to mimic the conditions the prosthetic would experience once inserted in the standing patient 1802 and then taken through a series of movements to, for example, simulate typical movements performed while standing by articulating the femoral head component 1806 while attached to the acetabular liner component 1804. The prosthesis standing range of motion 1812 may then be defined by the compilation of points on the inner concave surface identified by the imaging system that did not involve a dislocation event of the femoral head component 1806 from the acetabular liner component 1804.

The sitting image 1820, as shown in FIG. 18B, depicts a sitting patient 1822 who has undergone a hip arthroplasty procedure. As illustrated, the sitting patient's 1822 hip includes an acetabular liner component 1824 and a femoral head component 1826. Further, the sitting image 1820 depicts a patient sitting range of motion 1828 and a prosthesis sitting range of motion 1830.

The patient sitting range of motion 1828 may be defined by the range of motion the patient (e.g., sitting patient 1822) is capable of achieving when the implant is in the patient's 1822 hip and the patient 1822 is sitting. For example, once the hip prosthesis is placed in the patient 1822, the patient's 1822 hip may be taken through a series of movements to, for example, simulate typical movements performed while sitting to determine the patient's sitting range of motion 1828. The patient sitting range of motion 1828 may then be defined by the compilation of points on the inner concave surface identified by the imaging system that did not involve a dislocation event of the femoral head component 1826 from the acetabular liner component 1824.

The prosthesis sitting range of motion 1830 may be defined by the range of motion the prosthesis (e.g., the acetabular liner component 1824 and femoral head component 1826) is capable of achieving when the implant is in the patient's 1822 hip and the patient 1822 is sitting. The prosthesis sitting range of motion 1830 may be determined prior to insertion of the prosthetic into the patient 1822. For example, the prosthesis may be assembled to mimic the conditions the prosthetic would experience once inserted in the sitting patient 1822 and then taken through a series of movements to, for example, simulate typical movements performed while sitting by articulating the femoral head component 1826 while attached to the acetabular liner component 1824. The prosthesis sitting range of motion 1830 may then be defined by the compilation of points on the inner concave surface identified by the imaging system that did not involve a dislocation event of the femoral head component 1826 from the acetabular liner component 1824.

The transition image 1840, as shown in FIG. 18C, depicts a transition patient 1842 who has undergone a hip arthroplasty procedure. As illustrated, the transition patient's 1842 hip includes an acetabular liner component 1844 and a femoral head component 1846. Further, the transition image 1840 depicts a patient transition range of motion 1848 and a prosthesis transition range of motion 1850.

The patient transition range of motion 1848 may be defined by the range of motion the patient (e.g., transition patient 1842) is capable of achieving when the implant is in the patient's 1842 hip and the patient 1842 is transitioning from sitting to standing, or vice versa. For example, once the hip prosthesis is placed in the patient 1842, the patient's 1842 hip may be taken through a series of movements to, for example, simulate typical movements performed while transitioning from sitting to standing (or vice versa) to determine the patient's transition range of motion 1848. The patient transition range of motion 1848 may then be defined by the compilation of points on the inner concave surface identified by the imaging system that did not involve a dislocation event of the femoral head component 1846 from the acetabular liner component 1844.

The prosthesis transition range of motion 1850 may be defined by the range of motion the prosthesis (e.g., the acetabular liner component 1844 and femoral head component 1846) is capable of achieving when the implant is in the patient's 1842 hip and the patient 1842 is transitioning from sitting to standing, or vice versa. The prosthesis transition range of motion 1850 may be determined prior to insertion of the prosthetic into the patient 1842. For example, the prosthesis may be assembled to mimic the conditions the prosthetic would experience once inserted in the transition patient 1842 and then taken through a series of movements to, for example, simulate typical movements performed while transitioning from sitting to standing (or vice versa) by articulating the femoral head component 1846 while attached to the acetabular liner component 1844. The prosthesis transition range of motion 1850 may then be defined by the compilation of points on the inner concave surface identified by the imaging system that did not involve a dislocation event of the femoral head component 1846 from the acetabular liner component 1844.

Determining any and/or all of the ranges of motion discussed herein may take place before, during, or after a hip arthroplasty procedure has been performed. Moreover, various imaging techniques (e.g., EOS imaging) may be used at any and/or all of before, during, or after the hip arthroplasty procedure. The images derived from these techniques may be able to show pelvic tilt as well as normal acetabular and femoral anteversion and abduction in different positions.

Further, to determine any and/or all of the patient ranges of motion, software may simulate the patient's body motion. For example, a patient's height, different measurements from pelvis and femur including acetabular anteversion and abduction, distance between the acetabulum and femur (femoral offset), and femoral anteversion may be input to the simulation software. The simulating software may then move the virtual prosthetic and simulate the contact point between the femoral head component and the acetabular liner component in different tilts. Finally, the software may determine the optimal orientation for the prosthetic based on these simulations.

Figure 19A:
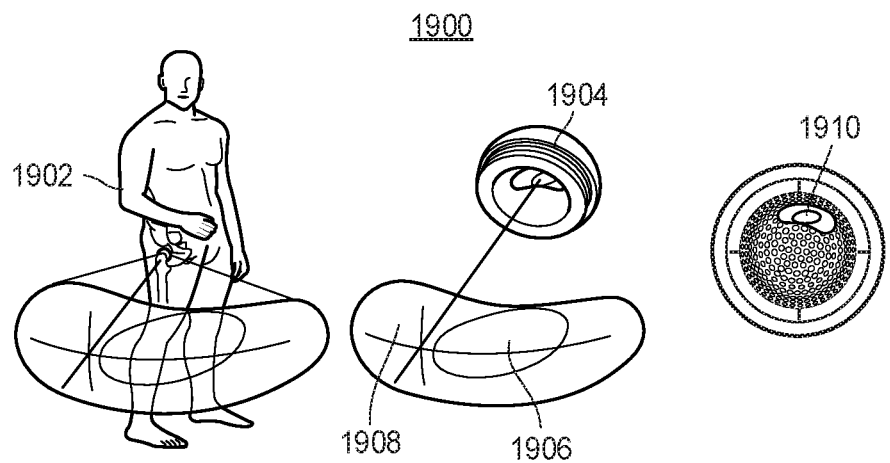
FIGS. 19A, 19B, and 19C show how the zones depicted in FIGS. 18A-18C may map to the concave surface of the acetabular liner.
Figure 19B:
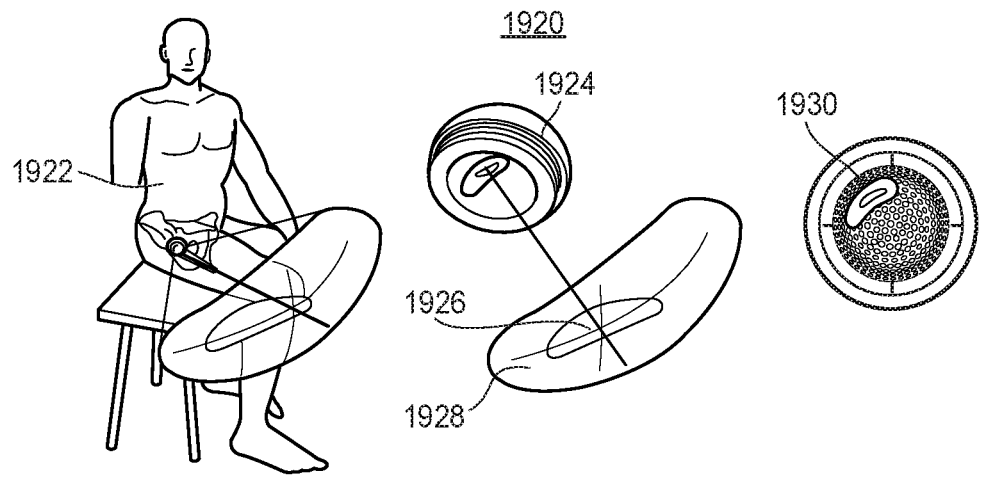
Figure 19C:
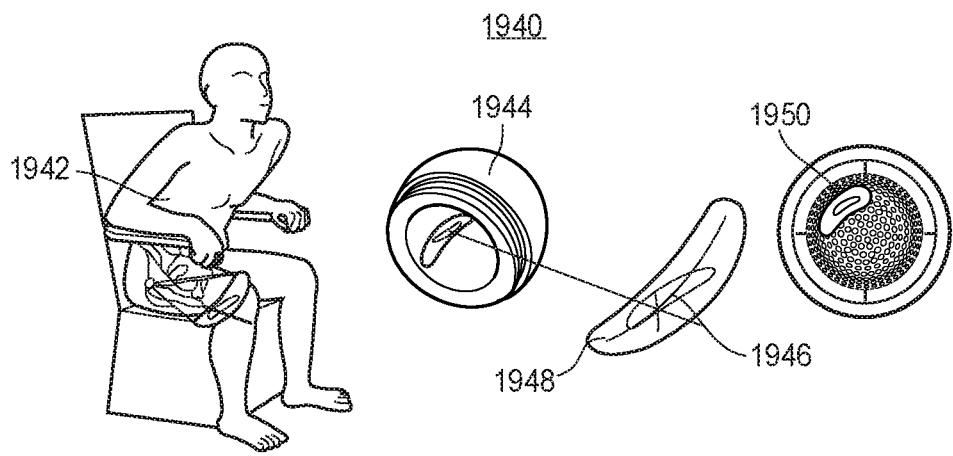

FIGS. 19A, 19B, and 19C show how the zones depicted in FIGS. 18A-18C may map to the concave surface of the acetabular liner. A standing image 1900, as shown in FIG. 19A, depicts a standing patient 1902 who has undergone a hip arthroplasty procedure. As illustrated, the standing patient's 1902 hip includes an acetabular liner component 1904. Further, the standing image 1900 depicts a patient standing range of motion 1906, a prosthesis standing range of motion 1908, and an imposed standing range of motion 1910.

The imposed standing range of motion 1910 may represent the inversion and subsequent imposition of a composition of the patient standing range of motion 1906 and the prosthesis standing range of motion 1908 onto the inner concave surface (e.g., inner concave surface 1104) of the acetabular liner component 1904. For example, as the femoral head component (e.g., femoral head component 914) travels across the surface of the acetabular liner component 1904, the imposed standing range of motion 1910 traced by the femoral head component may be a mirror opposite of the ranges represented by composition of the patient standing range of motion 1906 and the prosthesis standing range of motion 1908.

The sitting image 1920, as shown in FIG. 19B, depicts a sitting patient 1922 who has undergone a hip arthroplasty procedure. As illustrated, the sitting patient's 1922 hip includes an acetabular liner component 1924. Further, the sitting image 1920 depicts a patient sitting range of motion 1926, a prosthesis sitting range of motion 1928, and an imposed sitting range of motion 1930.

The imposed sitting range of motion 1930 may represent the inversion and subsequent imposition of a composition of the patient sitting range of motion 1926 and the prosthesis sitting range of motion 1928 onto the inner concave surface (e.g., inner concave surface 1104) of the acetabular liner component 1924. For example, as the femoral head component (e.g., femoral head component 914) travels across the surface of the acetabular liner component 1924, the imposed sitting range of motion 1930 traced by the femoral head component may be a mirror opposite of the ranges represented by composition of the patient sitting range of motion 1926 and the prosthesis sitting range of motion 1928.

The transition image 1940, as shown in FIG. 19C, depicts a transition patient 1942 who has undergone a hip arthroplasty procedure. As illustrated, the transition patient's 1942 hip includes an acetabular liner component 1894. Further, the transition image 1940 depicts a patient transition range of motion 1946, a prosthesis transition range of motion 1948, and an imposed transition range of motion 1950.

The imposed transition range of motion 1950 may represent the inversion and subsequent imposition of a composition of the patient transition range of motion 1946 and the prosthesis transition range of motion 1948 onto the inner concave surface (e.g., inner concave surface 1104) of the acetabular liner component 1944. For example, as the femoral head component (e.g., femoral head component 914) travels across the surface of the acetabular liner component 1944, the imposed transition range of motion 1950 traced by the femoral head component may be a mirror opposite of the ranges represented by composition of the patient transition range of motion 1946 and the prosthesis transition range of motion 1948.

The ranges of motion identified above in reference to FIGS. 19A-19C may be used to define a safe zone. As further discussed herein, for example, the composition of the imposed ranges of motion (i.e., the imposed standing range of motion 1910, imposed sitting range of motion 1930, and imposed transition range of motion 1950) may be used to identify an overall range of motion corresponding to the femoral head component that will not result in a dislocation, based on the known ranges of both patient and prosthesis range of motion.

Figure 20:
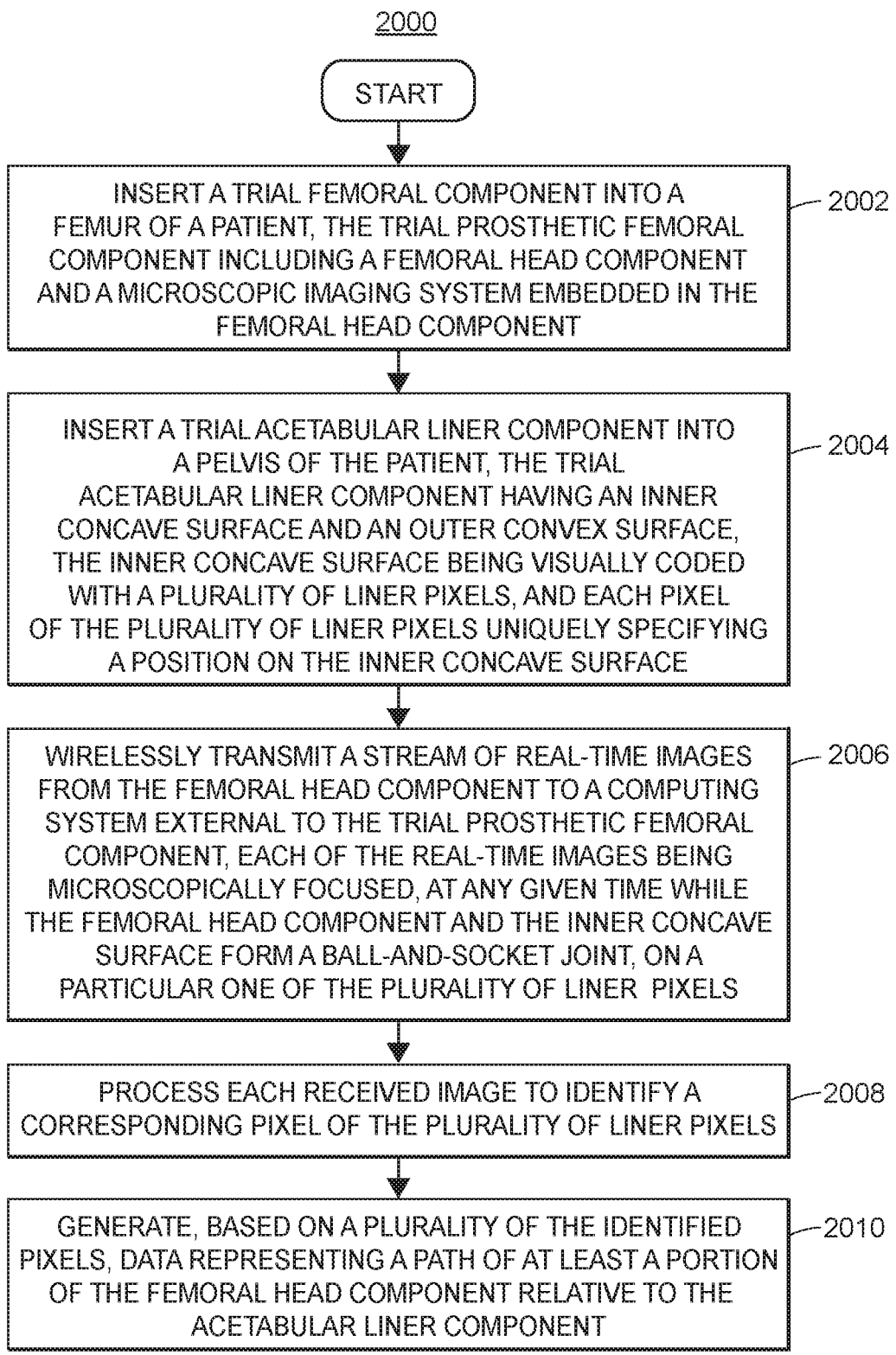
FIG. 20 is a flowchart depicting an example method corresponding to the second aspect of the present disclosure.

FIG. 20 is a flowchart depicting an example method 2000 corresponding to the second aspect of the present disclosure. The method 2000 may be performed in part by a person (e.g., surgeon), and in part by components of a system (e.g., system 900), for example.

The method 2000 begins at block 2002, wherein, for example, a prosthetic femoral component (e.g., prosthetic femoral component 904) may be inserted into a femur of a patient. The prosthetic femoral component may include a femoral head component (e.g., femoral head component 914) and a microscopic imaging system (e.g., camera 920) embedded in the femoral head component. Block 2002 may be performed by a surgeon, for example.

At block 2004, the method 2000 may further include inserting a trial acetabular liner component (e.g., acetabular liner component 902) into a pelvis of the patient. The trial acetabular liner component may have an inner concave surface (e.g., inner concave surface 1104) and an outer convex surface (e.g., outer convex surface), and the inner concave surface may be visually coded with a plurality of liner pixels. Each pixel of the plurality of liner pixels may uniquely specify a position on the inner concave surface. Block 2004 may be performed by a surgeon, for example.

At block 2006, the method 2000 may further include wirelessly transmitting a stream of real-time images from the femoral head component to a computing system (e.g., computer system 906) external to the trial prosthetic femoral component. Each of the real-time images may be microscopically focused, at any given time while the femoral head component and the inner concave surface form a ball-and-socket joint, on a particular one of the plurality of liner pixels. Block 2006 may be performed by the wireless transceiver 924, for example.

At block 2008, the method 2000 may further include processing each received image to identify a corresponding pixel of the plurality of liner pixels. Block 2008 may be performed by the computer system 906 (e.g., processor 926), for example.

At block 2010, the method 2000 may further include generating, based on a plurality of the identified pixels, data representing a path of at least a portion of the femoral head component relative to the acetabular liner component. The data representing a path may be generated, for example, by the computer system. Block 2010 may be performed by the computer system 906 (e.g., processor 926), for example.

In various embodiments, generating the data includes generating data representing a path of a point on an external surface of the femoral head component relative to the acetabular liner component. In these embodiments, the method 2000 includes presenting to a user, on a display (e.g., user interface 930), a visual representation of the path of the point on the external surface of the femoral head component relative to the acetabular liner component. The presentation may take place substantially in real time as the images are captured by the image sensor (e.g., image sensor 921.1). Further in these embodiments, the method 2000 may include generating, by the computer system, a visual representation of a safe zone. The safe zone may indicate a positioning of the point on the external surface of the femoral head component, relative to the acetabular liner component, that is not expected to result in hip dislocation. This safe zone may then be presented on the display in conjunction with the displayed visual representation of the path.

Yet further in these embodiments, the method 2000 includes generating, by the computer system, one or both of (i) an audible alarm, or (ii) a visual alarm. These alarms may be generated, for example, either when the visual representation of the path comes within a threshold distance of a perimeter of the visual representation of the safe zone, or when the visual representation of the path goes outside of the perimeter of the visual representation of the safe zone.

In certain embodiments, the safe zone is specific to a patient for which the hip arthroplasty procedure is being performed. Namely, the safe zone may be specific to at least (i) a height of the patient, and (ii) one or more distances between one or more portions of a pelvis of the patient and one or more portions of a femur of the patient. These measurements may be taken while the patient is in one or more different poses.

Moreover, in some embodiments, processing each received image to identify a corresponding pixel includes detecting a combination and arrangement of colors within the corresponding pixel. As discussed herein, processing each received image to identify a corresponding pixel may further include measuring a blue value and a green value for each of one or more areas within the corresponding pixel.

In these embodiments, the method 2000 includes for at least some of the received images, determining, by the computer system, at least one color calibration factor based on a white area within the corresponding pixel. Processing each received image to identify a corresponding pixel may include applying the determined at least one color calibration factor to one or more colors detected within the corresponding pixel.

Figure 21A:
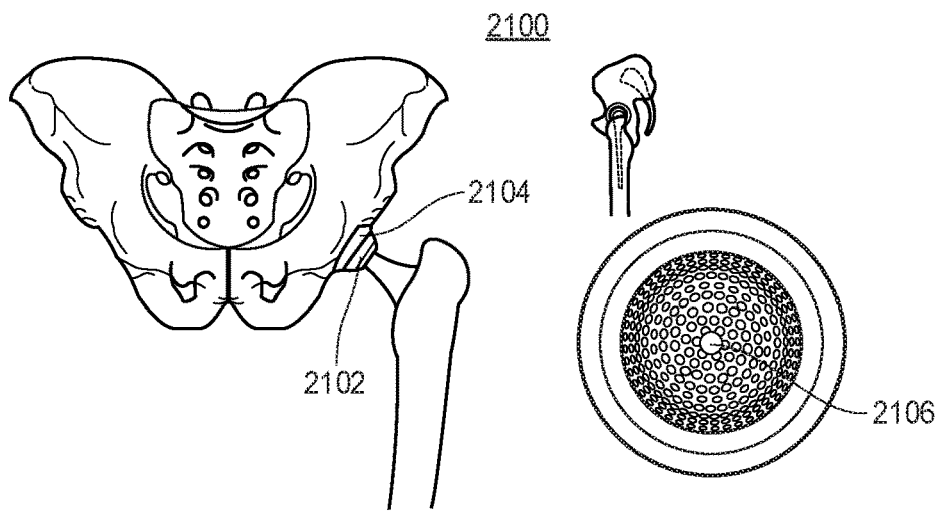
FIGS. 21A, 21B, and 21C depict an example progression of movements that may be used to calibrate the systems corresponding to the first or second aspect of the present disclosure.
Figure 21B:
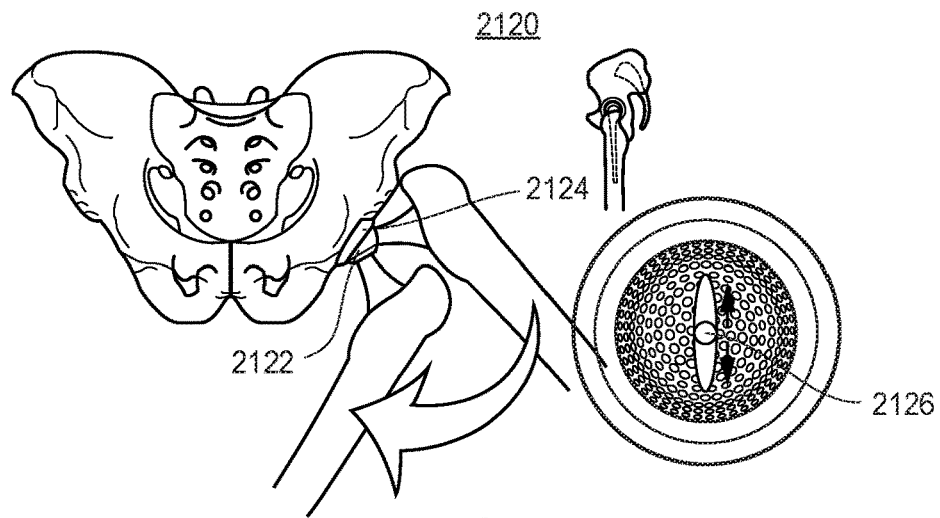
Figure 21C:
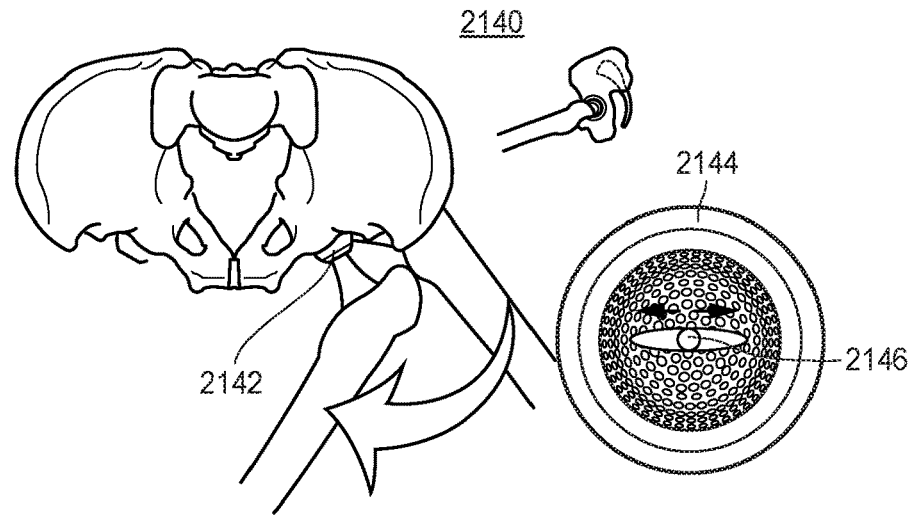

FIGS. 21A, 21B, and 21C depict an example progression of movements that may be used to calibrate the systems corresponding to the first or second aspect of the present disclosure. The first stationary image 2100 depicts a femoral head component 2102, an acetabular liner component 2104, and a central position indicator 2106. As shown in the first stationary image 2100 of FIG. 21A, the femoral head component 2102 is placed in the acetabular liner component 2104 in an approximately centered orientation. The central position indicator 2106 may be used, for example, as a reference point for the subsequent positions, in reference to FIGS. 21B and 21C.

In FIG. 21B, the second stationary image 2120 depicts a femoral head component 2122, an acetabular liner component 2124, and a first extension indicator 2126. The first extension indicator 2126 may represent, for example, the motion of the femoral head component 2122 as the hip is taken into abduction and adduction while in extension. Correspondingly, the computer system (e.g., computer system 906) may recognize the patterning scheme on the acetabular liner component 2124 and track the path taken, for later reference (e.g., to identify a safe zone).

In FIG. 21C, the third stationary image 2140 depicts a femoral head component 2142, an acetabular liner component 2144, and a second extension indicator 2146. The second extension indicator 2146 may represent, for example, the motion of the femoral head component 2142 as the hip is taken into abduction and adduction while in 90 degrees of flexion. Correspondingly, the computer system may recognize the patterning scheme on the acetabular liner component 2144 and track the path taken, for later reference (e.g., to better define the safe zone).

The progression of movements disclosed in FIGS. 21A-21C may be used for a variety of purposes. For example, the progression of movements may be used to optimize the prosthetic range of motion. In other words, the progression of movements may be used to determine the most stable hip in any and/or all functional positions of the patient.

Figure 22A:
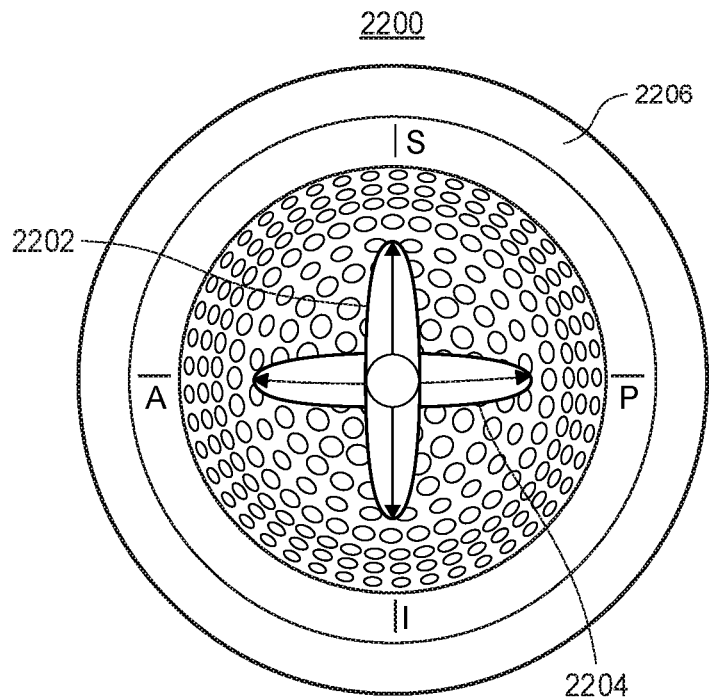
FIGS. 22A and 22B provide top-down views of an inner concave surface of an acetabular liner component with a mapping derived from the progression of movements described in FIGS. 21A-21C, and a determined safe zone with respect to the mapping, respectively.
Figure 22B:
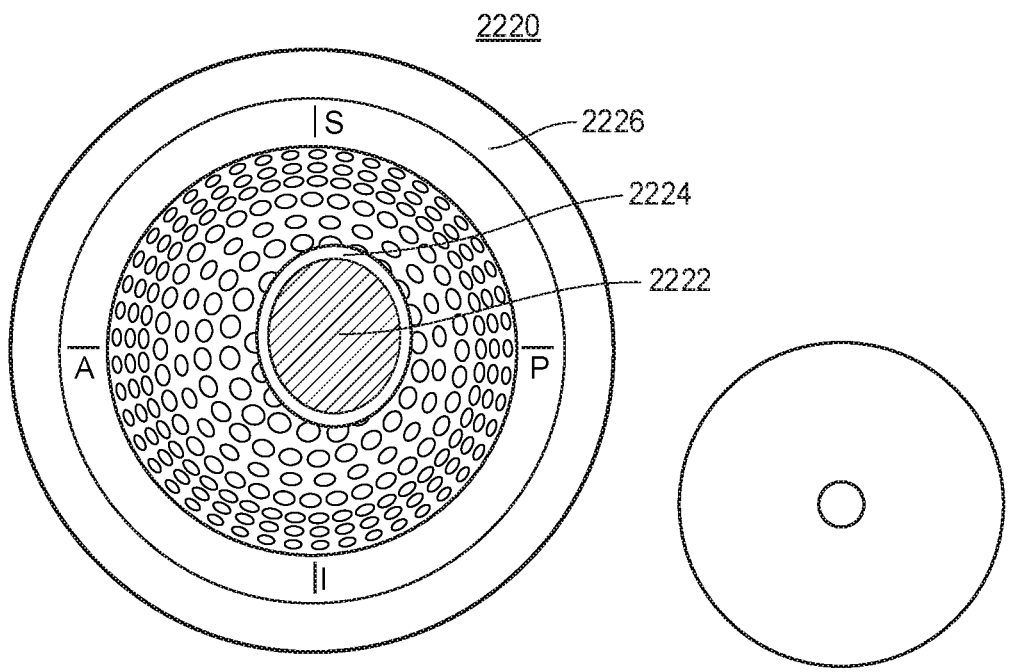

FIGS. 22A and 22B provide top-down views of an inner concave surface of an acetabular liner with a mapping 2200 derived from the progression of movements described in FIGS. 21A-21C, and a determined safe zone 2220 corresponding to the mapping 2200, respectively. The mapping 2200 of FIG. 22A may include a first prosthetic indicator 2202, a second prosthetic indicator 2204, and an acetabular liner component 2206. The first prosthetic indicator 2202 may, for example, correspond to the first extension indicator 2126 of FIG. 21B, and the second prosthetic indicator 2204 may correspond to the second extension indicator 2146 of FIG. 21C.

Using the first prosthetic indicator 2202 and the second prosthetic indicator 2204, the computer system (e.g., computer system 906) may recognize the relative directions (i.e., superior, inferior, anterior, and posterior) on the acetabular liner component 2206. In other words, based on the two indicators (i.e., 2202 and 2204), the computer system may associate certain directions on the acetabular liner component 2206 with a corresponding movement of the patient. To illustrate, if the computer system later identifies a pixel associated with a position indicated within the first prosthetic indicator 2202, the computer system may determine the patient's hip to be in abduction or adduction while in extension. Similarly, if the computer system later identifies a pixel associated with a position indicated within the second prosthetic indicator 2204, the computer system may determine the patient's hip to be in abduction or adduction while in 90 degrees of flexion.

The safe zone view 2220 of FIG. 22B includes a safe zone indicator 2222, a safe zone perimeter 2224, and an acetabular liner component 2226. The safe zone indicator 2222 may include the point of intersection between, for example, the first prosthetic indicator 2202 and the second prosthetic indicator 2204. Moreover, the safe zone indicator 2222 may represent, for example, the area of the inner convex surface of the acetabular liner component 2226 that, if not exited by a contact point of the femoral head component (e.g., femoral head component 914), should not cause hip dislocation to occur. The safe zone perimeter 2224 may indicate, for example, the region of motion of the center of the femoral head component beyond which hip dislocation is possible or likely.

In certain embodiments, the computer system may generate an audible alarm and/or a visual alarm in certain situations. In particular, the alarm(s) may be generated when the visual representation of the path comes within a threshold distance of a perimeter of the visual representation of the safe zone (e.g., safe zone perimeter 2224), and/or when the visual representation of the path goes outside of the perimeter of the visual representation of the safe zone. To illustrate, if the contact point of the femoral head component comes within a threshold distance from the safe zone perimeter 2224 or goes outside the safe zone perimeter 2224, the computer system may generate an alarm in an attempt to avoid hip dislocation.

Once the safe zone indicator 2222 is determined, the stability of the hip may be determined. To make this determination, for example, a surgeon may take the hip through various ranges of motion. Further, the surgeon may be guided in their hip stability determination by, for example, the software implemented on the computer system.

Figure 23A:
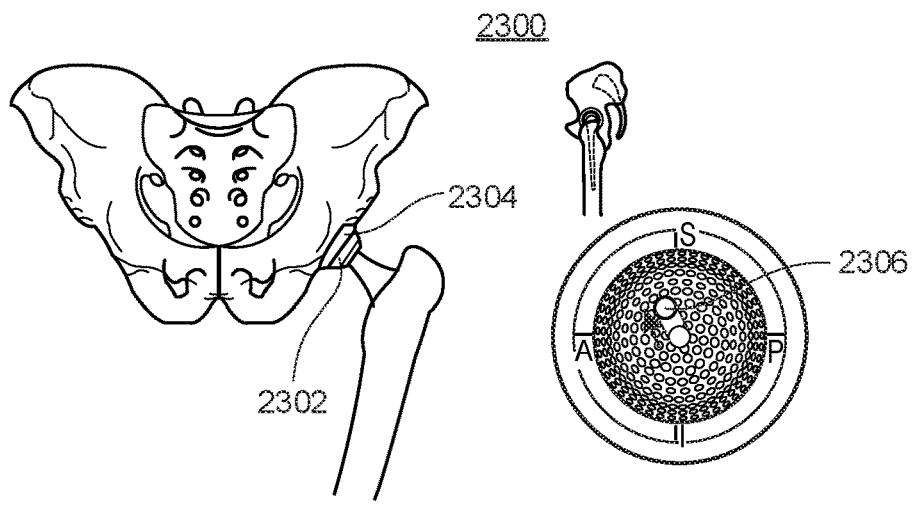
FIGS. 23A, 23B, and 23C are a series of diagrams representing an example progression of movements taking place to simulate a patient walking with the systems described in the first and second aspects of the present disclosure.
Figure 23B:
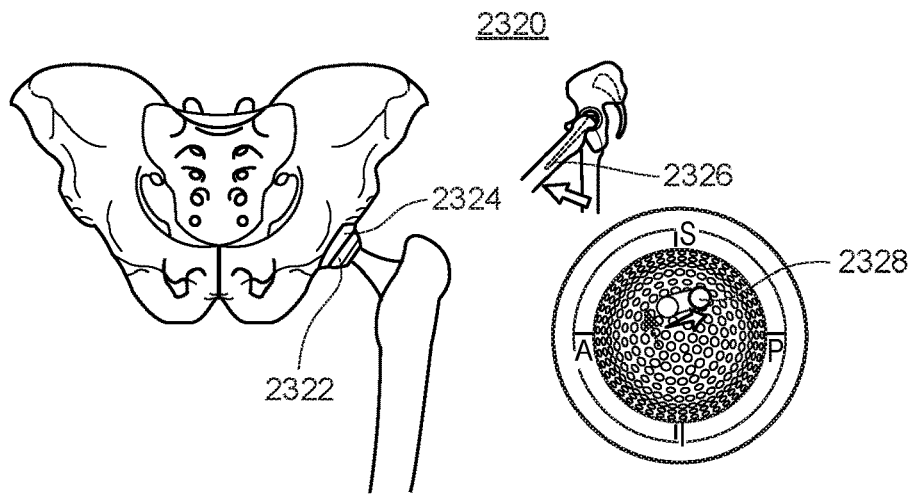
Figure 23C:
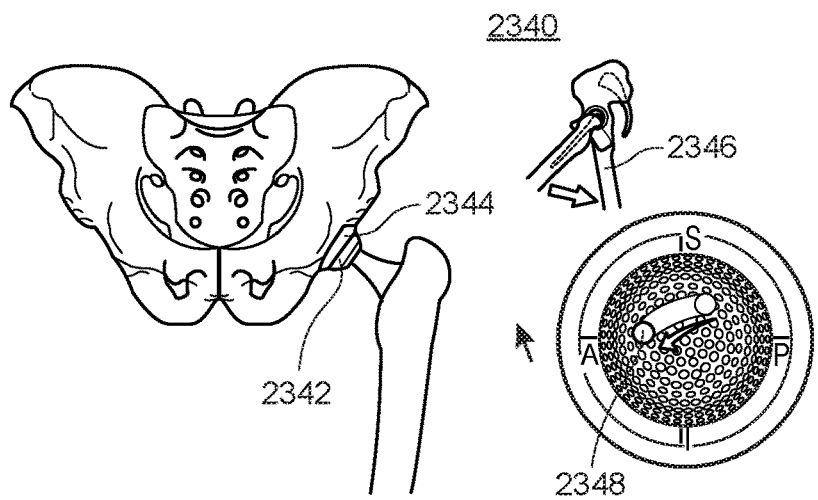

FIGS. 23A, 23B, and 23C are a series of diagrams representing an example progression of movements taking place to simulate a patient walking with the system described in the first or second aspects of the present disclosure. The first walking image 2300 of FIG. 23A depicts a femoral head component 2302, an acetabular liner component 2304, and a first motion indicator 2306. The first motion indicator 2306 may represent, for example, the motion of the femoral head component 2302 across the surface of the acetabular liner component 2304 when a patient shifts weight onto their hips prior to walking.

The second walking image 2320 of FIG. 23B depicts a femoral head component 2322, an acetabular liner component 2324, a second motion illustration 2326, and a second motion indicator 2328. The second motion illustration 2326 may illustrate, for example, a patient moving their hip into flexion while taking a step. The second motion indicator 2328 may represent, for example, the motion of the femoral head component 2322 across the surface of the acetabular liner component 2324 when a patient moves their hip into flexion while taking a step.

The third walking image 2340 of FIG. 23C depicts a femoral head component 2342, an acetabular liner component 2344, a third motion illustration 2346, and a third motion indicator 2348. The third motion illustration 2346 may illustrate, for example, a patient moving their hip into extension while completing a step. The third motion indicator 2348 may represent, for example, the motion of the femoral head component 2342 across the surface of the acetabular liner component 2344 when a patient moves their hip into extension while completing a step.

Figure 24A:
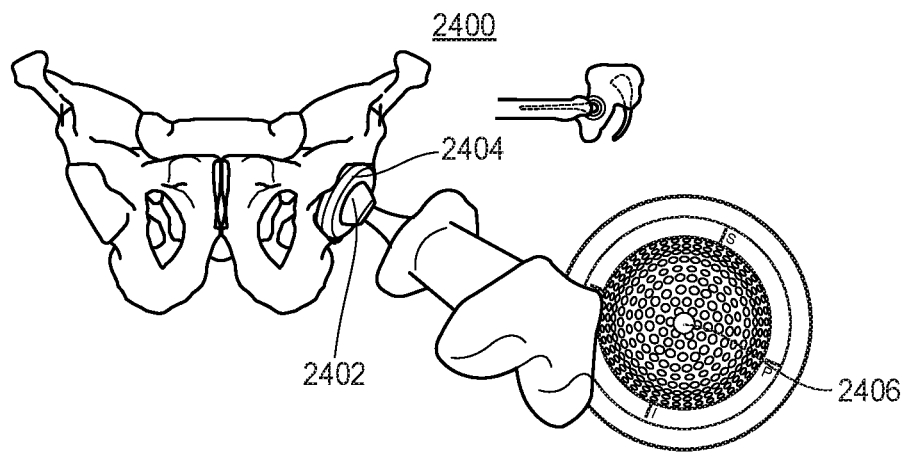
FIGS. 24A, 24B, and 24C are a series of diagrams representing an example progression of movements taking place to simulate a patient sitting with the systems described in the first and second aspects of the present disclosure.
Figure 24B:
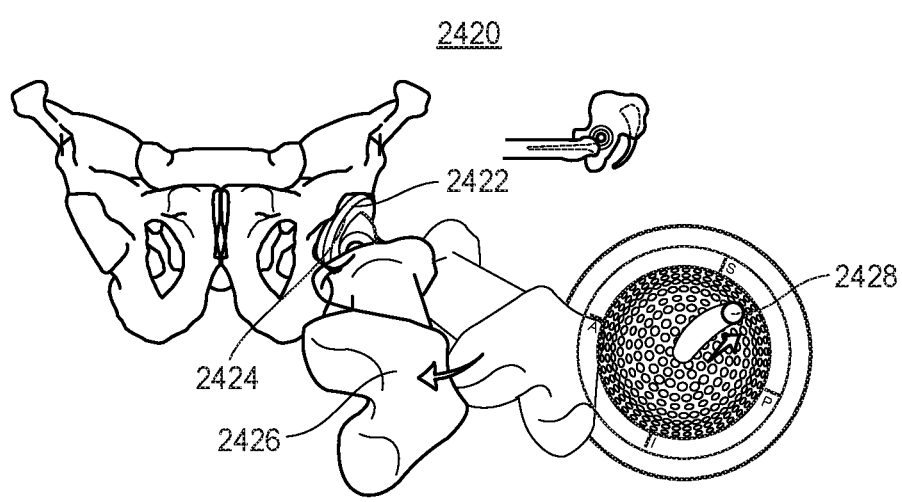
Figure 24C:
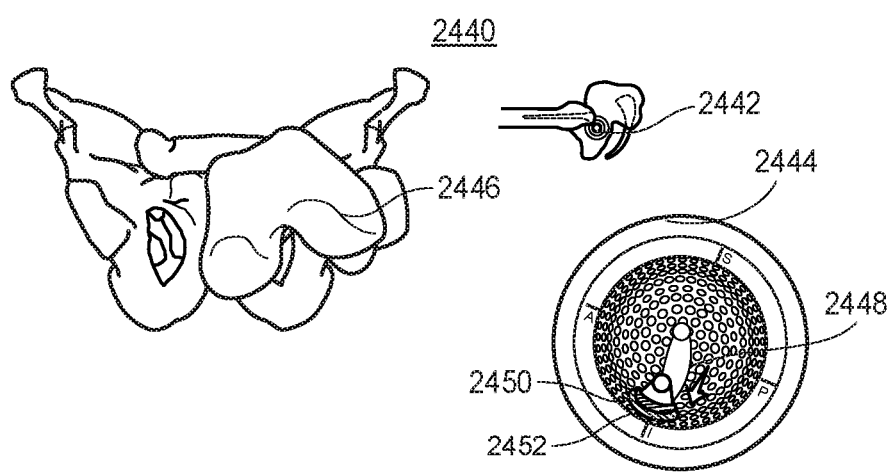

FIGS. 24A, 24B, and 24C are a series of diagrams representing an example progression of movements taking place to simulate a patient sitting with the systems described in the first and second aspects of the present disclosure. The first sitting image 2400 of FIG. 24A includes a femoral head component 2402, an acetabular liner component 2404, and a first motion indicator 2406. The first motion indicator 2406 may represent, for example, the motion of the femoral head component 2402 across the surface of the acetabular liner component 2404 when a patient sits down.

During the sitting process, the pelvis of a patient may, for example, tilt in a posterior direction. As a result, the directions established by the computer system as described herein in reference to FIGS. 21A-21C may shift. For example, the directions associated with the left hip may rotate clockwise, and the directions associated with the right hip may rotate counterclockwise.

The second sitting image 2420 of FIG. 24B depicts a femoral head component 2422, an acetabular liner component 2424, a second motion illustration 2426, and a second motion indicator 2428. The second motion illustration 2426 may illustrate, for example, a patient externally rotating their hip in flexion to create a figure of 4 position while sitting. The second motion indicator 2428 may represent, for example, the motion of the femoral head component 2422 across the surface of the acetabular liner component 2424 when a patient externally rotates their hip in flexion to create a "figure 4" position while sitting.

The third sitting image 2440 of FIG. 24C depicts a femoral head component 2442, an acetabular liner component 2444, a third motion illustration 2446, a third motion indicator 2448, a first dislocation zone 2450, and a second dislocation zone 2452. The third motion illustration 2446 may illustrate, for example, a patient internally rotating their hip in flexion to cross their legs while sitting. The third motion indicator 2448 may represent, for example, the motion of the femoral head component 2442 across the surface of the acetabular liner component 2444 when a patient internally rotates their hip in flexion to cross their legs while sitting.

The first dislocation zone 2450 may represent, for example, a position on the acetabular liner component 2444 at which, if the contact point of the femoral head component 2442 reaches it, the hip may dislocate. Moreover, the second dislocation zone 2452 may represent, for example, a position on the acetabular liner component 2444 at which, if the contact point of the femoral head component 2442 reaches it, the hip will dislocate.

Figure 25A:
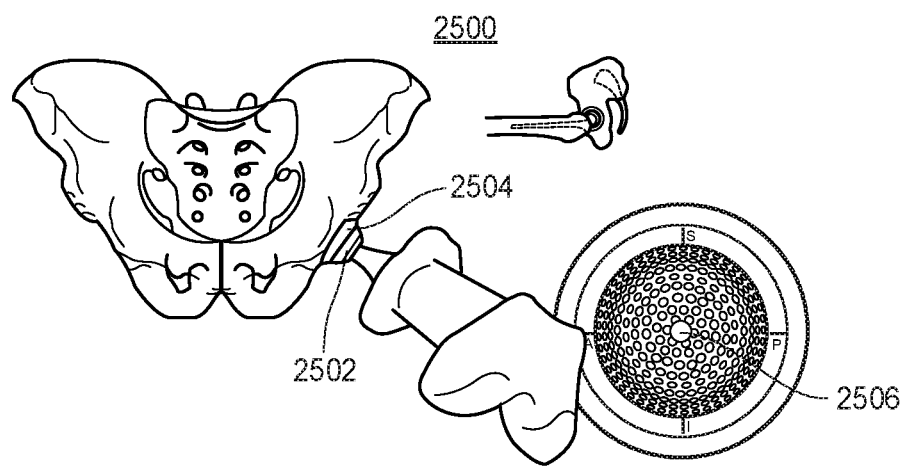
FIGS. 25A, 25B, and 25C are a series of diagrams representing an example progression of movements taking place to simulate a patient transitioning from a sitting position to a standing position with the systems described in the first and second aspects of the present disclosure.
Figure 25B:
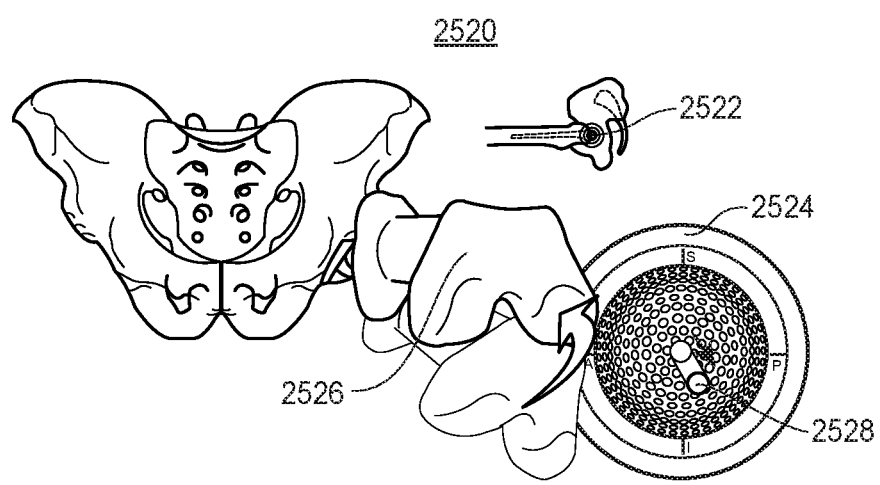
Figure 25C:
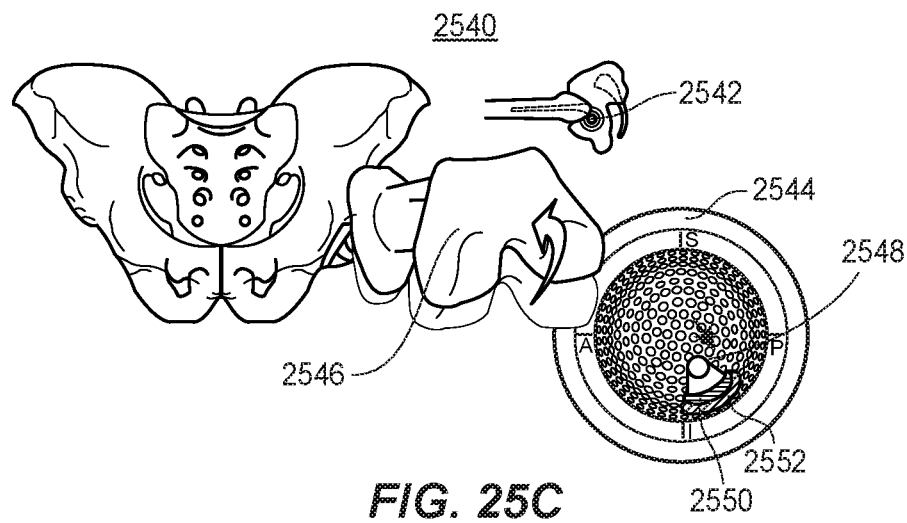

FIGS. 25A, 25B, and 25C are a series of diagrams representing an example progression of movements taking place to simulate a patient transitioning from a sitting position to a standing position with the systems described in the first and second aspects of the present disclosure. The first transition image 2500 of FIG. 25A depicts a femoral head component 2502, an acetabular liner component 2504, and a first motion indicator 2506. The first motion indicator 2506 may represent, for example, the motion of the femoral head component 2502 across the surface of the acetabular liner component 2504 when a patient tilts their pelvis forward prior to transitioning from sitting to standing.

The second transition image 2520 of FIG. 25B depicts a femoral head component 2522, an acetabular liner component 2524, a second motion illustration 2526, and a second motion indicator 2528. The second motion illustration 2526 may illustrate, for example, a patient externally rotating their leg while their pelvis is tilted forward. The second motion indicator 2528 may represent, for example, the motion of the femoral head component 2522 across the surface of the acetabular liner component 2524 when a patient externally rotates their leg while their pelvis is tilted forward.

The third transition image 2540 of FIG. 25C depicts a femoral head component 2542, an acetabular liner component 2544, a third motion illustration 2546, a third motion indicator 2548, a first dislocation zone 2550, and a second dislocation zone 2552. The third motion illustration 2546 may illustrate, for example, a patient internally rotating their leg while their pelvis is tilted forward. The third motion indicator 2548 may represent, for example, the motion of the femoral head component 2542 across the surface of the acetabular liner component 2544 when a patient internally rotates their leg while their pelvis is tilted forward.

The first dislocation zone 2550 may represent, for example, a position on the acetabular liner component 2544 at which, if the contact point of the femoral head component 2542 reaches it, the hip may dislocate. Moreover, the second dislocation zone 2552 may represent, for example, a position on the acetabular liner component 2544 at which, if the contact point of the femoral head component 2542 reaches it, the hip will dislocate.

Figure 26:
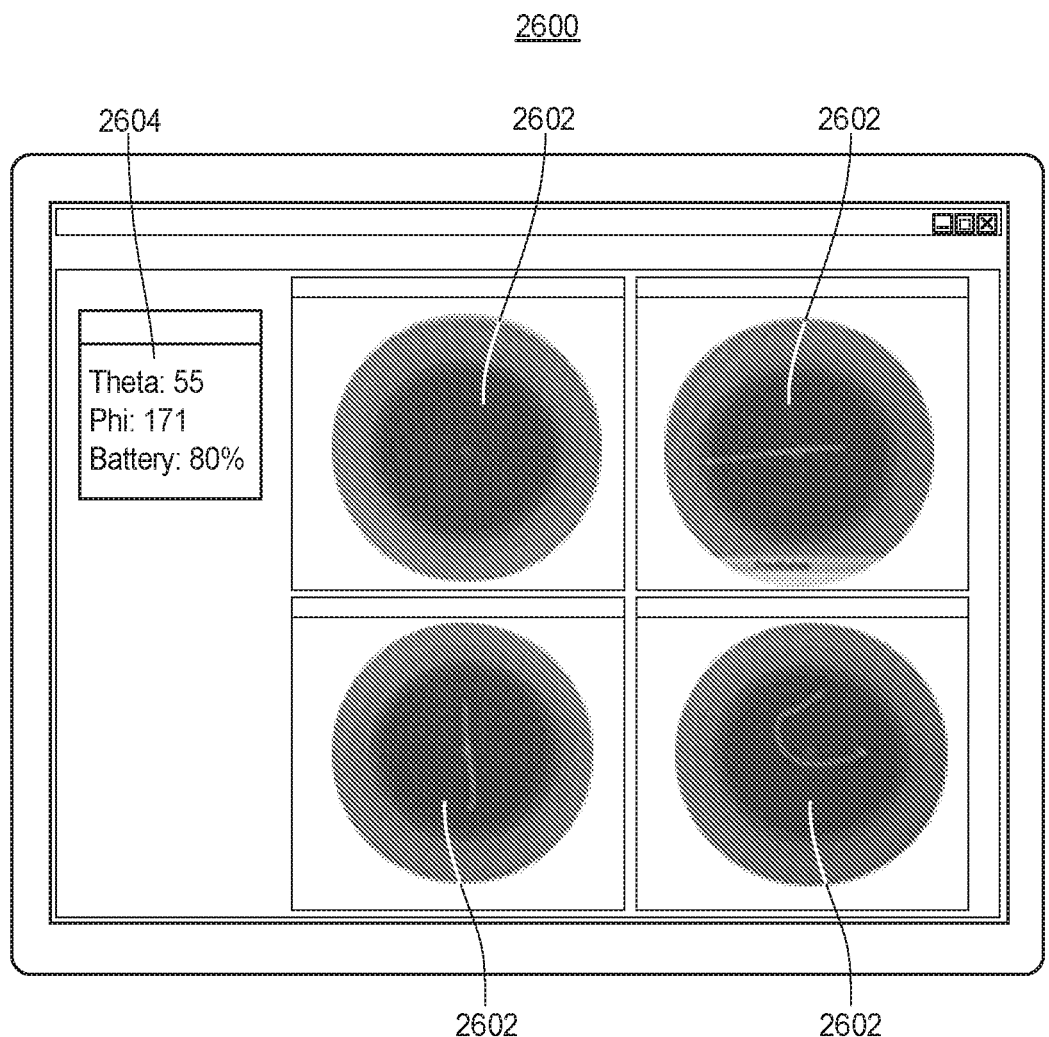
FIG. 26 is an example graphical user interface (GUI) that may be used to track and display the movement of the contact point of a femoral head component across an inner concave surface of an acetabular liner.

FIG. 26 is an example graphical user interface (GUI) 2600 that may be used to track and display the movement of the contact point of a femoral head component across an inner concave surface of an acetabular liner. The example GUI 2600 includes a plurality of position tracking screenshots 2602 and a coordinate tracking screenshot 2604. The plurality of tracked paths 2602 that may, for example, visually represent the path of the contact point of the femoral head component as it traveled across the inner concave surface of the acetabular liner component, with each path corresponding to a time when the surgeon manipulated the patient's leg so as to make a different type of motion. Moreover, the tracked paths 2602 may initially provide this visual representation in real time, or only after a series of movements (such as those discussed in reference to FIGS. 23A-23C) takes place.

The coordinates 2604 may, for example, indicate the geometrical coordinates of the contact point of the femoral head component as it traverses the inner concave surface of the acetabular liner component. This coordinates may be real-time coordinates, or coordinates provided when a user selects a particular point on a path shown in GUI 2600, for example.

Aspects of the Disclosure

1. A position measurement system for use in a hip arthroplasty procedure, the position measurement system comprising: an acetabular liner component having an inner concave surface and an outer convex surface, wherein the acetabular liner component includes at least two magnetic sensors arranged in a spatially distributed manner; and a prosthetic femoral component comprising a femoral head component, wherein the femoral head component and the acetabular liner component are shaped such that a ball-and-socket joint is formed when the femoral head component comes into contact with the inner concave surface of the acetabular liner component, while the ball-and-socket joint is formed, and in at least some orientations of the femoral head component relative to the acetabular liner component, a contact point on an external surface of the femoral head component contacts the inner concave surface, and the femoral head component includes at least one permanent magnet.

2. The position measurement system of aspect 1, wherein the acetabular liner component and the prosthetic femoral component are trial components to be removed prior to completion of the hip arthroplasty procedure.

3. The position measurement system of aspect 1 or 2, wherein the at least one permanent magnet is entirely embedded in the femoral head component.

4. The position measurement system of any one of aspects 1 through 3, wherein the at least one permanent magnet includes a cylindrical magnet.

5. The position measurement system of aspect 4, wherein a center axis of the cylindrical magnet passes through the contact point, and wherein the cylindrical magnet is positioned between ⅛ inch and ½ inch away from the contact point.

6. The position measurement system of aspect 4 or 5, wherein one or both of (i) the cylindrical magnet has a radius between ⅟₃₂ inch and ⅛ inch, and (ii) the cylindrical magnet has a length between ⅟₃₂ inch and ⅛ inch.

7. The position measurement system of any one of aspects 1 through 6, wherein the at least one permanent magnet includes a neodymium magnet with a grade between N45 and N50.

8. The position measurement system of any one of aspects 1 through 7, wherein each of the at least two magnetic sensors is a multi-axis sensor capable of detecting magnetic field intensity and direction in three dimensions.

9. The position measurement system of any one of aspects 1 through 8, wherein the acetabular liner component includes exactly three magnetic sensors.

10. The position measurement system of aspect 9, wherein each of the three magnetic sensors is evenly spaced between the other two magnetic sensors.

11. The position measurement system of aspect 10, wherein the three magnetic sensors are evenly distributed about a center axis of the acetabular liner component.

12. The position measurement system of any one of aspects 1 through 11, wherein each of the at least two magnetic sensors is on or immediately adjacent to the inner concave surface.

13. The position measurement system of any one of aspects 1 through 12, wherein the prosthetic femoral component further comprises a femoral neck component; and the femoral head component is configured to physically couple to the femoral neck component in a removable manner.

14. The position measurement system of aspect 13, wherein: the prosthetic femoral component further comprises a broach component; and the femoral neck component is configured to physically couple to the broach component in a removable manner.

15. The position measurement system of any one of aspects 1 through 14, wherein the acetabular liner component includes a plurality of pressure sensors arranged along an outer perimeter of the inner concave surface.

16. The position measurement system of any one of aspects 1 through 15, wherein: the acetabular liner component further comprises a wireless transceiver; the wireless transceiver includes one or more antennas and a radio frequency (RF) module; the wireless transceiver is configured to transmit measured magnetic field data to a destination external to the acetabular liner component; and the measured magnetic field data is indicative of sensor readings captured by the at least two magnetic sensors.

17. The position measurement system of aspect 16, wherein the wireless transceiver is configured to transmit the measured magnetic field data to the destination external to the acetabular liner component using a Bluetooth communication protocol.

18. The position measurement system of aspect 16 or 17, wherein the acetabular liner component comprises a microcontroller configured to receive the sensor readings from the at least two magnetic sensors.

19. The position measurement system of aspect 18, wherein the microcontroller includes at least a portion of the wireless transceiver.

20. The position measurement system of aspect 18 or 19, wherein the acetabular liner component further comprises a battery electrically coupled to the microcontroller.

21. The position measurement system of aspect 20, wherein the at least two magnetic sensors, the microcontroller, the wireless transceiver, and the battery are entirely embedded in a body of the acetabular liner component.

22. The position measurement system of aspect 21, wherein the body of the acetabular liner component is hermetically sealed.

23. The position measurement system of aspect 21 or 22, wherein the body of the acetabular liner component comprises a polyurethane material.

24. The position measurement system of aspect 23, wherein the body of the acetabular liner component consists of a unitary piece of the polyurethane material.

25. The position measurement system of any one of aspects 16 through 24, wherein the wireless transceiver is configured to transmit the measured magnetic field data to the destination external to the acetabular liner component at a rate of at least 8 frames per second, substantially in real time as the sensor readings are captured by the at least two magnetic sensors.

26. The position measurement system of any one of aspects 16 through 25, further comprising: a computer system comprising one or more processors and a memory, wherein the memory stores instructions that, when executed by the one or more processors, cause the computer system to: receive the measured magnetic field data transmitted by the wireless transceiver, and process the received measured magnetic field data to determine orientations of the femoral head component relative to the acetabular liner component, substantially in real time as the at least two magnetic sensors capture the sensor readings.

27. The position measurement system of aspect 26, wherein the instructions, when executed by the one or more processors, further cause the computer system to: detect a dislocation of the femoral head component from the acetabular liner component based on the received measured magnetic field data; and output data indicative of whether the dislocation is due to implant impingement or bony impingement.

28. The position measurement system of aspect 26, wherein the instructions cause the computer system to generate, based on the determined orientations, data representing a path of the contact point relative to the acetabular liner component.

29. The position measurement system of aspect 28, wherein the computer system further comprises a display, and wherein the instructions further cause the computer system to present to a user, on the display, a visual representation of the path of the contact point relative to the acetabular liner component, substantially in real time as the at least two magnetic sensors capture the sensor readings.

30. The position measurement system of aspect 29, wherein the instructions further cause the computer system to: generate a visual representation of a safe zone, the safe zone indicating a positioning of the contact point, relative to the acetabular liner component, that is not expected to result in hip dislocation; and present the safe zone on the display in conjunction with the displayed visual representation of the path.

31. The position measurement system of aspect 30, wherein the instructions further cause the computer system to: generate one or both of (i) an audible alarm, or (ii) a visual alarm, either when the visual representation of the path comes within a threshold distance of a perimeter of the visual representation of the safe zone, or when the visual representation of the path goes outside of the perimeter of the visual representation of the safe zone.

32. The position measurement system of aspect 30 or 31, wherein the safe zone is specific to a patient for which the hip arthroplasty procedure is being performed.

33. The position measurement system of aspect 32, wherein the safe zone is specific to at least (i) a height of the patient, and (ii) one or more distances between one or more portions of a pelvis of the patient and one or more portions of a femur of the patient, as measured while the patient is in one or more different poses.

34. The position measurement system of any one of aspects 26 through 33, wherein the instructions cause the computer system to determine the orientations of the femoral head component relative to the acetabular liner component at least by using the measured magnetic field data to determine projections of the contact point onto the inner concave surface.

35. The position measurement system of any one of aspects 26 through 34, wherein: the instructions cause the computer system to determine the orientations of the femoral head component relative to the acetabular liner component at least by inputting the measured magnetic field data, or data derived from the measured magnetic field data, to a trained neural network; and the trained neural network outputs data indicative of the orientations of the femoral head component relative to the acetabular liner component.

36. The position measurement system of aspect 35, wherein the acetabular liner component includes exactly three multi-axis magnetic sensors each having an accuracy of at least 10 micro-Tesla, and the orientations of the femoral head component relative to the acetabular liner component are accurate to within 0.2 degrees in any direction along the inner concave surface.

37. The position measurement system of any one of aspects 26 through 36, wherein the instructions cause the computer system to determine the orientations of the femoral head component relative to the acetabular liner component at least by: determining one or more ambient magnetic fields that are measured by the at least two magnetic sensors while the ball-and-socket joint is not formed; determining at least one magnetic field calibration factor based on the one or more ambient magnetic fields; and determining the orientations of the femoral head component relative to the acetabular liner component based on the measured magnetic field data and the at least one magnetic field calibration factor.

38. The position measurement system of any one of aspects 26 through 37, wherein the acetabular liner component includes a plurality of pressure sensors arranged along an outer perimeter of the inner concave surface, and wherein the instructions further cause the computer system to: monitor pressure measurements of the one or more pressure sensors; and generate, based on the monitored pressure measurements, an audio or visual indication of when a surface is impinging upon the acetabular liner component.

39. A method for improving hip stability outcomes for hip arthroplasty procedures, the method comprising: inserting a trial acetabular liner component into a pelvis of a patient, wherein the trial acetabular liner component has an inner concave surface and an outer convex surface, and includes at least two magnetic sensors arranged in a spatially distributed manner; inserting a trial prosthetic femoral component into a femur of the patient, wherein (i) the trial prosthetic femoral component includes a femoral head component, (ii) the femoral head component and the acetabular liner component are shaped such that a ball-and-socket joint is formed when the femoral head component comes into contact with the inner concave surface of the acetabular liner component, (iii) while the ball-and-socket joint is formed, and in at least some orientations of the femoral head component relative to the acetabular liner component, a contact point on an external surface of the femoral head component contacts the inner concave surface, and (iv) the femoral head component includes at least one permanent magnet; wirelessly transmitting measured magnetic field data, indicative of sensor readings captured by the at least two magnetic sensors, from the femoral head component to a computing system external to the trial prosthetic femoral component; processing, by the computing system, the measured magnetic field data to determine orientations of the femoral head component relative to the acetabular liner component, substantially in real time as the at least two magnetic sensors capture the sensor readings; and presenting, by the computing system and on a display, information indicative of the determined orientations.

40. The method of aspect 39, wherein presenting information indicative of the determined orientations includes: generating, based on the determined orientations, data representing a path of the contact point relative to the acetabular liner component; and presenting on the display a visual representation of the path of the contact point, substantially in real time as the at least two magnetic sensors capture the sensor readings.

41. The method of aspect 40, further comprising: generating, by the computer system, a visual representation of a safe zone, the safe zone indicating a positioning of the point on the external surface of the femoral head component, relative to the acetabular liner component, that is not expected to result in hip dislocation; and presenting the safe zone on the display in conjunction with the displayed visual representation of the path.

42. The method of aspect 41, further comprising: generating, by the computer system, one or both of (i) an audible alarm, or (ii) a visual alarm, either when the visual representation of the path comes within a threshold distance of a perimeter of the visual representation of the safe zone, or when the visual representation of the path goes outside of the perimeter of the visual representation of the safe zone.

43. The method of aspect 41 or 42, wherein the safe zone is specific to a patient for which the hip arthroplasty procedure is being performed.

44. The method of aspect 43, wherein the safe zone is specific to at least (i) a height of the patient, and (ii) one or more distances between one or more portions of a pelvis of the patient and one or more portions of a femur of the patient, as measured while the patient is in one or more different poses.

45. The method of any one of aspects 39 through 44, wherein determining the orientations of the femoral head component relative to the acetabular liner component includes using the measured magnetic field data to determine projections of the contact point onto the inner concave surface.

46. The method of any one of aspects 39 through 45, wherein determining the orientations of the femoral head component relative to the acetabular liner component includes inputting the measured magnetic field data, or data derived from the measured magnetic field data, to a trained neural network, and wherein the trained neural network outputs data indicative of the orientations of the femoral head component relative to the acetabular liner component.

47. The method of any one of aspects 39 through 46, further comprising: determining one or more ambient magnetic fields that are measured by the at least two magnetic sensors while the ball-and-socket joint is not formed; determining at least one magnetic field calibration factor based on the one or more ambient magnetic fields; and determining the orientations of the femoral head component relative to the acetabular liner component based on the measured magnetic field data and the at least one magnetic field calibration factor.

48. The method of any one of aspects 39 through 47, further comprising: detecting, by the computer system, a dislocation of the femoral head component from the acetabular liner component based on the measured magnetic field data; and outputting data indicative of whether the dislocation is due to implant impingement or bony impingement.

49. A position measurement system for use in a hip arthroplasty procedure, the position measurement system comprising: an acetabular liner component having an inner concave surface and an outer convex surface, wherein the inner concave surface is visually coded with a plurality of liner pixels, and wherein each pixel of the plurality of liner pixels uniquely specifies a position on the inner concave surface by way of including either (i) a different color, or (ii) a different combination and/or arrangement of two or more colors; and a prosthetic femoral component comprising a femoral head component, wherein the femoral head component and the acetabular liner component are shaped such that a ball-and-socket joint is formed when the femoral head component comes into contact with the inner concave surface of the acetabular liner component, and wherein the femoral head component comprises a microscopic imaging system that is embedded in the femoral head component and is configured to capture images that, while the ball-and-socket joint is formed, are sized so as to each contain at least one pixel of the plurality of liner pixels.

50. The position measurement system of aspect 49, wherein the acetabular liner component and the prosthetic femoral component are trial components to be removed prior to completion of the hip arthroplasty procedure.

51. The position measurement system of aspect 49 or 50, wherein each pixel of the plurality of liner pixels uniquely specifies a position on the inner concave surface by way of including either (i) a different color that does not contain any element of red in a red-green-blue (RGB) color model, or (ii) a different combination and/or arrangement of two or more colors that each do not contain any element of red in the RGB color model.

52. The position measurement system of any one of aspects 49 through 51, wherein each pixel of the plurality of liner pixels is immediately adjacent to at least one other pixel of the plurality of liner pixels.

53. The position measurement system of any one of aspects 49 through 52, wherein the plurality of liner pixels cover at least 80% of the inner concave surface.

54. The position measurement system of aspect 53, wherein the plurality of liner pixels cover substantially an entirety of the inner concave surface.

55. The position measurement system of any one of aspects 49 through 54, wherein: the plurality of liner pixels includes at least 1,000 pixels; and each pixel of the plurality of liner pixels has a longest dimension, along the inner concave surface, of less than 500 micrometers.

56. The position measurement system of aspect 55, wherein the longest dimension is between 150 and 250 micrometers.

57. The position measurement system of any one of aspects 49 through 55, wherein the acetabular liner component includes a plurality of pressure sensors arranged along an outer perimeter of the inner concave surface.

58. The position measurement system of any one of aspects 49 through 57, wherein: each pixel of the plurality of liner pixels uniquely specifies a position on the inner concave surface by way of including a different color; and the inner concave surface is further visually coded with a plurality of white pixels, the plurality of white pixels being interspersed among the plurality of liner pixels.

59. The position measurement system of any one of aspects 49 through 57, wherein each pixel of the plurality of liner pixels: uniquely specifies a position on the inner concave surface by way of including a different combination and/or arrangement of two or more colors; and includes a respective plurality of sub-pixels, with at least one of the respective plurality of sub-pixels being white.

60. The position measurement system of aspect 59, wherein each respective plurality of sub-pixels includes at least two geometric shapes, with at least one of the geometric shapes being colored and at least one of the geometric shapes being white.

61. The position measurement system of aspect 60, wherein the geometric shapes are sub-pixels.

62. The position measurement system of aspect 61, wherein each respective plurality of sub-pixels includes four sub-pixels, with three sub-pixels being colored and one sub-pixel being white.

63. The position measurement system of aspect 61 or 62, wherein each sub-pixel of each sub-pixel is between 50 and 150 micrometers in width.

64. The position measurement system of any one of aspects 59 through 63, wherein each pixel of the plurality of liner pixels uniquely specifies a position on the inner concave surface by way of including a different combination and arrangement of two or more colors.

65. The position measurement system of aspect 64, wherein the combination and arrangement of two or more colors in the plurality of liner pixels is arranged according to a reflected binary code (RBC) representation.

66. The position measurement system of any one of aspects 59 through 65, wherein the combination and arrangement of two or more colors in each pixel of the plurality of liner pixels is unique from the combination and arrangement of two or more colors in every other pixel of the plurality of liner pixels, irrespective of whether any of the plurality of liner pixels is rotated about its center point.

67. The position measurement system of any one of aspects 59 through 66, wherein the plurality of liner pixels includes less than 300 different colors.

68. The position measurement system of aspect 67, wherein the plurality of liner pixels includes less than 70 different colors.

69. The position measurement system of any one of aspects 49 through 68, wherein one or both of (i) the acetabular liner component, and (ii) the femoral head component, comprises a lighting system that is configured to illuminate at least a portion of the inner concave surface while the ball-and-socket joint is formed.

70. The position measurement system of aspect 69, wherein the lighting system includes a light-emitting diode (LED) array embedded in the acetabular liner component and/or the femoral head component.

71. The position measurement system of any one of aspects 49 through 70, wherein the acetabular liner component comprises a polyurethane cup.

72. The position measurement system of any one of aspects 49 through 71, wherein: the prosthetic femoral component further comprises a femoral neck component; and the femoral head component is configured to physically couple to the femoral neck component in a removable manner.

73. The position measurement system of aspect 72, wherein: the prosthetic femoral component further comprises a broach component; and the femoral neck component is configured to physically couple to the broach component in a removable manner.

74. The position measurement system of any one of aspects 49 through 73, wherein the microscopic imaging system comprises an image sensor and a lens system.

75. The position measurement system of aspect 74, wherein the lens system includes (i) an objective lens, and (ii) a camera lens situated between the image sensor and the objective lens.

76. The position measurement system of aspect 75, wherein the camera lens has a focal length between 1.8 and 7.2 millimeters, and the objective lens has a focal length between 0.6 and 2.4 millimeters.

77. The position measurement system of any one of aspects 74 through 76, wherein the image sensor includes a plurality of image sensor pixels arranged in a two-dimensional array.

78. The position measurement system of aspect 77, wherein the image sensor includes fewer than 300,000 image sensor pixels.

79. The position measurement system of aspect 77 or 78, wherein sizes of each of the plurality of image sensor pixels, sizes of each of the plurality of liner pixels, and a magnification ratio of the lens system are collectively configured to provide a resolution of 3 degrees or finer in positioning of the femoral head component relative to the acetabular liner component.

80. The position measurement system of aspect 79, wherein the sizes of each of the plurality of image sensor pixels, the sizes of each of the plurality of liner pixels, and the magnification ratio of the lens system are collectively configured to provide a resolution of 1 degree or finer in positioning of the femoral head component relative to the acetabular liner component.

81. The position measurement system of any one of aspects 77 through 80, wherein each image sensor pixel has a largest dimension of less than 5 micrometers.

82. The position measurement system of any one of aspects 77 through 81, wherein the lens system provides a magnification ratio between 2:1 and 5:1.

83. The position measurement system of any one of aspects 74 through 82, wherein the lens system is configured to focus, while the ball-and-socket joint is formed, on a single pixel of the plurality of liner pixels at any given time.

84. The position measurement system of any one of aspects 49 through 83, wherein: the prosthetic femoral component further comprises a wireless transceiver embedded within the femoral head component; the wireless transceiver includes one or more antennas and a radio frequency (RF) module; and the wireless transceiver is configured to transmit images captured by the image sensor to a destination external to the prosthetic femoral component.

85. The position measurement system of aspect 84, wherein the wireless transceiver is configured to transmit images captured by the image sensor to the destination external to the prosthetic femoral component using a Bluetooth communication protocol.

86. The position measurement system of aspect 84 or 85, wherein the prosthetic femoral component further comprises a battery that is entirely embedded within the femoral head component and electrically coupled to the wireless transceiver.

87. The position measurement system of any one of aspects 84 through 86, wherein the wireless transceiver is configured to transmit the images captured by the image sensor to the destination external to the prosthetic femoral component at a rate of at least 30 frames per second, substantially in real time as the images are captured by the image sensor.

88. The position measurement system of any one of aspects 84 through 87, further comprising: a computer system comprising one or more processors and a memory, wherein the memory stores instructions that, when executed by the one or more processors, cause the computer system to receive the images transmitted by the wireless transceiver, for each received image, process the received image to identify a corresponding pixel of the plurality of liner pixels, and based on a plurality of the identified pixels, generate data representing a path of at least a portion of the femoral head component relative to the acetabular liner component.

89. The position measurement system of aspect 88, wherein the instructions cause the computer system to generate data representing a path of a point on an external surface of the femoral head component relative to the acetabular liner component.

90. The position measurement system of aspect 89, wherein the computer system further comprises a display, and wherein the instructions further cause the computer system to present to a user, on the display, a visual representation of the path of the point on the external surface of the femoral head component relative to the acetabular liner component, substantially in real time as the images are captured by the image sensor.

91. The position measurement system of aspect 90, wherein the instructions further cause the computer system to: generate a visual representation of a safe zone, the safe zone indicating a positioning of the point on the external surface of the femoral head component, relative to the acetabular liner component, that is not expected to result in hip dislocation; and present the safe zone on the display in conjunction with the displayed visual representation of the path.

92. The position measurement system of aspect 91, wherein the instructions further cause the computer system to: generate one or both of (i) an audible alarm, or (ii) a visual alarm, either when the visual representation of the path comes within a threshold distance of a perimeter of the visual representation of the safe zone, or when the visual representation of the path goes outside of the perimeter of the visual representation of the safe zone.

93. The position measurement system of aspect 91 or 92, wherein the safe zone is specific to a patient for which the hip arthroplasty procedure is being performed.

94. The position measurement system of aspect 93, wherein the safe zone is specific to at least (i) a height of the patient, and (ii) one or more distances between one or more portions of a pelvis of the patient and one or more portions of a femur of the patient, as measured while the patient is in one or more different poses.

95. The position measurement system of any one of aspects 88 through 94, wherein the acetabular liner component includes a plurality of pressure sensors arranged along an outer perimeter of the inner concave surface, and wherein the instructions further cause the computer system to: monitor pressure measurements of the one or more pressure sensors; and generate, based on the monitored pressure measurements, an audio or visual indication of when a surface is impinging upon the acetabular liner component.

96. The position measurement system of any one of aspects 88 through 95, wherein the instructions cause the computer system to identify the corresponding pixel of the plurality of liner pixels at least by detecting a combination and arrangement of colors within the corresponding pixel.

97. The position measurement system of any one of aspects 88 through 96, wherein the instructions cause the computer system to identify the corresponding pixel of the plurality of liner pixels at least by measuring a blue value and a green value for each of one or more areas within the corresponding pixel.

98. The position measurement system of any one of aspects 88 through 97, wherein, for at least some of the received images, (i) the instructions further cause the computer system to determine at least one color calibration factor based on a white area within the corresponding pixel, and (ii) the instructions cause the computer system to identify the corresponding pixel in part by applying the determined at least one color calibration factor to one or more colors detected within the corresponding pixel.

99. A position measurement system for use in a hip arthroplasty procedure, the position measurement system comprising: an acetabular liner component having an inner concave surface and an outer convex surface, wherein the inner concave surface is visually coded with a plurality of liner pixels, and wherein each pixel of the plurality of liner pixels uniquely specifies a position on the inner concave surface; and a prosthetic femoral component comprising a femoral head component, wherein the femoral head component and the acetabular liner component are shaped such that a ball-and-socket joint is formed when the femoral head component comes into contact with the inner concave surface of the acetabular liner, and wherein the femoral head component comprises (i) a microscopic imaging system that is embedded in the femoral head component and is configured to capture images that, while the ball-and-socket joint is formed, are sized so as to each contain an entirety of no more than a single pixel of the plurality of liner pixels at any given time, the microscopic imaging system including an image sensor and a lens system, (ii) a wireless transceiver embedded within the femoral head component, the wireless transceiver including one or more antennas and a radio frequency (RF) module and being configured to transmit images captured by the image sensor to a destination external to the prosthetic femoral component, and (iii) a battery that is entirely embedded within the femoral head component and electrically coupled to the wireless transceiver.

100. The position measurement system of aspect 99, wherein the lens system includes (i) an objective lens, and (ii) a camera lens situated between the image sensor and the objective lens.

101. The position measurement system of aspect 100, wherein the camera lens has a focal length between 1.8 and 7.2 millimeters, and the objective lens has a focal length between 0.6 and 2.4 millimeters.

102. The position measurement system of any one of aspects 99 through 101, wherein the image sensor includes a plurality of image sensor pixels arranged in a two-dimensional array.

103. The position measurement system of aspect 100, wherein the image sensor includes fewer than 300,000 image sensor pixels.

104. The position measurement system of aspect 102 or 103, wherein each image sensor pixel has a largest dimension of less than 5 micrometers.

105. The position measurement system of any one of aspects 99 through 104, wherein the lens system provides a magnification ratio between 2:1 and 5:1.

106. The position measurement system of any one of aspects 99 through 105, wherein the wireless transceiver is configured to transmit the images captured by the image sensor to the destination external to the prosthetic femoral component using a Bluetooth communication protocol.

107. The position measurement system of any one of aspects 99 through 106, wherein the wireless transceiver is configured to transmit the images captured by the image sensor to the destination external to the prosthetic femoral component at a rate of at least 30 frames per second, substantially in real time as the images are captured by the image sensor.

108. The position measurement system of any one of aspects 99 through 107, wherein the acetabular liner component includes a plurality of pressure sensors arranged along an outer perimeter of the inner concave surface.

109. The position measurement system of any one of aspects 99 through 108, further comprising: a computer system comprising one or more processors and a memory, wherein the memory stores instructions that, when executed by the one or more processors, cause the computer system to receive the images transmitted by the wireless transceiver, for each received image, process the received image to identify a corresponding pixel of the plurality of liner pixels, and based on a plurality of the identified pixels, generate data representing a path of at least a portion of the femoral head component relative to the acetabular liner component.

110. The position measurement system of aspect 109, wherein the instructions cause the computer system to generate data representing a path of a point on an external surface of the femoral head component relative to the acetabular liner component.

111. The position measurement system of aspect 110, wherein the computer system further comprises a display, and wherein the instructions further cause the computer system to present to a user, on the display, a visual representation of the path of the point on the external surface of the femoral head component relative to the acetabular liner component, substantially in real time as the images are captured by the image sensor.

112. The position measurement system of aspect 111, wherein the instructions further cause the computer system to: generate a visual representation of a safe zone, the safe zone indicating a positioning of the point on the external surface of the femoral head component, relative to the acetabular liner component, that is not expected to result in hip dislocation; and present the safe zone on the display in conjunction with the displayed visual representation of the path.

113. The position measurement system of aspect 112, wherein the instructions further cause the computer system to: generate one or both of (i) an audible alarm, or (ii) a visual alarm, either when the visual representation of the path comes within a threshold distance of a perimeter of the visual representation of the safe zone, or when the visual representation of the path goes outside of the perimeter of the visual representation of the safe zone.

114. The position measurement system of aspect 112 or 113, wherein the safe zone is specific to a patient for which the hip arthroplasty procedure is being performed.

115. The position measurement system of aspect 114, wherein the safe zone is specific to at least (i) a height of the patient, and (ii) one or more distances between one or more portions of a pelvis of the patient and one or more portions of a femur of the patient, as measured while the patient is in one or more different poses.

116. The position measurement system of any one of aspects 109 through 115, wherein the acetabular liner component includes a plurality of pressure sensors arranged along an outer perimeter of the inner concave surface, and wherein the instructions further cause the computer system to: monitor pressure measurements of the one or more pressure sensors; and generate, based on the monitored pressure measurements, an audio or visual indication of when a surface is impinging upon the acetabular liner component.

117. The position measurement system of any one of aspects 109 through 116, wherein the instructions cause the computer system to identify the corresponding pixel of the plurality of liner pixels at least by detecting a combination and arrangement of colors within the corresponding pixel.

118. The position measurement system of any one of aspects 109 through 117, wherein the instructions cause the computer system to identify the corresponding pixel of the plurality of liner pixels at least by measuring a blue value and a green value for each of one or more areas within the corresponding pixel.

119. The position measurement system of any one of aspects 109 through 118, wherein, for at least some of the received images, (i) the instructions further cause the computer system to determine at least one color calibration factor based on a white area within the corresponding pixel, and (ii) the instructions cause the computer system to identify the corresponding pixel in part by applying the determined at least one color calibration factor to one or more colors detected within the corresponding pixel.

120. A method for improving hip stability outcomes for hip arthroplasty procedures, the method comprising: inserting a trial prosthetic femoral component into a femur of a patient, the trial prosthetic femoral component including a femoral head component and a microscopic imaging system embedded in the femoral head component; inserting a trial acetabular liner component into a pelvis of the patient, the trial acetabular liner component having an inner concave surface and an outer convex surface, the inner concave surface being visually coded with a plurality of liner pixels, and each pixel of the plurality of liner pixels uniquely specifying a position on the inner concave surface; wirelessly transmitting a stream of real-time images from the femoral head component to a computing system external to the trial prosthetic femoral component, each of the real-time images being microscopically focused, at any given time while the femoral head component and the inner concave surface form a ball-and-socket joint, on a particular one of the plurality of liner pixels; processing, by the computing system, each received image to identify a corresponding pixel of the plurality of liner pixels; and generating, by the computing system and based on a plurality of the identified pixels, data representing a path of at least a portion of the femoral head component relative to the acetabular liner component.

121. The method of aspect 120, wherein generating data representing a path of at least a portion of the femoral head component relative to the acetabular liner component includes generating data representing a path of a point on an external surface of the femoral head component relative to the acetabular liner component.

122. The method of aspect 121, further comprising: presenting to a user, on a display, a visual representation of the path of the point on the external surface of the femoral head component relative to the acetabular liner component, substantially in real time as the images are captured by the image sensor.

123. The method of aspect 122, further comprising: generating, by the computer system, a visual representation of a safe zone, the safe zone indicating a positioning of the point on the external surface of the femoral head component, relative to the acetabular liner component, that is not expected to result in hip dislocation; and presenting the safe zone on the display in conjunction with the displayed visual representation of the path.

124. The method of aspect 123, further comprising: generating, by the computer system, one or both of (i) an audible alarm, or (ii) a visual alarm, either when the visual representation of the path comes within a threshold distance of a perimeter of the visual representation of the safe zone, or when the visual representation of the path goes outside of the perimeter of the visual representation of the safe zone.

125. The method of aspect 123 or 124, wherein the safe zone is specific to a patient for which the hip arthroplasty procedure is being performed.

126. The method of aspect 125, wherein the safe zone is specific to at least (i) a height of the patient, and (ii) one or more distances between one or more portions of a pelvis of the patient and one or more portions of a femur of the patient, as measured while the patient is in one or more different poses.

127. The method of any one of aspects 120 through 126, wherein processing each received image to identify a corresponding pixel includes detecting a combination and arrangement of colors within the corresponding pixel.

128. The method of any one of aspects 120 through 127, wherein processing each received image to identify a corresponding pixel includes measuring a blue value and a green value for each of one or more areas within the corresponding pixel.

129. The method of any one of aspects 120 through 128, further comprising: for at least some of the received images, determining, by the computer system, at least one color calibration factor based on a white area within the corresponding pixel, wherein processing each received image to identify a corresponding pixel includes applying the determined at least one color calibration factor to one or more colors detected within the corresponding pixel.

We claim:

1. A position measurement system for use in a hip arthroplasty procedure, the position measurement system comprising:
   an acetabular liner component having an inner concave surface and an outer convex surface, wherein the acetabular liner component includes at least two magnetic sensors arranged in a spatially distributed manner and a wireless transceiver configured to transmit measured magnetic field data to a destination external to the acetabular liner component;
   a prosthetic femoral component comprising a femoral head component, wherein
      the femoral head component and the acetabular liner component are shaped such that a ball-and-socket joint is formed when the femoral head component comes into contact with the inner concave surface of the acetabular liner component,
      while the ball-and-socket joint is formed, and in at least some orientations of the femoral head component relative to the acetabular liner component, a contact point on an external surface of the femoral head component contacts the inner concave surface, and
      the femoral head component includes at least one permanent magnet; and
   a computer system comprising one or more processors and a memory, wherein the memory stores instructions that, when executed by the one or more processors, cause the computer system to:

determine orientations of the femoral head component relative to the acetabular liner component substantially in real time at least by inputting the measured magnetic field data transmitted by the wireless transceiver, or data derived from the measured magnetic field data, to a trained neural network configured to output data indicative of the orientations of the femoral head component relative to the acetabular liner component, detect a dislocation of the femoral head component from the acetabular liner component based on the measured magnetic field data indicative of sensor readings captured by the at least two magnetic sensors, the measured magnetic field data being representative of the orientations of the femoral head component relative to the acetabular liner component, and output data indicative of whether the dislocation is due to implant impingement or bony impingement.

2. The position measurement system of claim 1, wherein the acetabular liner component and the prosthetic femoral component are trial components to be removed prior to completion of the hip arthroplasty procedure.

3. The position measurement system of claim 1, wherein the at least one permanent magnet is entirely embedded in the femoral head component.

4. The position measurement system of claim 1, wherein each of the at least two magnetic sensors is a multi-axis sensor capable of detecting magnetic field intensity and direction in three dimensions.

5. The position measurement system of claim 1, wherein the acetabular liner component includes exactly three magnetic sensors, and the three magnetic sensors are evenly distributed about a center axis of the acetabular liner component.

6. The position measurement system of claim 1, wherein:
the prosthetic femoral component further comprises a femoral neck component; and
the femoral head component is configured to physically couple to the femoral neck component in a removable manner.

7. The position measurement system of claim 6, wherein:
the prosthetic femoral component further comprises a broach component; and
the femoral neck component is configured to physically couple to the broach component in a removable manner.

8. The position measurement system of claim 1, wherein:
the wireless transceiver includes one or more antennas and a radio frequency (RF) module.

9. The position measurement system of claim 8, wherein the wireless transceiver is configured to transmit the measured magnetic field data to the destination external to the acetabular liner component using a Bluetooth communication protocol.

10. The position measurement system of claim 8, wherein the acetabular liner component comprises a microcontroller configured to receive the sensor readings from the at least two magnetic sensors.

11. The position measurement system of claim 10, wherein the acetabular liner component further comprises a battery electrically coupled to the microcontroller.

12. The position measurement system of claim 11, wherein the at least two magnetic sensors, the microcontroller, the wireless transceiver, and the battery are entirely embedded in a body of the acetabular liner component.

13. The position measurement system of claim 8, wherein the wireless transceiver is configured to transmit the measured magnetic field data to the destination external to the acetabular liner component at a rate of at least 8 frames per second, substantially in real time as the sensor readings are captured by the at least two magnetic sensors.

14. The position measurement system of claim 8,
wherein the memory stores instructions that, when executed by the one or more processors, further cause the computer system to:
receive the measured magnetic field data transmitted by the wireless transceiver, and
process the received measured magnetic field data to determine the orientations of the femoral head component relative to the acetabular liner component, substantially in real time as the at least two magnetic sensors capture the sensor readings.

15. The position measurement system of claim 14, wherein the instructions cause the computer system to generate, based on the determined orientations, data representing a path of the contact point relative to the acetabular liner component.

16. The position measurement system of claim 15, wherein the computer system further comprises a display, and wherein the instructions further cause the computer system to present to a user, on the display, a visual representation of the path of the contact point relative to the acetabular liner component, substantially in real time as the at least two magnetic sensors capture the sensor readings.

17. The position measurement system of claim 16, wherein the instructions further cause the computer system to:
generate a visual representation of a safe zone, the safe zone indicating a positioning of the contact point, relative to the acetabular liner component, that is not expected to result in hip dislocation; and
present the safe zone on the display in conjunction with the displayed visual representation of the path.

18. The position measurement system of claim 17, wherein the instructions further cause the computer system to:
generate one or both of (i) an audible alarm, or (ii) a visual alarm, either when the visual representation of the path comes within a threshold distance of a perimeter of the visual representation of the safe zone, or when the visual representation of the path goes outside of the perimeter of the visual representation of the safe zone.

19. The position measurement system of claim 17, wherein the safe zone is specific to at least (i) a height of the patient, and (ii) one or more distances between one or more portions of a pelvis of the patient and one or more portions of a femur of the patient, as measured while the patient is in one or more different poses.

20. The position measurement system of claim 14, wherein the instructions cause the computer system to determine the orientations of the femoral head component relative to the acetabular liner component at least by using the measured magnetic field data to determine projections of the contact point onto the inner concave surface.

21. The position measurement system of claim 14, wherein the instructions cause the computer system to determine the orientations of the femoral head component relative to the acetabular liner component at least by:
determining one or more ambient magnetic fields that are measured by the at least two magnetic sensors while the ball-and-socket joint is not formed;

determining at least one magnetic field calibration factor based on the one or more ambient magnetic fields; and determining the orientations of the femoral head component relative to the acetabular liner component based on the measured magnetic field data and the at least one magnetic field calibration factor.

22. A position measurement system for use in a hip arthroplasty procedure, the position measurement system comprising:

an acetabular liner component having an inner concave surface and an outer convex surface, wherein the acetabular liner component includes at least two magnetic sensors arranged in a spatially distributed manner;

a prosthetic femoral component comprising a femoral head component, wherein the femoral head component and the acetabular liner component are shaped such that a ball-and-socket joint is formed when the femoral head component comes into contact with the inner concave surface of the acetabular liner component, while the ball-and-socket joint is formed, and in at least some orientations of the femoral head component relative to the acetabular liner component, a contact point on an external surface of the femoral head component contacts the inner concave surface, and the femoral head component includes at least one permanent magnet; and a computer system comprising one or more processors and a memory, wherein the memory stores instructions that, when executed by the one or more processors, cause the computer system to:

determine one or more ambient magnetic fields that are measured by the at least two magnetic sensors while the ball-and-socket joint is not formed, determine at least one magnetic field calibration factor based on the one or more ambient magnetic fields, determine orientations of the femoral head component relative to the acetabular liner component based on measured magnetic field data indicative of sensor readings captured by the at least two magnetic sensors and the at least one magnetic field calibration factor, detect a dislocation of the femoral head component from the acetabular liner component based on the measured magnetic field data, and output data indicative of whether the dislocation is due to implant impingement or bony impingement.

23. The position measurement system of claim 22, wherein the acetabular liner component includes exactly three magnetic sensors, and the three magnetic sensors are evenly distributed about a center axis of the acetabular liner component.

24. The position measurement system of claim 22, wherein:

the acetabular liner component further comprises a wireless transceiver;

the wireless transceiver includes one or more antennas and a radio frequency (RF) module; and the wireless transceiver is configured to transmit the measured magnetic field data to a destination external to the acetabular liner component.

25. The position measurement system of claim 22, wherein:

the instructions cause the computer system to determine the orientations of the femoral head component relative to the acetabular liner component at least by inputting the measured magnetic field data, or data derived from the measured magnetic field data, to a trained neural network; and the trained neural network outputs data indicative of the orientations of the femoral head component relative to the acetabular liner component.

* * * * *